United States Patent [19]
Firestein et al.

[11] Patent Number: 5,646,128
[45] Date of Patent: Jul. 8, 1997

[54] METHODS FOR TREATING ADENOSINE KINASE RELATED CONDITIONS

[75] Inventors: Gary S. Firestein, Del Mar; Bheemarao G. Ugarkar, Escondido; Leonard P. Miller, Carlsbad; Harry E. Gruber, Rancho Santa Fe; David A. Bullough, San Diego; Mark D. Erion, Del Mar; Angelo J. Castellino, San Diego, all of Calif.; Clinton E. Browne, Gainesville, Fla.

[73] Assignee: Gensia, Inc., San Diego, Calif.

[21] Appl. No.: 349,125

[22] Filed: Dec. 1, 1994

Related U.S. Application Data

[63] Continuation of Ser. No. 192,645, Feb. 3, 1994, abandoned, which is a continuation-in-part of Ser. No. 14,190, Feb. 3, 1993, abandoned, which is a continuation-in-part of Ser. No. 812,916, Dec. 23, 1991, abandoned, which is a continuation-in-part of Ser. No. 647,117, Jan. 23, 1991, abandoned, which is a continuation-in-part of Ser. No. 466,979, Jan. 18, 1990, abandoned, which is a continuation-in-part of Ser. No. 408,707, Sep. 15, 1989, abandoned.

[51] Int. Cl.$^6$ .................................................. A61K 31/70
[52] U.S. Cl. ...................... 514/46; 514/45; 514/825; 514/885; 514/886
[58] Field of Search ......................... 514/45, 46, 825, 514/885, 886

[56] References Cited

PUBLICATIONS

Biochemical Pharmacology, vol. 28, pp. 501–510, Received 4 May 1978; Accepted 22 Jun. 1978 (Author: Agarwal, et al.).

Molecular Pharmacology, vol. 7, pp. 663–673; Received Jul. 20, 1971 (Author: Divekar and Hakala).

J. Med. Chem. 1984, vol. 27, pp. 285–292; Received May 9, 1983 (Author: Bergstrom, et al.).

M.G. Stout et al., *J. Org. Chem.*, vol. 33, No. 3, Mar. 1968, pp. 1219–1225.

Y. Tominaga et al., *J. Heterocyclic Chem.*, 27, pp. 647–660 (1990).

I. Chut et al., *J. Med. Chem.*, 1975 vol. 18, No. 2, pp. 161–165.

H.B. Cottam et al., *J. Med. Chem.*, 1984, 27, pp. 119–1127.

J.S. Pudlo et al., *J. Med. Chem.*, 1990, 33, pp. 1984–1992.

C.W. Noell et al., *J. Heterocyclic Chem.*, 1964, 1, pp. 34–41.

M. Ikehara et al., *Tetrahedron*, vol. 26, pp. 5757–5763 (1970).

J. Davoll, *J. Chem. Soc.*, 1960, pp. 131–138.

B.C. Hinshaw et al., *J. Heterocyclic Chem.*, vol. 6, pp. 215–221 (1969).

H. Rosemeyer et al., *Helvetica Chimica Acta*, vol. 71, pp. 1573–1585, (1988).

J.R. Synder et al., *Carbohydrate Research*, 163 (1987), pp. 169–188.

R.A. Carboni et al., *J. Amer. Chem. Soc.*, vol. 80 (1958), pp. 2838–2840.

E.C. Taylor et al., *J. Org. Chem.*, vol. 31 (1966), pp. 342–343.

S. Kobayashi, *Chem. Pharm. Bull.*, 21(5) (1973), pp. 941–951.

*Primary Examiner*—James O. Wilson
*Attorney, Agent, or Firm*—Lyon & Lyon

[57] ABSTRACT

Novel compounds which selectively inhibit adenosine kinase and methods of preparing adenosine kinase inhibitors are provided. Also provided are methods of treating various inflammatory conditions, including arthritis and SIRS, which may be ameliorated by increased local concentrations of adenosine using adenosine kinase inhibitors.

13 Claims, 18 Drawing Sheets

8

9a X=H
9b X=CH$_3$O
9c X=N$_3$

10a X=H
10b X=CH$_3$O
10c X=N$_3$

20a F=Cl
20b F=NH₂ or NHR
20c F=RS
20d F=R

24a F=O(H)
24b F=NH₂ or NHR
24c F=R

| B | D | E | F | G |
|---|---|---|---|---|
| CH₃ | Br | H | Cl | H |
| CH₃ | I | H | Cl | H |
| CH₃ | I | H | SH | H |
| -CH₂-CH₃ | Br | H | Cl | H |
| -CH₂-CH₃ | I | H | Cl | H |
| -CH=CH₂ | Br | H | Cl | H |
| -CH=CH₂ | I | H | Cl | H |
| -CH₂-N₃ | I | H | Cl | H |
| -CH₂-CH₂-N₃ | I | H | Cl | H |
| -CH₂-N₃ | Br | H | Cl | H |
| CH₃ | Br | H | HN-aryl | H |
| CH₃ | I | H | HN-aryl | H |
| CH₂OH | I | H | HN-aryl | H |
| CH₂OH | Br | H | HN-aryl | H |

*p<0.01 COMPARED TO LPS, LPS+8SPT, LPS+515+8SPT

METHODS FOR TREATING ADENOSINE KINASE RELATED CONDITIONS

CROSS-REFERENCE TO RELATED APPLICATIONS

This application is a continuation of application Ser. No. 08/192,645, filed Feb. 3, 1994, abandoned, which is a continuation-in-part of Ser. No. 08/014,190, filed Feb. 3, 1993 now abandoned; which is a continuation-in-part of Ser. No. 07/812,916, filed Dec. 23, 1991 now abandoned; which is a continuation-in-part of Ser. No. 07/647,117, filed Jan. 23, 1991 now abandoned; which is a continuation-in-part of Ser. No. 466,979, filed Jan. 18, 1990 now abandoned; which is a continuation-in-part of Ser. No. 408,707, filed Sep. 15, 1989 now abandoned; the disclosures of these applications are incorporated herein by reference.

FIELD OF INVENTION

This invention relates to the use of adenosine kinase inhibitors and specifically to purine, pyrrolo[2,3-d]pyrimidine and pyrazolo[3,4-d]pyrimidine nucleoside analogs having activity as adenosine kinase inhibitors. The invention also relates to the use of these and other adenosine kinase inhibitors in the treatment of inflammation, sepsis, septic shock, burns and diseases which can be regulated by increasing the local concentration of adenosine.

BACKGROUND OF THE INVENTION

Adenosine has been reported to have cardioprotective (Olafsson et al., Circulation, 1987, 76:1135–1145) and neuroprotective properties (Dragunow and Faull, Trends in Pharmacol. Sci., 1988, 9:193; Marangos, Medical Hypothesis, 1990, 32:45). It is reportedly released from cells in response to alterations in the supply of or demand for oxygen (Schrader, Circulation, 1990, 81:389–391), is said to be a potent vasodilator, and is believed to be involved in the metabolic regulation of blood flow (Berne, Circ. Res., 1980, 47:808–813). However, adenosine has a short half life (<1 sec) in human blood (Moser, et al., Am. J. Physiol., 1989, 256:C799–C806), and therefore high doses of adenosine would need to be administered continuously to achieve effective levels. Adenosine has been reported to exhibit negative inotropic, chronotropic and dromotropic effects (Belardinelli et al., Prog. in Cardiovasc. Diseases, 1989, 32:73–97) and to cause coronary steal by preferentially dilating vessels in nonischemic regions. Consequently, high doses of adenosine are toxic and this toxicity severely limits its therapeutic potential. However, it is believed that by increasing adenosine concentration locally, i.e. at the target site within the target tissue, the beneficial effects of adenosine can be provided without the toxic systemic effects. Adenosine has been reported to be an endogenous modulator of inflammation by virtue of its effects on stimulated granulocyte function (Cronstein et al., J. Clin. Invest., 1986, 78:760–770) and on macrophage, lymphocyte and platelet function. Adenosine receptor agonists have been reported to be beneficial in an experimental model of inflammation (Schrier, et al., J. Immunol., 1990, 145:1874–1879). Adenosine and a related analog have been reported to inhibit in vitro production of the cytokine, tumor necrosis factor alpha (Parmely et al., FASEB Journal, 1991, 5:A 1602).

Adenosine kinase is a cytosolic enzyme which catalyzes the phosphorylation of adenosine to AMP. Inhibition of adenosine kinase can potentially reduce the ability of the cell to utilize adenosine, leading to increased adenosine outside of the cell where it is pharmacologically active. However, the regulation of adenosine concentration is complex and involves other adenosine-metabolizing enzymes each with different kinetic properties and mechanisms of regulation. Adenosine can also be deaminated to inosine by adenosine deaminase (ADA) and condensed with L-homocysteine to S-adenosylhomocysteine (SAH) by SAH hydrolase. The role of each of these enzymes in modulating adenosine concentration is dependent on the prevailing physiological conditions, is tissue specific and is not well understood.

A number of nucleosides including purine, pyrrolo[2,3-d]pyrimidine and pyrazolo[3,4-d]pyrimidine analogs have been evaluated for inhibition of adenosine kinase but were reported to have $K_i$'s of greater than 800 nM (Caldwell and Henderson, Cancer Chemother. Rep., 1971, 2:237–246; Miller et al., J. Biol. Chem., 1979, 254:2346–2352). A few compounds have been reported as potent inhibitors of adenosine kinase with Ki's of less than 100 nM. These are the purine nucleosides, 5'-amino-5'-deoxyadenosine (Miller et al., J. Biol. Chem., 1979, 254:2346–2352) and 1,12-bis (adenosin-N6-yl)dodecane (Prescott et al., Nucleosides & Nucleotides, 1989, 8:297), and the pyrrolopyrimidine nucleosides, 5-iodotubercidin (Henderson et al., Cancer Chemotherapy Rep. Part 2, 1972, 3:71–85; Bontemps et al., Proc. Natl. Acad. Sci. USA, 1983, 80:2829–2833; Davies et al., Biochem. Pharmacol., 1986, 35:3021–3029)and 5'-deoxy-5-iodotubercidin (Davies et al., Biochem. Pharmacol., 1984, 33:347–355; Davies et al., Biochem. Pharmacol., 1986, 35:3021–3029).

Some of these compounds have been used to evaluate whether adenosine kinase inhibition might lead to increased extracellular adenosine concentrations. In rat cardiomyocytes, inhibition of adenosine deaminase by 2'-deoxycoformycin was reported to have no effect on adenosine release from the cells. In contrast, inhibition of ADA together with adenosine kinase by 5'-amino-5'-deoxyadenosine resulted in a 6-fold increase in adenosine release (Zoref-Shani et al., J. Mol. Cell. Cardiol., 1988, 20:23–33). The effects of the adenosine kinase inhibitor alone were not reported. Similar results were reported in isolated guinea pig hearts; in these studies addition of 5'-amino-5'-deoxyadenosine to the perfusion medium, in the presence of EHNA to inhibit deamination, was reported to result in a 15-fold increase of adenosine release (Schrader, in Regulatory Function of Adenosine; (Berne et al.) eds. pp. 133–156, 1983). These effects were not apparent in the absence of ADA inhibition and other studies using isolated rat hearts perfused with 5-iodotubercidin alone, have reported no increase in perfusate adenosine concentration under normoxic conditions (Newby et al., Biochem. J., 1983, 214:317–323) or under hypoxic, anoxic or ischemic conditions (Achtenberg et al., Blochem, J., 1986, 235:13–17). In other studies, adenosine release has been measured in neuroblastoma cells in culture and compared with that of a variant deficient in adenosine kinase (AK-). The AK- cells used in this study were said to release adenosine at an accelerated rate; the concentration of adenosine in the growth medium was reported to be elevated compared to the normal cells (Green, J. Supramol. Structure, 1980, 13:175–182). In rat and guinea pig brain slices, adenosine uptake was reportedly inhibited by the adenosine kinase inhibitors, 5-iodotubercidin and 5'-deoxy-5-iodotubercidin (Davis et al., Biochem. Pharmacol., 1984, 33:347–355). However, inhibition of uptake and intracellular trapping via phosphorylation does not necessarily result in increased extracellular adenosine, since the adenosine could enter other metabolic pathways or the percentage of adenosine being phosphorylated could be insignificant compared to the total adenosine removed.

The effects of adenosine and certain inhibitors of adenosine catabolism, including 5-iodotubericidin were evaluated in an experimental model in which dog hearts were subjected to ischemia and reperfusion; 5-iodotubericidin was reported to have inconsistent effects (Wu, et al., *Cytobios*, 1987, 50:7–12).

Although the adenosine kinase inhibitors, 5'-amino-5'-deoxyadenosine and 5-iodotubercidin have been widely used in experimental models, the susceptibility of 5'-amino-5'-deoxyadenosine to deamination, and hence its potentially short half life, and the cytotoxicity of 5-iodotubercidin make their clinical utility limited and may limit interpretations based on these compounds. The pyrrolo[2,3-d]pyrimidines, 5-iodotubercidin and 5'-deoxy-5-iodotubercidin have been reported to cause pronounced general flaccidity and much-reduced spontaneous locomotor activity in mice, interpreted to be skeletal muscle relaxation; to cause hypothermia in mice; and to decrease blood pressure and heart rate in anesthetized rats (Daves et al., *Biochem. Pharmacol.*, 1984, 33:347–355; Daves et al., *Blochem. Pharmacol.*, 1986, 35:3021–3029; U.S. Pat. No. 4,455,420). The skeletal muscle effects of these compounds have been poorly documented, while the other effects were considered significant toxicities. It is believed that studies using these compounds were curtailed due to these toxicities and also because of their limited availability.

SUMMARY OF THE INVENTION

The present invention is directed to novel uses of compounds which are potent and selective adenosine kinase inhibitors.

Another aspect of the present invention is directed to the clinical use of adenosine kinase inhibitors as a method of increasing adenosine concentrations in biological systems. In vivo inhibition of adenosine kinase prevents phosphorylation of adenosine resulting in higher local concentrations of endogenous adenosine. As a result of the very short half-life of adenosine and very low quantities of adenosine in tissues, this effect is most pronounced in regions producing the most adenosine such as ischemic regions. Hence, the beneficial effects of adenosine are enhanced in a site and event specific manner and toxic systemic effects are reduced.

In particular, in one preferred aspect, the present invention is directed to novel nucleoside analogs which comprise a 5'-modified ribose linked to a substituted purine, pyrrolo[2,3-d]pyrimidine, or pyrazolo[3,4-d]pyrimidine base. Certain preferred compounds within these groups possess potencies many times greater than previously described inhibitors of adenosine kinase. The compounds of the present invention possess advantages for pharmaceutical use such as enhanced pharmacological selectivity, efficacy, bioavailability, ease of manufacture and compound stability.

The novel compounds of the present invention and other adenosine kinase inhibitors may be used clinically to treat medical conditions where an increased localized adenosine concentration is beneficial. Accordingly, the present invention is directed to the prophylactic and affirmative treatment of ischemic conditions such as myocardial infarction, angina, percutaneous transluminal coronary angiography (PTCA), stroke, other thrombotic and embolic conditions, neurological conditions such as seizures and psychosis, and other conditions benefited by enhanced adenosine levels such as inflammation, arthritis, autoimmune diseases, cardiac arrhythmias, ulcers and irritable bowel syndrome.

In particular, the present invention is also directed to the prophylactic and affirmative treatment of sepsis, septicemia (including but not limited to endotoxemia), and various forms of septic shock (including but not limited to endotoxic shock.) For example, adenosine kinase inhibitors will be useful in the prophylactic or affirmative treatment of a localized or systemic inflammatory response to infection by one or more of several types of organisms, including bacteria (gram negative or gram positive), viruses (including retroviruses), mycobacteria, yeast, protozoa or parasites.

Furthermore, the present invention is directed to the treatment of disorders in which vascular leakage is involved. In particular, the present invention is directed to the treatment of burn injury.

DEFINITIONS

In accordance with the present invention and as used herein, the following terms, are defined with the following meanings, unless explicitly stated otherwise.

The term "hydrocarbyl" refers to an organic radical comprised of carbon chains to which hydrogen and other elements are attached. The term includes alkyl, alkenyl, alkynyl and aryl groups, groups which have a mixture of saturated and unsaturated bonds, carbocyclic rings and includes combinations of such groups. It may refer to straight-chain, branched-chain cyclic structures or combinations thereof.

The term "aryl" refers to aromatic groups which have at least one ring having a conjugated pi electron system and includes carbocyclic aryl, heterocyclic aryl and biaryl groups, all of which may be optionally substituted.

Carbocyclic aryl groups are groups wherein the ring atoms on the aromatic ring are carbon atoms. Carbocyclic aryl groups include monocyclic carbocyclic aryl groups and optionally substituted naphthyl groups.

The term "monocyclic carbocyclic aryl" refers to optionally substituted phenyl, being preferably phenyl or phenyl substituted by one to three substituents, such being advantageously lower alkyl, hydroxy, lower alkoxy, lower alkanoyloxy, halogen, cyano, trihalomethyl, lower acylamino or lower alkoxycarbonyl.

"Optionally substituted naphthyl" refers to 1- or 2-naphthyl or 1- or 2-naphthyl preferably substituted by lower alkyl, lower alkoxy or halogen.

Heterocyclic aryl groups are groups having from 1 to 3 heteroatoms as ring atoms in the aromatic ring and the remainder of the ring atoms carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl, and the like, all optionally substituted.

Optionally substituted furanyl represents 2- or 3-furanyl or 2- or 3-furanyl preferably substituted by lower alkyl or halogen.

Optionally substituted pyridyl represents 2-, 3- or 4-pyridyl or 2-, 3- or 4-pyridyl preferably substituted by lower alkyl or halogen.

Optionally substituted thienyl represents 2- or 3-thienyl, or 2- or 3-thienyl preferably substituted by lower alkyl or halogen.

The term "biaryl" represents phenyl substituted by carbocyclic aryl or heterocyclic aryl as defined herein, ortho, meta or para to the point of attachment of the phenyl ring, advantageously para; biaryl is also represented as the —$C_6H_4$—Ar substituent where Ar is aryl.

The term "aralkyl" refers to an alkyl group substituted with an aryl group. Suitable aralkyl groups include benzyl, picolyl, and the like, and may be optionally substituted.

The term "lower" referred to herein in connection with organic radicals or compounds respectively defines such with up to and including 7, preferably up to and including 4 and advantageously one or two carbon atoms. Such groups may be straight chain or branched.

The terms (a)"alkyl amino", (b)"arylamino", and (c)"aralkylamino", respectively, refer to the groups —NRR' wherein respectively, (a) R is alkyl and R' is hydrogen or alkyl; (b) R is aryl and R' is hydrogen or aryl, and (c) R is aralkyl and R' is hydrogen or aralkyl.

The term "acyl" refers to hydrocarbyl—C(O)— or HC(O)—.

The terms "acylamino" refers to RC(O)NR— and (RC(O))$_2$N— respectively, wherein each R is independently hydrogen or hydrocarbyl.

The term "α-alkoxyalkylidene" refers to hydrocarbyl-O—CR (an orthoester) wherein R is hydrogen or hydrocarbyl.

The term "hydrocarbyloxycarbonyloxy" refers to the group ROC(O)O-wherein R is hydrocarbyl.

The term "lower carboalkoxymethyl" or "lower hydrocarbyloxycarbonylmethyl" refers to hydrocarbyl—OC(O)CH$_2$— with the hydrocarbyl group containing ten or less carbon atoms.

The term "carbonyl" refers to —C(O)—.

The term "carboxamide" or "carboxamido" refers to —CONR$_2$ wherein each R is independently hydrogen or hydrocarbyl.

The term "lower hydrocarbyl" refers to any hydrocarbyl group of ten or less carbon atoms.

The term "alkyl" refers to saturated aliphatic groups including straight-chain, branched chain and cyclic groups.

The term "alkenyl" refers to unsaturated hydrocarbyl groups which contain at least one carbon-carbon double bond and includes straight-chain, branched-chain and cyclic groups.

The term "alkynyl" refers to unsaturated hydrocarbyl groups which contain at least one carbon-carbon triple bond and includes straight-chain, branched-chain and cyclic groups.

The term "halogen" refers to fluorine, chlorine, bromine or iodine.

The term "hydrocarbyloxycarbonylamino" refers to a urethane, hydrocarbyl—O—CONR— wherein R is H or hydrocarbyl and wherein each hydrocarbyl is independently selected.

The term "di(hydrocarbyloxycarbonyl)amino" refers to (hydrocarbyl—O—CO)$_2$N— wherein each hydrocarbyl is independently selected.

The term "hydrocarbylamino" refers to —NRR' wherein R is hydrocarbyl and R' is independently selected hydrocarbyl or hydrogen.

The term "mercapto" refers to SH or a tautomeric form.

The term "methine" refers to

The term "methylene" refers to —CH$_2$—.

The term "alkylene" refers to a divalent straight chain or branched chain saturated aliphatic radical.

The term "oxy" refers to —O— (oxygen).

The term "thio" refers to —S— (sulfur).

The term "prodrug" as used herein refers to any compound that has less intrinsic activity than the "drug" but when administered to a biological system generates the "drug" substance either as a result of spontaneous chemical reaction or by enzyme catalyzed or metabolic reaction. Reference is made to various prodrugs such as acyl esters, carbonates, and urethanes, included herein as examples. The groups illustrated are exemplary, not exhaustive and one skilled in the art could prepare other known varieties of prodrugs. Such prodrugs of the compounds of Formula I, fall within the scope of the present invention.

The term "pharmaceutically acceptable salt" includes salts of compounds of Formula I derived from the combination of a compound of this invention and an organic or inorganic acid. The compounds of Formula I are useful in both free base and salt form. In practice the use of salt form amounts to use of base form; both forms are within the scope of the present invention.

DETAILED DESCRIPTION OF THE INVENTION

Novel Adenosine Kinase Inhibitors

Figure 1A:
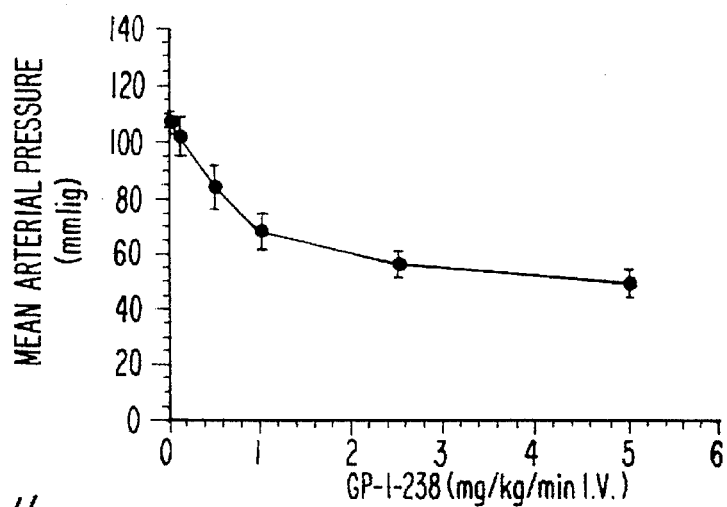
FIG. 1a depicts the effects of the adenosine kinase inhibitor GP-1-238 on mean arterial pressure following intravenous administration to anesthetized rats.
Figure 1B:
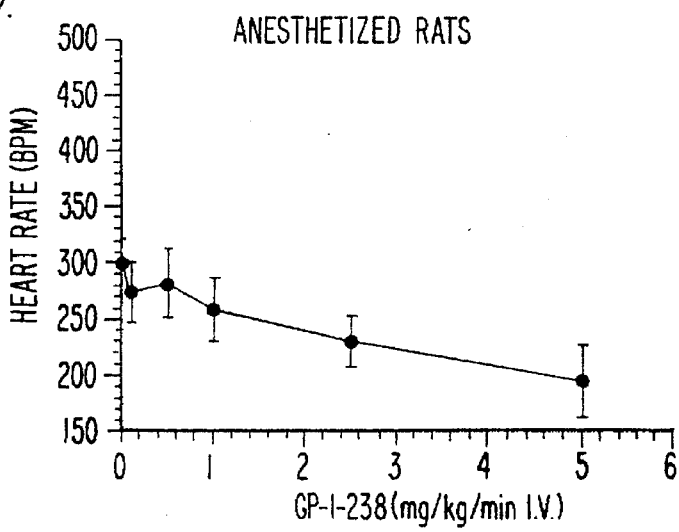
FIG. 1b depicts the effects of the adenosine kinase inhibitor GP-1-238 on heart rate following intravenous administration to anesthetized rats.
Figure 1C:
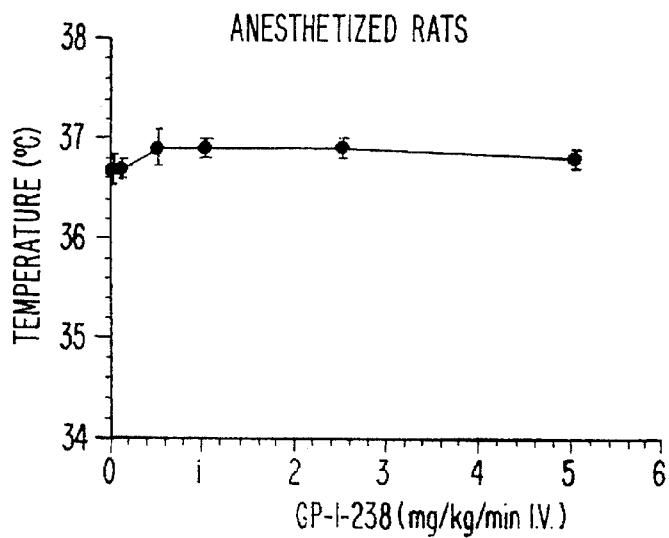
FIG. 1c depicts the effects of the adenosine kinase inhibitor GP-1-238 on body temperature following intravenous administration to anesthetized rats.
Figure 1D:
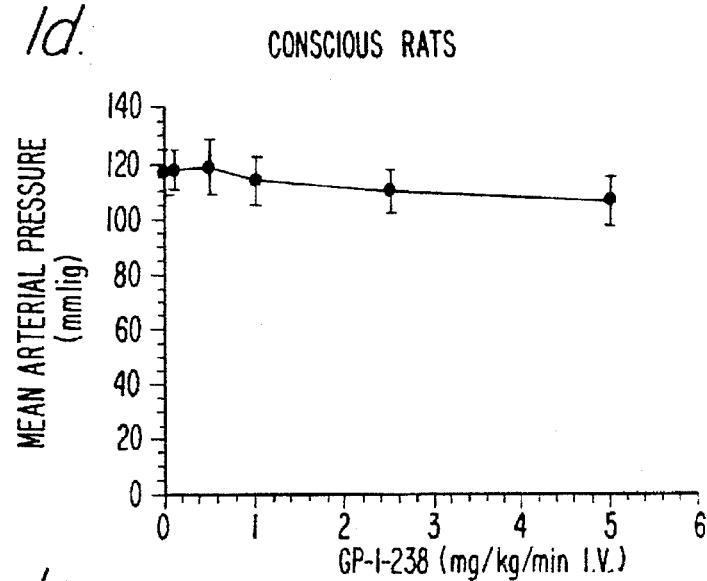
FIG. 1d depicts the effects of the adenosine kinase inhibitor GP-1-238 on mean arterial pressure following intravenous administration to conscious rats.
Figure 1E:
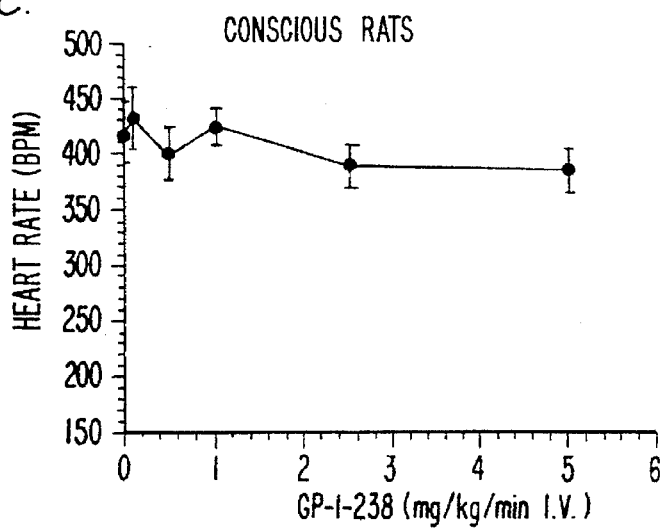
FIG. 1e depicts the effects of the adenosine kinase inhibitor GP-1-238 on heart rate following intravenous administration to conscious rats.
Figure 1F:
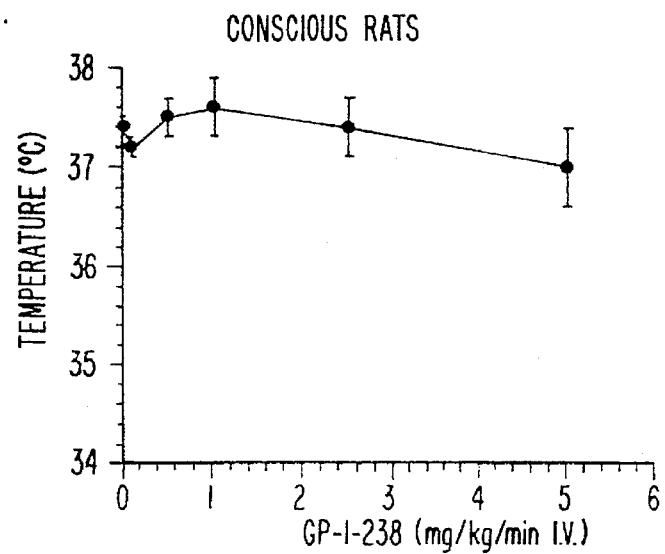
FIG. 1f depicts the effects of the adenosine kinase inhibitor GP-1-238 on body temperature following intravenous administration to conscious rats.

In one aspect, the present invention relates to the novel use of adenosine kinase inhibitors which comprise compounds of the general formula I.

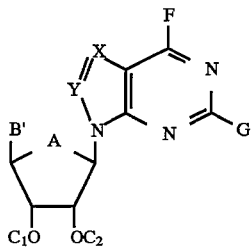
(I)

wherein:

(a) A is oxygen, methylene or sulfur;

(b) B' is —(CH$_2$)$_n$—B wherein n is 1, 2, 3 or 4 and B is hydrogen, alkyl, alkoxy, amino, alkylamino, acylamino, hydrocarbyloxycarbonylamino, mercapto, alkylthio, azido, cyano, halogen, or B' is alkenyl or alkynyl;

(c) C$_1$ and C$_2$ are each independently hydrogen, acyl, hydrocarbyloxycarbonyl or taken together form a 5-membered ring wherein C$_1$ is a single bond to C$_2$ and C$_2$ is carbonyl or α-alkoxyalkylidene;

(d) X is —C(—D)= and Y is —N= or —C(—E)=;

(e) D is hydrogen, halogen, alkyl, aryl, aralkyl, alkenyl, alkynyl, haloalkyl, cyano, cyanoalkyl, acyl, carboxamido, a carboxylic acid or carboxylic acid ester group, alkoxy, aryloxy, aralkyloxy, alkylthio, arylthio, aralkylthio, amino, alkylamino arylamino, aralkylamino, acylamino, or nitro;

(f) E is hydrogen, halogen, alkyl, or alkylthio;

(g) F is alkyl, aryl, aralkyl, halogen, amino, alkylamino, arylamino, aralkylamino, cyano, cyanoalkyl, alkoxy, aryloxy, aralkoxy, alkyithio, arylthio, aralkyithio; optionally substituted indolinyl or indolyl; pyrrolidinyl or piperazinyl; and (h) G is hydrogen, halogen, lower alkyl, lower alkoxy, lower alkylamino or lower alkylthio; and pharmaceutically acceptable salts thereof; with the proviso that:
when A is oxygen and (i) X is —C(—D)= and Y is —C(—E)=, then if B' is methyl, D is halogen, cyano or carboxamido, F is amino, then G is not hydrogen; or if D is hydrogen, then F is not amino; or (ii) X is —C(—D)= and Y is —N=, if B is hydrogen or halogen, D and G are hydrogen, then F is not amino;

or when A is methylene, X is —C(—D)=, Y is —C(—E)=, B, D, E and G are hydrogen, then F is not amino.

According to an alternative aspect of the present invention, novel adenosine kinase inhibitors are provided which have a 5'-group which comprises a hydroxyl or hydroxyl derivative. However, it is believed that due to their overall structures, those compounds which have a 5'-hydroxyl would not act as substrates for phosphorylation enzymes and, thus, would be unlikely to undergo 5'-phosphorylation or would be phosphorylated at an extremely slow rate.

One preferred group of these adenosine kinase inhibitors comprise compounds of the formula:

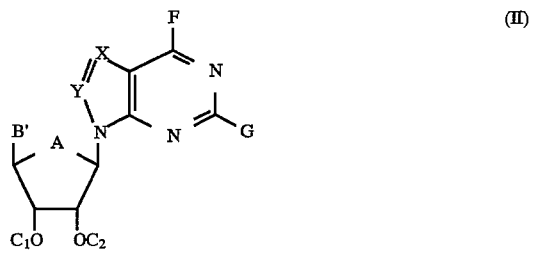
(II)

wherein:

(a) A is oxygen, methylene or sulfur;

(b) B' is —(CH$_2$)$_n$B wherein n is 1,2, 3 or 4 and B is hydroxy, acyloxy, hydrocarbyloxycarbonyloxy, or —OCONR$_2$ wherein each R is independently hydrocarbyl;

(c) C$_1$ and C$_2$ are each independently hydrogen, acyl, hydrocarbyloxycarbonyl or taken together form a 5-membered ring wherein C$_1$ is a single bond to C$_2$ and C$_2$ is carbonyl or α-alkoxyalkylidene;

(d) X is —C(—D)= and Y is —N=;

(e) D is halogen, aryl or aralkyl;

(f) F is alkyl, aryl, aralkyl, halogen, amino, alkylamino, arylamino, aralkylamino, cyano, cyanoalkyl, alkoxy, aryloxy, aralkoxy, alkylthio, arylthio, aralkylthio, optionally substituted indolinyl or indolyl, pyrrolidinyl or piperazinyl; and (g) G is hydrogen, halogen, lower alkyl, lower alkoxy, or lower alkylthio; and pharmaceutically acceptable salts thereof; with the proviso that when A is oxygen and D is halogen, then F is not amino.

Another preferred group of these adenosine kinase inhibitors comprise compounds of the formula:

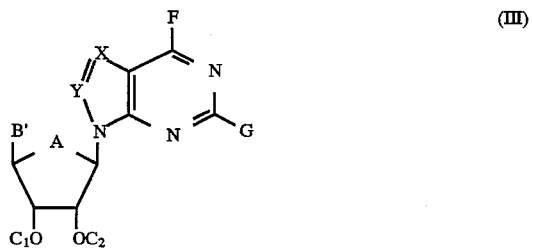
(III)

wherein:

(a) A is oxygen, methylene or sulfur;

(b) B' is —(CH$_2$)$_n$B wherein n is 1, 2, 3 or 4 and B is hydroxy, acyloxy, hydrocarbyloxycarbonyloxy, or —OCONR$_2$ wherein each R is independently hydrocarbyl;

(c) C$_1$ and C$_2$ are each independently hydrogen, acyl, hydrocarbyloxycarbonyl or taken together form a 5-membered ring wherein C$_1$ is a single bond to C$_2$ and C$_2$ is carbonyl or α-alkoxyalkylidene;

(d) X is —C(—D)= and Y is —C(—E)=;

(e) D is aryl or aralkyl;

(f) E is hydrogen, halogen, alkyl, or alkylthio;

(g) F is alkyl, aryl, aralkyl, halogen, amino, alkylamino, arylamino, aralkylamino, cyano, cyanoalkyl, alkoxy, aryloxy, aralkyloxy, alkylthio, arylthio, aralkylthio, optionally substituted indolinyl or indolyl, pyrrolidinyl or piperazinyl; and (h) G is hydrogen, halogen, lower alkyl, bower alkoxy, or lower alkylthio; and pharmaceutically acceptable salts thereof; with the proviso that: when A is oxygen, D is oxadiazolyl, triazolyl or triazinyl, E and G are both hydrogen, then F is not amino.

Also included within the present invention are adenosine kinase inhibitors which comprise modified purine nucleosides of the formula:

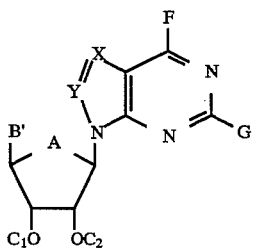

(IV)

wherein (a) A is oxygen, methylene or sulfur;

(b) B' is —CH$_2$B wherein and B is amino, alkylamino, or acylamino;

(c) C$_1$ and C$_2$ are each independently hydrogen, acyl, hydrocarbyloxycarbonyl or taken together form a 5-membered ring wherein C$_1$ is a single bond to C$_2$ and C$_2$ is carbonyl or α-alkoxyalkylidene;

(d) X is –N= and Y is —C(—E)=;

(e) E is hydrogen, halogen, alkyl, amino, alkylamino, azido, acylamino, alkoxy or alkylthio;

(f) F is halogen, amino, alkylamino, arylamino, aralkylamino, cyanoalkyl, alkoxy, aryloxy, aralkoxy, alkylthio, arylthio, aralkylthio, alkyl, aryl, aralkyl, optionally substituted indolinyl or indolyl, pyrrolidinyl or piperazinyl; and (g) G is hydrogen, halogen, lower alkyl, lower alkoxy, or lower alkylthio and pharmaceutical acceptable salts thereof; with the proviso that:

when A is oxygen, B is amino or hydrocarbylamino, E and G are hydrogen, then F is not amino.

According to a further aspect of the present invention, novel adenosine kinase inhibitors are provided that comprise dimeric compounds of the formula:

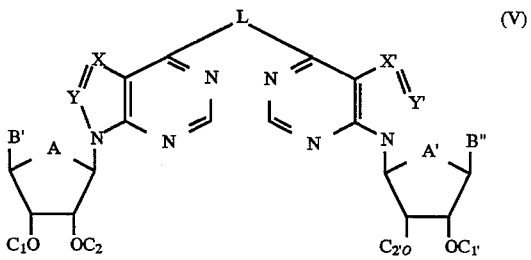

(V)

wherein (a) A and A' are independently oxygen, methylene or sulfur;

(b) B' and B" are independently —(CH$_2$)$_n$B wherein n is independently 1, 2, 3 or 4 and B is independently hydrogen, hydroxy, alkyl, alkoxy, amino, alkylamino, acylamino, hydrocarbyloxycarbonylamino, mercapto, alkylthio, azido, or either or both of B' or B" is independently alkenyl or alkynyl;

(c) C$_1$ and C$_{1'}$ and C$_2$ and C$_{2'}$ are each independently hydrogen, acyl, hydrocarbyloxycarbonyl, or C$_1$ and C$_2$ or C$_{1'}$ and C$_{2'}$ taken together form a 5-membered ring wherein C$_1$ or C$_{1'}$ is a single bond to C$_2$ or C$_{2'}$ and C$_2$ or C$_{2'}$ is carbonyl or α-alkoxyalkylidene;

(d) X and X' are each independently —C(—D)= or —N=; and Y and Y' are each independently —N= or —C(—E)=, provided that either of X and Y or X' and Y' are not both —N=;

(e) D is independently hydrogen, halogen, alkyl, aryl, aralkyl, alkenyl, alkynyl, haloalkyl, cyano, cyanoalkyl, acyl, carboxamido, a carboxylic acid or corresponding carboxylic acid ester group, alkoxy, aryloxy, aralkyloxy, alkylthio, arylthio, aralkylthio, amino, alkylamino, arylamino, aralkylamino acylamino or nitro;

(f) E is independently hydrogen, halogen, alkyl, or alkylthio;

(g) L is an optionally substituted piperazinyl divalent radical or —NH(ALKL)NH— wherein ALKL is a divalent alkylene radical of 2 to 24 carbon atoms; and (h) G and G' are each independently hydrogen, halogen, lower alkyl, lower alkoxy, or lower alkoxy; or pharmaceutically acceptable salts thereof; with the proviso that if B is OH, then X and X' are not both —N=.

In general, preferred are compounds where G is hydrogen, halogen, alkyl or alkylthio. Especially preferred G groups include hydrogen. Preferred C$_1$ and C$_2$ groups include hydrogen and acetyl.

Preferred E groups include hydrogen or halogen, especially preferred are compounds where E is hydrogen.

Preferred are compounds where A is oxygen.

Preferred are compounds where D is hydrogen, halogen, alkyl, aryl, aralkyl, alkenyl or alkynyl, cyano, cyanoalkyl, alkoxy, aryloxy, aralkoxy, alkylthio, arylthio, aralkylthio, amino, alkylamino, arylamino, aralkylamino, carboxamido, or hydrocarbyloxycarbonyl. Especially preferred D groups include hydrogen, halogen, alkyl, aryl, aralkyl, cyano, alkoxy, aryloxy, aralkoxy, alkenyl or alkynyl, more preferably hydrogen, halogen, aryl, cyano, alkoxy or aryloxy. A particularly preferred group of compounds include those wherein D is hydrogen, halogen or aryl. According to one preferred aspect, D is aryl such as heterocyclic aryl or monocyclic carbocyclic aryl, such as optionally substituted phenyl.

Preferred compounds include those where B' is —(CH$_2$)$_n$B, and n is 1 or 2, more preferably n is 1. B may preferably include hydrogen, halogen, alkyl, amino, alkylamino, alkoxy, mercapto, alkylthio, azido or cyano; more preferably B is hydrogen, halogen, lower alkyl, amino, lower alkylamino, azido or cyano. Particularly preferred B groups include hydrogen, amino or azido. Also preferred are compounds wherein B' is vinyl, ethynyl, or propargyl.

Preferred F groups include halogen, amino, alkylamino, arylamino, aralkylamino, alkylthio, arylthio, alkyl, aryl or aralkyl, more preferably amino or arylamino. Especially, preferred F groups include optionally substituted anilino.

A. Preferred Compounds

The compounds of the present invention contain asymmetric carbon atoms and hence can exist as stereoisomers, both enantiomers and diastereomers. The individual preferred stereoisomers and mixtures thereof are considered to fall within the scope of the present invention. The compounds described by Formula I contain a 5-modified 1-β-D-ribofuranosyl group and that isomer comprises a particularly preferred diastereomeric and enantiomeric form for compounds of the present invention. Aptly, the synthetic examples cited herein provide the most preferred isomer. It is evident that in addition to the sugar moiety, additional asymmetric carbons may be present in compounds of Formula I, being present in moieties B', $C_1$ or $C_2$ or the substituted heterocyclic purine, pyrrolo[2,3-d]pyrimidine or pyrazolo[3,4-d]pyrimidine ring. In this event, both of the resulting diastereomers are considered to fall within the scope of the present invention.

It is noted that compounds of Formula I where B is hydroxy (i.e. a 5'-hydroxyl moiety) are in many cases potent inhibitors of adenosine kinase. The use of compounds having Formula I wherein B' replaced by —$CH_2OH$, as adenosine kinase inhibitors are included in the scope of this invention. However, since some of these compounds may be phosphorylated in vivo and since the resulting 5'-phosphates may be toxic, mutagenic or teratogenic, 5'-hydroxy compounds which can serve as substrates for phosphorylation enzymes may not comprise preferred compounds for clinical or therapeutic use. An important aspect of the novel compounds of the present invention is that these preferred compounds are either non-phosphorylatable at the 5' position or are not substrates of enzymes that lead to phosphorylation.

(i) Preferred Pyrazolo[3,4-d]pyrimidines

Preferred adenosine kinase inhibitor compounds of the present invention include certain pyrazolo[3,4-d]pyrimidine compounds of Formulas I and II.

Preferred pyrazolo[3,4-d]pyrimidine compounds of Formula I include those where G is hydrogen and A is oxygen. Preferred D groups include hydrogen, alkyl, aryl, aralkyl, cyano, alkoxy, aryloxy, aralkoxy, alkenyl or alkynyl, more preferably hydrogen, halogen, aryl, cyano, alkoxy or aryloxy, more particularly hydrogen, halogen or aryl. An especially preferred group of compounds includes those where D is aryl, especially heterocyclic aryl or monocyclic carbocyclic aryl, more preferably optionally substituted phenyl. Preferred B' groups include —$(CH_2)_n$B wherein B is hydrogen, halogen, alkyl, amino, alkylamino, alkoxy, mercapto, alkylthio, azido or cyano; more preferably B is hydrogen, halogen, lower alkyl, amino, lower alkylamino, azido or cyano. Particularly preferred B groups include hydrogen, amino or azido. Preferably, n is 1 or 2, more preferably 1. Other preferred B' groups include vinyl and ethynyl. Preferred are compounds of Formula I wherein F is halogen, amino, alkylamino, arylamino, aralkylamino, alkylthio, arylthio, alkyl, aryl or aralkyl, more preferably amino or arylamino. Certain preferred compounds include F groups which comprise optionally substituted anilino.

Examples of preferred pyrazolo[3,4-d]pyrimidine compounds include those noted as GP-1-515, GP-1-547, GP-1-560, GP-1-665, GP-1-666 GP-1-667, GP-1-695, GP-1-704, and GP-1-792.

Preferred pyrazolo[3,4-d]pyrimidine compounds of Formula II include those where G is hydrogen and A is oxygen. Preferred D groups include aryl. Preferred aryl groups include heterocyclic carbocyclic aryl groups, especially optionally substituted phenyl. Preferred F groups include halogen, amino, alkylamino, arylamino, aralkylamino, alkylthio, arylthio, alkyl, aryl, or aralkyl, more preferably amino or arylamino. Certain preferred compounds of Formula II may include F groups which comprise optionally substituted anilino groups.

(ii) Preferred Pyrrolo[2,3-d]pyrimidines

Preferred adenosine kinase compounds of the present invention include pyrrolo[2,3-d]pyrimidine compounds of Formulas I and II.

Preferred pyrrolo[2,3-d]pyrimidine compounds of Formula I include those wherein G is hydrogen. Preferred are compounds wherein E is hydrogen or halogen; more preferably E is hydrogen. Preferred are compounds where A is oxygen. Preferred compounds include those where D is hydrogen, halogen, alkyl, aryl, aralkyl, cyano, alkenyl or alkynyl, more preferably hydrogen, halogen or aryl. An especially preferred group of compounds includes those where D is aryl, especially heterocyclic aryl or monocyclic carbocyclic aryl, especially optionally substituted phenyl. Preferred B' groups include —$(CH_2)_n$B wherein n is 1 or 2, preferably 1. Preferably, B is hydrogen, halogen, alkyl, amino, alkylamino, alkoxy, mercapto, alkylthio, azido or cyano, more preferably B is hydrogen, halogen, lower alkyl, amino, lower alkylamino, lower alkoxy, lower alkylthio, or azido, more particularly hydrogen, lower alkyl, amino, lower alkylamino, or azido. Especially preferred B groups include hydrogen, amino or azido. Other preferred B' groups include vinyl and ethynyl. Preferred pyrrolo[2,3-d]pyrimidine compounds of Formula I include those wherein F is halogen, amino, alkylamino, arylamino, aralkylamino, alkylthio, aralkylthio, alkyl, aryl or aralkyl, more preferably amino or arylamino. Certain preferred compounds include F groups which comprise optionally substituted anilino. Examples of preferred pyrrolo[2,3-d]pyrimidine compounds include those noted as GP-1-448, GP-1-606, GP-1-608, GP-1-639, GP-1-683, GP-1-684, GP-1-691, GP-1-711, GP-1-714, and GP-1-718.

Preferred pyrrolo[2,3-d]pyrimidines of Formula II include those where G is hydrogen and A is oxygen. Preferably E is hydrogen or halogen, more preferably hydrogen. Preferred D groups include aryl. Preferred aryl groups include heterocyclic aryl groups and monocyclic carbocyclic aryl groups, especially optionally substituted phenyl. Preferred heterocyclic aryl groups include 2-furanyl, 2-thienyl and 3-thienyl.

(iii) Preferred Purines

Preferred purine compounds include those where G is hydrogen, halogen, lower alkyl or lower alkylthio, more preferably hydrogen. Preferred are compounds wherein A is oxygen. Preferred E groups include hydrogen, halogen or alkylthio. Preferred are compounds wherein B is amino. Preferred F groups include halogen, amino, alkylamino, arylamino, aralkylamino, alkylthio, arylthio, alkyl, aryl or aralkyl, more preferably amino or arylamino.

(iv) Preferred Dimer Compounds

Preferred dimeric compounds include those which comprise dimers of the above-described pyrazolo[3,4-d] pyrimidines, the pyrrolo[2,3-d]-pyrimidines and purines. These dimers may comprise monomeric units which are the same or different.

SYNTHESIS OF PREFERRED COMPOUNDS

A. General Synthetic Methods

This invention is also directed to processes for preparing compounds of Formula I. Disclosed herein are general synthetic routes for preparing variously substituted purine nucleosides or pyrrolo[2,3-d]pyrimidine nucleosides, including a novel and improved synthesis of 5'-deoxy-5-iodotubercidin; and pyrazolo[3,4-d]pyrimidine nucleosides of the present invention.

Figure 3:
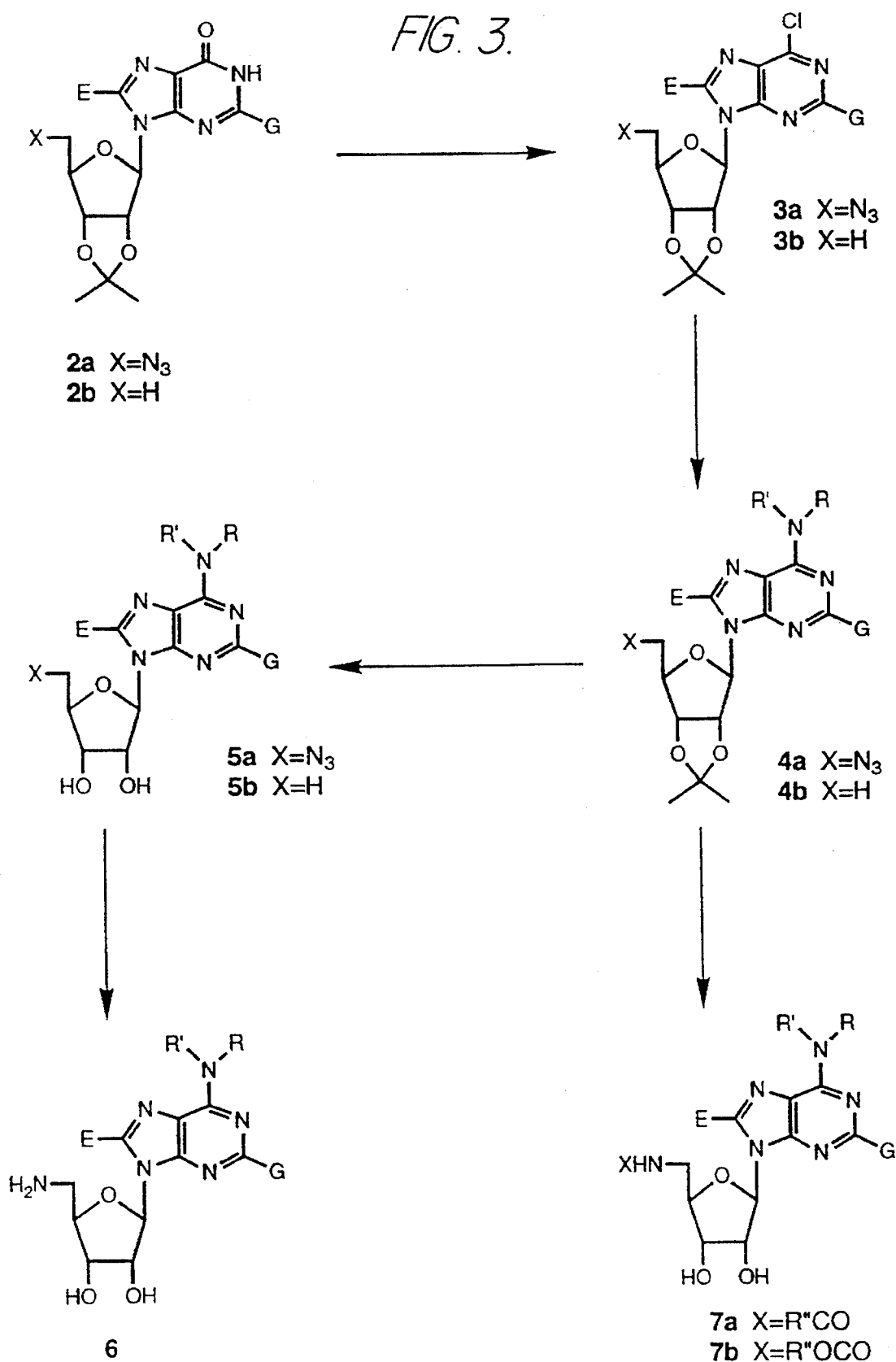
FIGS. 3 to 7 depict reaction schemes for preparing certain of these adenosine kinase inhibitors.

A process for preparing 5'-azido, 5'-amino and 5'-deoxy analogs of 6- substituted-amino purine ribosides is depicted in FIG. 3. The protected azide (2a), prepared from 2',3'-O-isopropylideneinosine, is activated for nucleophilic attack at position six by chlorination with thionyl chloride/dimethylformamide. Other standard reagents may also be used to activate position six of compound (2) such as thionyl bromide, phosphorous oxychloride, triphenylphosphine dibromide-thiophenol-potassium permanganate or hexamethyldisilazane-ammonium sulfate. The chloride (3) or other activated intermediate (Br, RSO$_2$, R$_3$SiO, etc.) is then reacted with ammonia or an appropriate amine such as aniline, piperazine or indoline in solvents such as water, alcohols, THF and the like. The resulting protected azide (4a) is deblocked using an aqueous acid such as 50% formic acid, to provide the 6-substituted-amino 5'-azido-5'-deoxyadenosine (5a). Reduction of the azide (5a) to the amine (6) is effected by catalytic hydrogenation with a catalyst such as platinum oxide, palladium on carbon and the like. For molecules containing other functional groups sensitive to hydrogenation, triphenylphosphine is used to selectively reduce the azide moiety to the amine. To prepare the N-acylamino (7a) and hydrocarbyloxycarbonylamino (7b) compounds, the azide (4a) is reduced to the amine and treated with an acyl anhydride or acyl chloride or alkyl chloroformate and deblocked to give (7a) or (7b) respectively. Analogous processes are used to prepare the 2- and 8-substituted analogs beginning with appropriately substituted intermediates. An alternative synthesis of 5'-amino and 5'-hydrocarbylamino compounds comprises deblocking a 2',3'-isopropylidene-5'-tosylate with aqueous acid and then reacting the deblocked tosylate with ammonia or a lower hydrocarbylamine. Further description of these procedures is set forth in the Examples.

A similar process is used to prepare 5'-deoxy purine nucleosides. The appropriately substituted 5'-deoxy-2',3'-O-isopropylideneinosine (2b) is chlorinated or activated using other reagents described above, aminated to (4b) and subsequently deblocked to afford the 5'-deoxy nucleoside (5b).

Figure 5:
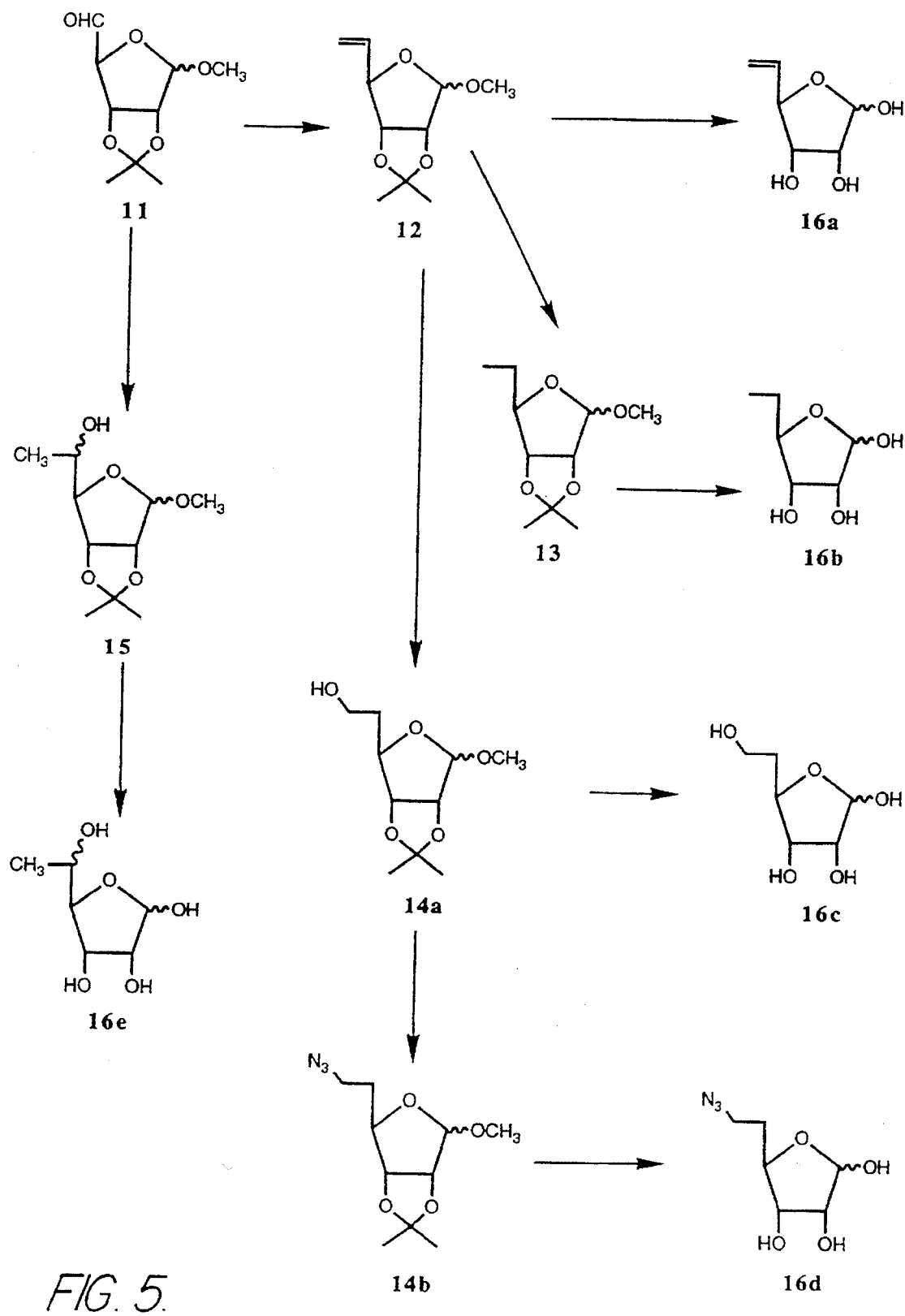
Figure 6:
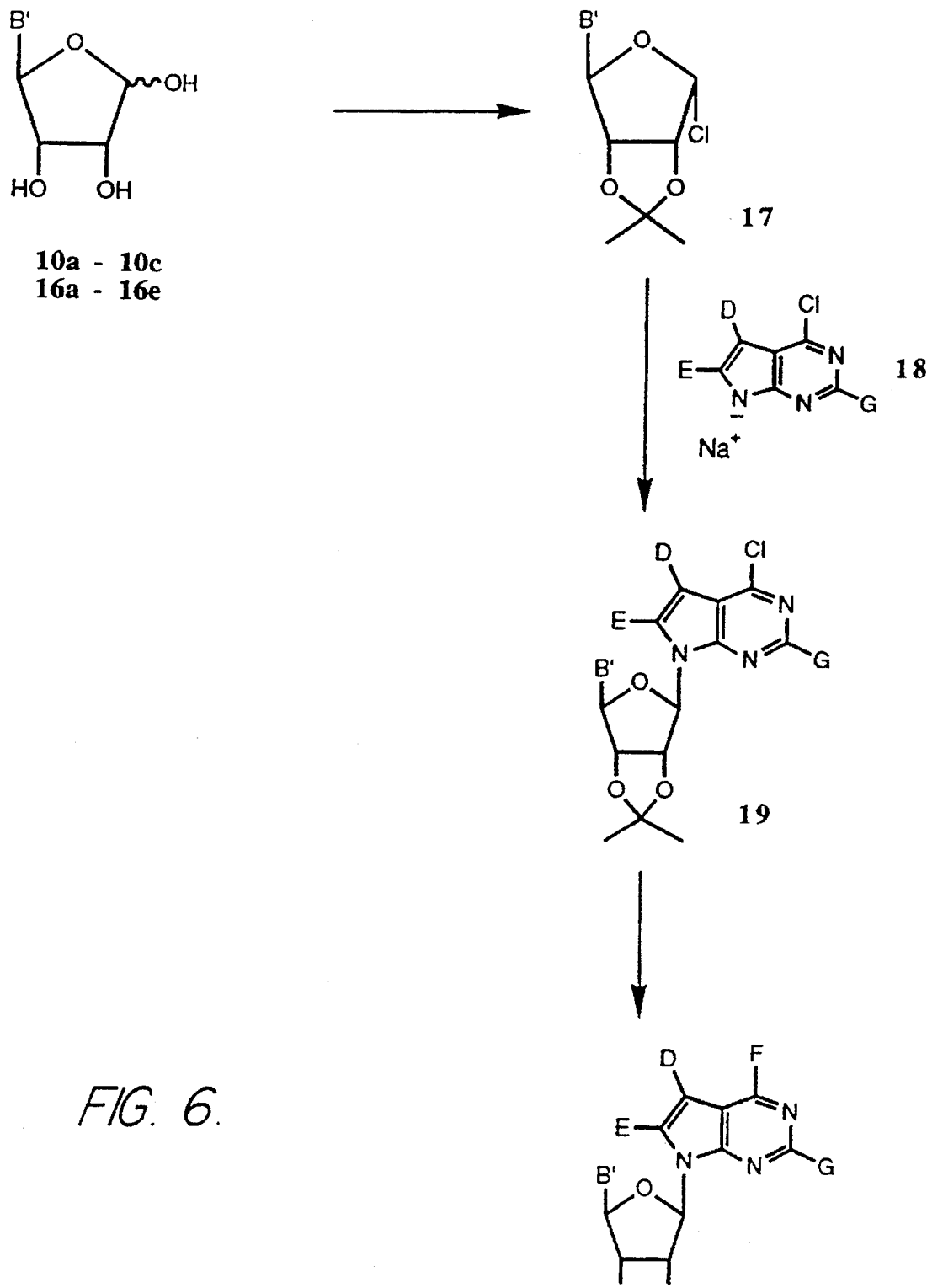

The overall process for preparing 5'-modified pyrrolo[2,3-d]pyrimidine riboside compounds of Formula I, is depicted in FIG. 6. A key step comprises the sodium salt glycosylation method (K. Ramasamy et al., *Tetrahedron Letters*, 1987, 28:5107) using the anion of a substituted 4-chloropyrrolo[2,3-d]pyrimidine (18) and 1-chloro-2,3-O-isopropylidene-5-O-tert-butyldimethylsilyl-α-D-ribofuranoside (17). This method is also suitable for direct preparation of ribofuranosides wherein the 5-hydroxy group has been replaced with substituents such as hydrogen or azido or extended with additional carbons (FIG. 5). The azide sugars further provide for facile synthesis of 5'-amino nucleosides by reductions of the azide function after ribosylation. An alternative to the sodium salt glycosylation method is a solid-liquid phase transfer reaction using the same substrates and potassium hydroxide in place of sodium hydride as described by Rosemeyer H., and Seela, F, *Helvetica Chimica Acta*, 1988, 71:1573.

Figure 4:
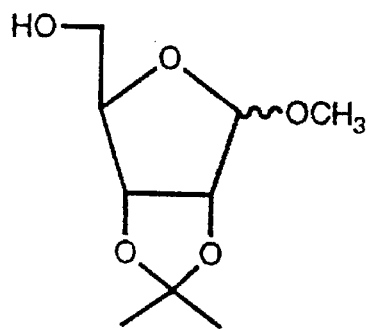
Figure 4:
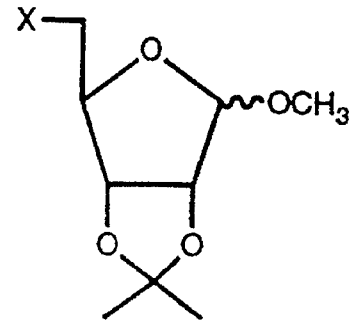
Figure 4:
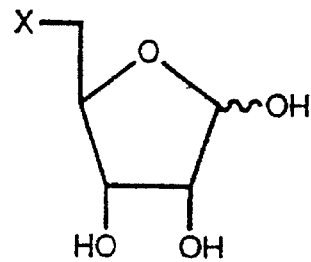

Preparation of the 5-substituted ribose analogs and homologs is outlined in FIGS. 4 and 5. The 5-substituted-5-deoxy ribose analogs (10) are prepared by tosylation of the protected ribose (8), displacement of the tosylate by appropriate nucleophiles and subsequent deblocking (Synder, J.; Serianni, A.; *Carbohydrate Res.*, 1987, 163:169). The ribose homologs (FIG. 5) are prepared by oxidation of the protected ribose (8) to the aldehyde (11) (Moorman, A.; Borchaedt, R.; *Nucleic Acid Chemistry-Part III*, Townsend, L.; Tipson, R.; John Wiley & Sons, 1986). The aldehyde is homologated via the appropriate Wittig reagent to give the key intermediate protected vinyl sugar (12). The protected intermediate is deblocked to give the vinyl ribose homolog (16a) or reduced to (13) and then deblocked to give the saturated deoxy analog (16b). Alternatively, the vinylated intermediate (12) is hydroborated and oxidized affording the protected homologous ribose (14a) which is deblocked to the ribose homolog or converted to the azide (14b) via tosylation and displacement with azide. Deblocking of (14b) then affords the homologous azido ribose (16d). The protected 5-aldehyde (11) was also methylated to ultimately afford 6-deoxy-D-allofuranose (16e). The various 5- substituted riboses are then converted to the corresponding 2,3-O-isopropylidine ketals (FIG. 6) which are chlorinated stereoselectively to 5-modified 1-chloro-α-D-ribofuranosides (17) using carbon tetrachloride and hexamethylphosphorous triamide (Wilcox, C.; Otaski, R.; *Tetrahedron Lett.*, 1986, 27:1011).

The preparation of various substituted 4-chloro-pyrrolo[2,3-d]pyrimidines is described in the Examples. The initial products from the ribosylation reactions, ribosyl protected 5-substituted-4-chloropyrrolo[2,3-d]pyrimidine nucleosides and the corresponding deblocked compounds are versatile intermediates and comprise an aspect of the present invention. As examples, the 4-chloro substituent of (19) can be displaced by sulfur (such as thiourea or mercaptide anions) leading to thionated and hydrocarbylthio compounds. More importantly, displacement of the 4-chloro substituent by ammonia or amines leads to 4-amino- and 4-arylaminopyrrolo[2,3-d]pyrimidine nucleosides. As further example, and an aspect of the present invention, an improved synthesis of the adenosine kinase inhibitor, 5'-deoxy-5-iodotubercidin is described. According to this novel method, coupling of the sodium salt of 4-chloro-5-iodopyrrolo[2,3-d]pyrimidine with 1-chloro-5-deoxy-2,3-isopropylidene-α-D-ribofuranoside (17, B'=CH$_3$) in acetonitrile gives the protected 4-chloro compound. Amination of this product with ammonia, followed by deblocking affords 5'-deoxy-5-iodotubercidin.

Especially preferred intermediates are protected pyrrolo[2,3-d]pyrimidine nucleosides having a 4-chloro and a 5-iodo or bromo substituent.

Another aspect of the present invention is directed to the use of arylboronic acids to prepare 4- and 5-arylated pyrrolo[2,3-d]pyrimidine bases and nucleosides from the corresponding 4- and 5-halogenated compounds. Thus, a halogenated nucleoside such as (19) or the corresponding base was heated with an arylboronic acid and a palladium-phosphine catalyst such as palladium tetrakis (triphenylphosphine) to prepare the analogous arylated compound by displacement of halogen. Various 4- and 5-arylated pyrrolo[2,3-d]pyrimidines also can be prepared using arylstannyl compounds in place of the arylboronic acids (Flynn, B.; Macolino, B.; Crisp, G. *Nucleosides & Nucleotides*, 1991, 10:763). Synthesis of 5-arylpyrrolo[2,3-d]pyrimidines can also be effected by condensation of arylamino ketones and malononitrile to arylated pyrroles and subsequent ring closure to 5-arylpyrrolo[2,3-d] pyrimidines. (Taylor, E.; Hendess, R., *J. Am. Chem. Soc.*, 1965, 87:1995).

The various above-mentioned products of ribosylation reactions may be deblocked at appropriate points with aqueous acids such as 50% formic acid or trifluoroacetic acid. Preparation of 5'-amino compounds consists of reducing an appropriate azide. The 5'-amides and urethanes are prepared analogously to those described previously for purine analogs. Further description of these procedures is set forth in the Examples.

Figure 7:
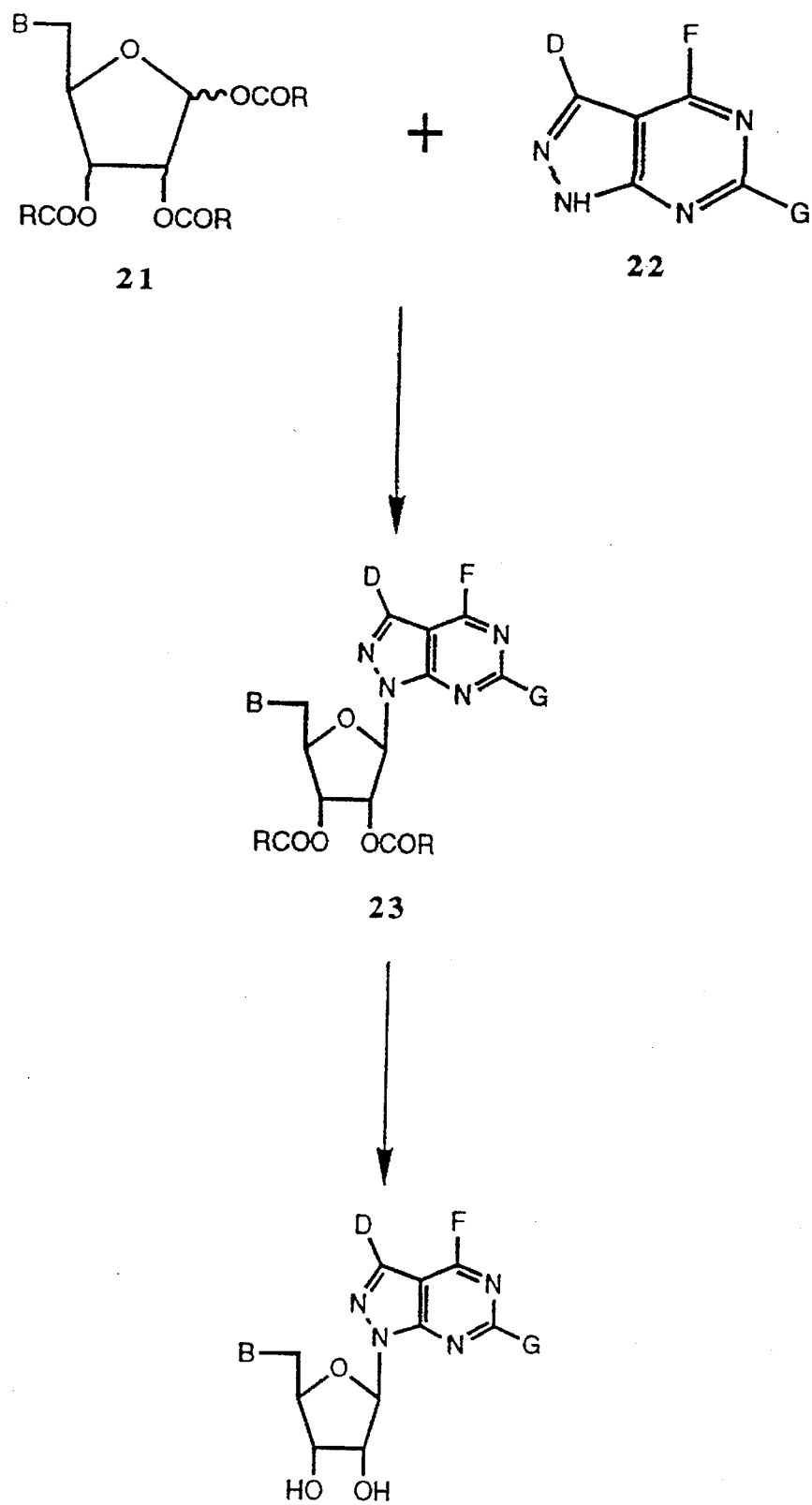

Still another aspect of this invention is the preparation of 5'-substituted pyrazolo[3,4-d]pyrimidine ribosides of Formula I as depicted in FIG. 7. Accordingly, a substituted pyrazolo[3,4-d]pyrimidine is ribosylated with an esterified 5-hydroxy, 5-azido or 5-deoxyribofuranoside in the presence of a Lewis acid such as boron trifluoride (Cottam, H., Petrie, C.; McKernan, P.; Goebel, R.; Dalley, N.; Davidson, R.; Robins, R.; Revankar, G.; *J. Med. Chem.,* 1984, 27:1120). The 5-substituted sugar is prepared by esterification of the deblocked sugar (10a) to (10c) or (16a) to (16e) (See FIG. 6). Suitable esters include the acetate, benzoate, toluate, anisoate and the like. The substituted pyrazolo[3,4-d] pyrimidine base (22) may be prepared by a variety of procedures as illustrated in the Examples. Two general routes to the compounds of the present invention are described below.

The first general route comprises coupling an esterified ribose (21), prepared from (10) or (16), with a 3-substituted pyrazolo[3,4-d]pyrimidin-4-one. After ribosylation the pyrimidone riboside (24a) may be activated by chlorination with thionyl chloride/dimethylformamide or other reagents previously described and then reacted with ammonia or an amine to provide a variety of substituted 5'-modified $N^4$-substituted-amino-pyrazolo[3,4-d]pyrimidine nucleosides (24b). Examples of this aspect of the invention, 3-iodopyrazolo[3,4-d]pyrimidone nucleosides, are prepared by nonaqueous diazotization-iodination of the 3-amino compounds using a nitrite ester such as isoamyl nitrite and methylene iodide. Previous attempts to diazotize the 3-aminopyrazolo[3,4-d]pyrimidones using aqueous nitrous acid gave only N-nitrosated pyrazolo[3,4-d]pyrimidin-3,4-diones (Cottam, H.; Petrie, C.; McKernan, P.; Goebel, R.; Dalley, N.; Davidson, R.; Robins, R.; Revankar, G.; , *J. Med. Chem.,* 1984, 27:1119). Further modifications of (23) or (24) include reduction of the 5'-azido moiety to afford the 5'-amino compounds or the 5'-amides and urethanes as described in FIG. 7. Ester prodrugs ($C_1$ and $C_2$) of various 5'-amino nucleosides are prepared by reduction of the 5'-azide esters (23) using previously described reagents.

Various C-4 alkylated pyrazolo[3,4-d]pyrimidine nucleosides are prepared by reaction of the above mentioned suitably protected 4-chloropyrazolo[3,4-d]pyrimidine nucleosides with carbanion nucleophiles. A specific catalyst for this alkylation reaction was found to be trimethylamine; these reactions either do not occur or proceed very slowly and in poor yield in the absence of trimethylamine. Suitable carbanions include those derived from diethyl malonate, ethyl cyanoacetate, malononitrile, nitromethane, cyanide salts and the like. This procedure is also used to prepare C-6 alkylated purine ribosides. The initial C-alkylated products were deblocked and optionally further modified by hydrolysis and decarboxylation to afford the desired products.

An alternative process for synthesis of 5'-azido- and 5'-amino-5'-deoxypyrazolo[3,4-d]pyrimidine ribosides is also described. Accordingly, a substituted allopurinol riboside (24a) is protected by conversion to the 2',3'-isopropylidene derivative, tosylated and reacted with sodium azide in DMSO or DMF to form the azide. Activation of position four by chlorination with thionyl chloride/ dimethylformamide or other reagents as described, followed by displacement of the activating group by ammonia or an amine results in a protected 5'-azido-5'-deoxy riboside. The azide is deblocked to afford (24b, B=$N_3$) and subsequently reduced to the 5'-amino riboside using the previously described procedures.

The second general route for preparation of substituted pyrazolo[3,4-d]pyrimidine nucleosides comprises coupling the esterified ribose (21) with various substituted 4-amino or 4-hydrocarbylaminopyrazolo[3,4-d]pyrimidines. The resulting products are then further modified or deblocked to afford the desired compounds. The utility of this procedure is demonstrated in the Examples, by the preparation of 3-phenyl-4-(phenylamino)pyrazolo[3,4-d]pyrimidine 5'-modified ribosides from 3-phenyl-4-(phenylamino) pyrazolo[3,4-d]pyrimidine and various 5'-modified sugars. In another aspect of the present invention, halogenated pyrazolo[3,4]pyrimidine ribosides can be arylated using arylboronic acids and palladium catalysts as described for the pyrrolo[2,3-d]pyrimidines. Alternatively, the base can be boronated and then coupled with an aryl halide. Further description of these procedures is set forth in the Examples.

B. Preferred Methods of Synthesis

According to another aspect of the present invention, certain preferred methods of preparing the adenosine kinase inhibiting compounds of Formula I are provided.

One preferred method of the present invention is a novel procedure for preparing C-6 alkylated purine nucleosides and C-4 alkylated pyrazolo[3,4-d]pyrimidine nucleosides from the 6-chloropurine and 4-chloropyrazolo[3,4-d] pyrimidine nucleosides, respectively, using various carbanions (enolates, cyanide anion, etc.) and trimethylamine as a specific catalyst. Previous methodology for C-alkylation of 6-chloropurines consisted of a multistep route involving alkylthiolation and oxidation to a sulfone followed by nucleophilic displacement with a carbanion (Yame, A.; Matsuda, A.; Veda, T.; *Chem. Pharm. Bull. (Jap.),* 1980, 28:150). This multistep route can be accomplished in one step using the specific catalyst trimethylamine which reacts to form a quaternary salt and in turn is displaced by a carbanion in situ, regenerating trimethylamine. The reactions are specifically catalyzed by unhindered trialkylamines.

Another preferred method of the present invention is a process for preparing arylated bases and nucleosides by reaction of a halogenated pyrrolo[2,3-d]pyrimidine or pyrazolo[3,4-d]pyrimidine with an aryl boronic acid in the presence of a palladium-phosphine catalyst. In this process, the halogen atom of a brominated or preferably, iodinated pyrrolo[2,3-d]pyrimidine or pyrazolo[3,4-d]pyrimidine base or nucleoside, is replaced by an aryl moiety such as phenyl, substituted phenyl or a heteroaryl moiety such as furanyl. A catalyst consisting of a metal such as palladium, complexed to an arylphosphine such as triphenylphosphine must be present as well as a base such as sodium carbonate. The resulting arylated nucleosides are important examples of the present invention and this method is shorter and more versatile than alternative syntheses of arylated nucleosides.

Still another preferred method of the present invention is a process for preparing the previously unknown 3-iodo- and 3-chloropyrazolo[3,4-d]pyrimidine nucleoside by nonaqueous diazotization of 3-aminopyrazolo[3,4-d]pyrimidine nucleosides. According to this invention, a suitably substituted 3-aminopyrazolo[3,4-d]pyrimidine nucleoside is diazotized by heating with an alkyl nitrite such as isoamyl nitrite in the presence of an iodine source (such as methylene iodide) resulting in replacement of the 3-amino moiety with an iodine atom. Alternatively, methylene iodide can be replaced by a chlorine source such as carbon tetrachloride resulting in replacement of the amino moiety by a chlorine atom. A previously reported attempt to effect replacement of the amino moiety in a 3-aminopyrazolo[3,4-d]pyrimidine riboside with other moieties using nitrous acid resulted only in replacement of the amino moiety by a hydroxyl group. The resulting 3-chloro- and particularly 3-iodopyrazolo[3, 4-d]pyrimidine nucleoside are an important subject of adenosine kinase inhibitors disclosed in the present invention.

C. Preferred Intermediates

According to a further aspect of the present invention, certain novel intermediates are provided which are useful in the synthesis of the adenosine kinase inhibitors of the present invention.

(i) Intermediates for Pyrrolo[2,3-d]pyrimidines

Certain intermediates useful in the preparation of certain preferred adenosine kinase inhibitors which comprise substituted pyrrolo[2,3-d]pyrimidine nucleosides include compounds of the formula:

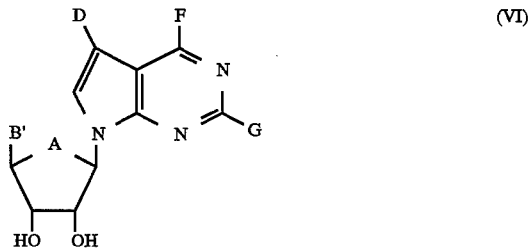

Figure 8:
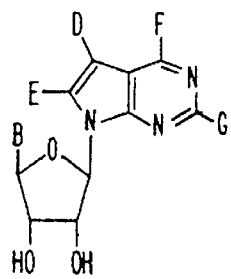
FIG. 8 depicts the structures of certain preferred intermediates useful in the synthesis of adenosine kinase inhibitors.

(VI)

wherein B' is lower alkyl or 1 to 3 carbon atoms optionally substituted with azido or hydroxy, or lower alkenyl of 1 to 3 carbon atoms; D is bromo or iodo, E is hydrogen, F is chloro, mercapto, arylamino and G is hydrogen. Certain especially preferred intermediates are set forth in FIG. 8.

These preferred intermediates include the following compounds:

5-Bromo-4-chloro-7-(5-deoxy-1-β-D-ribofuranosyl)pyrrolo[2,3-d]pyrimidine;

4-Chloro-5-iodo-7-(5-deoxy-1-β-D-ribofuranosyl)pyrrolo-[2,3-d]pyrimidine;

5-Iodo-7-(5-deoxy- 1-β-D-ribofuranosyl)pyrrolo[2,3-d]-pyrimidin-4(3H)-thione;

5-Bromo-4-chloro-7-(5,6-dideoxy-1-β-D-allofuranosyl)pyrrolo[2,3-d]pyrimidine;

4-Chloro-5-iodo-7-(5,6-dideoxy-1-β-D-ribofuranosyl)pyrrolo-[2,3-d]pyrimidine;

5-Bromo-4-chloro-7-(5,6-dideoxy-5,6-didehydro-1-β-D-allofuranosyl)pyrrolo[2,3-d]pyrimidine;

4-Chloro-5-iodo-7-(5,6-dideoxy-5,6-didehydro-1-β-D-allofuranosyl)pyrrolo[2,3-d]pyrimidine;

4-Chloro-5-iodo-7-(5-azido-5-deoxy-1-β-D-ribofuranosyl)pyrrolo[2,3-d]pyrimidine;

5-Bromo-4-chloro-7-(5-azido-5-deoxy-1-β-D-ribofuranosyl)pyrrolo[2,3-d]pyrimidine;

4-Chloro-5-iodo-7-(6-azido-5,6-dideoxy-1-β-D-allofuranosyl)pyrrolo[2,3-d]pyrimidine;

5-Bromo-4-arylamino-7-(5-deoxy-1-β-D-ribofuranosyl)pyrrolo[2,3-d]pyrimidine;

5-Iodo-4-arylamino-7-(5-deoxy-1-β-D-ribofuranosyl)pyrrolo[2,3-d]pyrimidine;

5-Iodo-4-arylamino-7-(1-β-D-ribofuranosyl)pyrrolo[2,3-d]pyrimidine; and

5-Bromo-4-arylamino-7-(1-β-D-ribofuranosyl)pyrrolo[2,3-d]pyrimidine.

In addition to being useful in the preparation of certain preferred adenosine kinase inhibitors, certain of these preferred intermediates exhibit activity as adenosine kinase inhibitors themselves.

(ii) Intermediates for Pyrazolo[3,4-d]pyrimidines

Certain intermediates useful in the preparation of certain preferred adenosine kinase inhibitor compounds comprise substituted pyrazolo[3,4-d]pyrimidines of the formula:

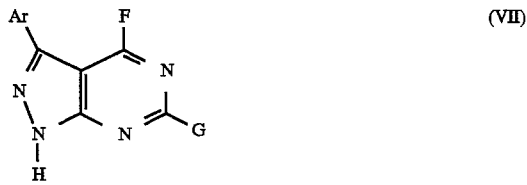

(VII)

wherein Ar is an aryl group and F is halogen, preferably chloro. Preferred aryl groups include heterocyclic aryl groups and monocyclic carbocyclic aryl groups, including optionally substituted phenyl groups. These preferred intermediates include the following compounds:

4-chloro-3-phenylpyrazolo[3,4-d]pyrimidine;

4-chloro-3- (2-thienyl)pyrazolo[3,4-d]pyrimidine;

4-chloro-3-(4-methoxyphenyl)pyrazolo[3,4-d]pyrimidine; and 4-chloro-3-(4-chlorophenyl)pyrazolo[3,4-d]pyrimidine.

UTILITY

The adenosine kinase inhibitors of the present invention may be used in the treatment of a variety of clinical situations where increasing local levels of adenosine are beneficial.

The compounds described herein and other adenosine kinase inhibitors are useful in treating conditions in which inflammatory processes are prevalent such as sepsis, arthritis, osteoarthritis, autoimmune disease, adult respiratory distress syndrome (ARDS), inflammatory bowel disease, necrotizing enterocolitis, chronic obstructive pulmonary disease (COPD), psoriasis, conjunctivitis, iridocyditis, myositis, cerebritis, meningitis, dermitis, renal inflammation, ischemia, reperfusion injury, peripheral vascular disease, atherosclerosis and other inflammatory disorders. Sepsis, septicemia and septic shock, which involve an inflammatory response to a variety of injuries such as burns, pancreatinitis and infection, for example, by gram negative or gram positive bacteria, may be treated with an adenosine kinase inhibitor, such as the adenosine kinase inhibitors described herein.

To assist in understanding the present inventions and especially their properties and utilities, the results of a series of experiments are also included. These experiments demonstrated that a number of compounds described herein were potent inhibitors of a purified cardiac adenosine kinase with $IC_{50}$s of less than 1 µM. Moreover, we have shown that these compounds are specific inhibitors of adenosine kinase with low affinity at the A1 adenosine receptor and no significant adenosine deaminase (ADA) inhibition (Example A). We have demonstrated that a number of these compounds are also inhibitors of adenosine kinase in intact cells (Example B). These compounds include pyrrolo[2,3-d]pyrimidine nucleosides modified at the 5'-position or at other positions such that it is less likely to serve as a substrate for phosphorylation enzymes and that, in contrast to 5-iodotubercidin (GP-1-202), these compounds are unlikely to be phosphorylated at the 5'-position, incorporated into nucleotides or DNA, which may cause toxicity to cells or animals. We have demonstrated that inhibition of the cardiac adenosine kinase was achieved in vivo following systemic administration or, in some cases, oral administration of these compounds.

Selected compounds, such as GP-1-238, were also evaluated to determine the potential for toxic hemodynamic effects or hypothermia associated with administration of adenosine kinase inhibitors. No effects were observed in conscious animals on blood pressure, heart rate or temperature with doses of inhibitor greatly in excess of that required to inhibit the cardiac adenosine kinase (Example C).

In other experimental models, the ability of selected adenosine kinase inhibitors (GP-1-272 and GP-1-456) to inhibit neutrophil adherence to endothelial cells, an inflammatory response mediated at the cellular level was evaluated (Example D). Certain adenosine kinase inhibitors were found to exhibit anti-inflammatory activity in animal models of inflammation. The ability of particular adenosine kinase inhibitors to improve survival in a mouse model of endotoxic shock, both when administered immediately after E. Coli LPS injection (Example E) and when administered prophylactically (Example F), supports the ability of adenosine kinase inhibitors to prevent and treat septic conditions, including endotoxemia and endotoxic shock. The efficacy of adenosine kinase inhibitors in treatment of sepsis is further demonstrated by the ability of particular adenosine kinase inhibitors to improve survival in another model of septic shock (Example G).

The experiments described in Example H show that endotoxic mice treated with an adenosine kinase inhibitor have lower blood levels of tumor necrosis factor alpha (TNF-$\alpha$) compared with placebo treated mice. Cytokines such as TNF-$\alpha$ have been suggested to be involved in many conditions including sepsis and septic shock (Zentella et al., *Progress Clin. Biol. Research* 367:9 (1990); Mathison et al., *J. Clin. Invest.* 81:1925 (1988); Zanetti et al., *J. Immunol.* 148:1890 (1992); Creasey et al., *Circ. Shock* 33:82 (1991); Michie et al., *N. Engl. J. Med.* 318:1481 (1988); Waage et al., *Lancet* 1(8529):355 (1987); Damas et al., *Crit. Care Med.* 17:975 (1989); Girardin et al., *N. Engl. J. Med.* 319:297 (1988)), other severe infectious diseases (Wakabayashi et al., *J. Clin. Invest.* 87:1925 (1991)), adult respiratory distress syndrome (Miltar et al., *Lancet* 2(8665):712 (1989); Rinaldo et al., *Clin. Chest Med.* 11:621 (1990); Ferrai-Baliviera et al., *Arch. Surg.* 124(12):1400 (1989)), acquired immune deficiency syndrome (Folks et al., *PNAS* 86:2336 (1989)), reperfusion injury (Vedder et al., *PNAS* 87:2643 (1990)), and bone resorption diseases (Bertolini et al., *Nature* 319:516 (1986); Johnson et al., *Endocrinology* 124(3):1424 (1989)), among others. Although definite correlation between such conditions and TNF-$\alpha$ has not been established (Eskandari et al., *J. Immunol.* 148:2724 (1992), the results of Example H may indicate a broader therapeutic role for adenosine kinase inhibitors, including the novel compounds disclosed herein.

Additionally Example J describes the efficacy of GP-1-515 in the treatment of endotoxic shock in pigs, as the treated animals did not develop the hypoxemia, hypercapnia and acidosis exhibited in the control animals.

An integral part of the inflammatory response involves an increase of vascular permeability to plasma proteins, herein termed "plasma leakage" or "vascular leakage". Such leakage occurs when there is a change of the barrier properties of the vasculature in a tissue, and may be due to contraction of activated endothelial cells from each other leading to formation of a pore or to partial destruction of the vessel by cells participating in an aggressive immune response. The suppression of vascular leakage by adenosine kinase inhibition is described in Example K. Therefore methods of the present invention may be useful in the treatment of conditions in which vascular leakage is present such as in inhalation injury, the treatment of burns both locally at the injury site and in other organs such as lung (ARDS) and gut, or other edema induced by sepsis, burns or trauma.

Additional support for the use of adenosine kinase inhibitors in burn treatment is presented in Example L. Bacterial infection is a common occurrence during burn recovery. In a burn model, the use of GP-1-515 was shown to significantly reduce bacterial translocation after a severe burn or pancreatitis.

FORMULATIONS

Compounds of the invention are administered to the affected tissue at the rate of from 0.01 to 200 nmole/min/kg, preferably from 1 to 20 nmol/min/kg. Such rates are easily maintained when these compounds are intravenously administered as discussed below. When other methods are used (e.g., oral administration), use of time-release preparations to control the rate of release of the active ingredient may be preferred. These compounds are administered in a dose of about 1 mg/kg/day to about 20 mg/kg/day, preferably from about 3 mg/kg/day to about 8 mg/kg/day and most preferably about 5 mg/kg/day.

For the purposes of this invention, the compounds of the invention may be administered by a variety of means including orally, parenterally, by inhalation spray, sublingually, topically, or rectally in formulations containing conventional non-toxic pharmaceutically acceptable carriers, adjuvants and vehicles. The term parenteral as used herein includes subcutaneous, intravenous, intramuscular, and intraarterial injections with a variety of infusion techniques. Intraarterial and intravenous injection as used herein includes administration through catheters. Preferred for certain indications are methods of administration which allow rapid access to the tissue or organ being treated, such as intravenous injections for the treatment of myocardial infarction. When an organ outside a body is being treated, perfusion is preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including those from the group consisting of sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium carbonate, sodium carbonate, lactose, calcium phosphate or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethyl celluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadeaethyleneoxycetanol), a condensation product of ethylene oxide with a partial ester derived from a fatty acid and a hexitol anhydride (e.g., polyoxyethylene sorbitan mono-oleate). The aqueous suspension may also contain one or more preservative such as ethyl of n-propyl p-hydroxybenzoate, one or more coloring agent, one or more flavoring agent and one or more sweetening agent, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palpable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 200 μmoles of active material compounded with an appropriate and convenient amount of carrier material which may vary from about 5 to about 95% of the total compositions. It is preferred that pharmaceutical composition be prepared which provides easily measurable amounts for administration. For example, an aqueous solution intended for intravenous infusion should contain from about 20 to about 50 μmoles of the active ingredient per milliliter of solution in order that infusion of a suitable volume at a rate of about 30 mL/hr can occur.

As noted above, formations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach. This is particularly advantageous with the compounds of formula (I) as such compounds are susceptible to acid hydrolysis.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampohs, creams, gels, pastes, foams or spray formulations containing in addition to the ddPN ingredient such carriers as are known in the art to be appropriate.

Formations suitable for parenteral administration include aqueous and non-aqueous isotonic sterile injection solutions which may contain anti-oxidants, buffers, bacteriostats and solutes which render the formation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, or an appropriate fraction thereof, of an adenosine kinase inhibitor compound.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Examples of use of the method of the invention includes the following. It will be understood that these examples are exemplary and that the method of the invention is not limited solely to these examples.

The method may be used following thrombolysis for coronary occlusion. The compound would be given as a sterile injectable preparation with water or isotonic sodium chloride as the solvent. The solution can be administered intravenously or directly into the coronary artery at the time of left heart catheterization or into a carotid artery. The rate of administration could vary from 1 to 20 nmole/min/kg with, for example, an infusion volume of 30 mL/hr. Duration of therapy would typically be about 96 hours.

Capsules comprising adenosine kinase inhibitors suitable for oral administration according to the methods of the present invention may be prepared as follows: (1) for a 10,000 capsule preparation: 1500 g of adenosine kinase inhibitor is blended with other ingredients (as described above) and filled into capsules which are suitable for administration depending on dose, from about 4 capsules per day (1 per 6 hours) to about 8 capsules per day (2 capsules per 6 hours), to an adult human.

The compounds of this invention and their preparation can be understood further by the examples which illustrate some of the processes by which these compounds are prepared. These examples should not however be construed as specifically limiting the invention and variations of the invention, now known or later developed, are considered to fall within the scope of the present invention as hereinafter claimed.

EXAMPLES

EXAMPLE 1

Preparation of 5'-Azido-5'-deoxy-2', 3'-O-(1-methylethylidene) inosine

This material was prepared by tosylation of 2', 3'-(1-methylethylidene)inosine and subsequent reaction with sodium azide in DMSO as described by Hampton, A.; *J. Org. Chem.*, 1968, 11:1220.

EXAMPLE 2

Preparation of 9-[5-Azido-5-deoxy-2,3-O-(1-methylethylidene)-1-β-D-ribofuranosyl]-6-chloropurine A solution of the azide (Example 1) (12.01 g) in dry $CH_2Cl_2$ (500 mL) was added, during 1 hr, to a warm solution of $SOCl_2$ (8.1 mL) and DMF (4.05 mL,) in $CH_2Cl_2$ (50 mL). The resulting solution was refluxed for 6 hrs and cooled and added to a cold aqueous solution of $KHCO_3$. The layers were separated and the organic layer was washed with cold aqueous $K_2CO_3$, water(2×), dried and concentrated. The residue was redissolved in $CH_2Cl_2$ and filtered through silica. Evaporation under vacuum gave 11.3 g of the title compound as a pale yellow oil.

EXAMPLE 3

General Procedure for the Preparation of $N^6$-Substituted-5'-azido-5'-deoxy-2',3'-O-(1-methylethylidene)adenosines To a solution of chloride (Example 2) (1 mmole/5 mL) in EtCH or n-BuOH was added amine (1.3 equivalents) and $Et_3N$ (1.8 equivalents). The solution was heated to reflux for 12–24 hours. The mixture was evaporated under vacuum, dissolved in methylene chloride and washed. The organic solution was dried, concentrated and used directly in the next step or chromatographed on silica gel.

EXAMPLE 4 TO 14

General Procedure for the Preparation of $N^6$-Substituted-5'-azido-5'-deoxyadenosines The $N^6$-substituted isopropylidene azide (Example 3) (1.0 g) was dissolved in formic acid (10–20 mL) and diluted with an equal volume of water. After 12–48 hr, the mixture was evaporated under vacuum, coevaporated with water (3×) then EtOH (2×). The residue was crystallized from water, alcohol or mixtures. The compounds in Table I (Examples 4–14) were prepared by this procedure:

TABLE I

| GP-1-# | Example | F | m.p. (°C.) |
|---|---|---|---|
| 266 | 4 | ØNH | 121–126° |
| — | 5 | $CH_3NH$ | 180° (d) |
| 317 | 6 | 4-ClØNH | 209–210° |
| 299 | 7 | ØCH$_2$CH$_2$NH | 144–146° |
| 337 | 8 | N-indolinyl | 157–159° |
| 346 | 9 | 4-(HOCH$_2$CH$_2$)ØNH | 147–151° |
| — | 10 | —NH(CH$_2$)$_{12}$NH-(dimer) | foam |
| 385 | 11 | N-indolyl[1] | 186–188° |
| 391 | 12 | N-(5-bromoindolinyl) | 94–196° |
| 421 | 13 | N-(5-methoxyindolinyl) | 184–185° |
| 557 | 14 | 1,4-piperazinyl | 198–204° |

[1]Prepared from indole and sodium hydride in DMF.

EXAMPLES 15–20

General Procedure for the Preparation of $N^6$-Substituted-5'-amino-5'-deoxyadenosines and Hydrochloride Salts A solution of the azide in EtOH or MeOH containing 10% Pd-C (25–50% weight of azide) was hydrogenated at 25 psi for 4–8 hours. The mixture was filtered, the catalyst rinsed with solvent and the filtrate evaporated. The residue was recrystallized to give the free base or converted to the salt. The hydrochloride salt was prepared by adding the base to ETCH, adding dry ethanolic HCl, warming and then chilling to crystallize out the salt (in some cases $Et_2O$ was added). The compounds below were prepared by this procedure:

TABLE II

| GP-1-# | Example | F | m.p. °C. (salt) |
|---|---|---|---|
| 272 | 15 | $CH_3NH$ | 170–2° ($HCO_2H$) |
| 286 | 16 | ØNH | 169–173° (HCl) |
| 328 | 17 | $ØCH_2CH_2NH$ | 130° (d) (HCl) |
| 345 | 18 | N-indolinyl | 202–203° (HCl) |
| 373 | 19 | —$HN(CH_2)_{12}NH$-(dimer) | 151–153° (HCl) |
| 565 | 20 | 1,4-piperazinyl | 140–145° (HCl) |

EXAMPLE 21

Preparation of 5'-deoxy-2',3'-O-(1-methylethylidene) inosine

A solution of 5'-deoxy-5'-iodo-2',3'-O-(1-methylethylidene)inosine (5.45 g) in 80 mL of methanol containing triethylamine (2 g) and 10% palladium on charcoal (737 mg) was hydrogenated for 2 hr under 50 psi $H_2$. The reaction mixture was filtered, concentrated and allowed to crystallize. The product was dried under vacuum to give 2.45 g (82% yield) of the title compound.

EXAMPLE 22

Preparation of 6-Chloro-9-[5-deoxy-2,3-O-(1-methylethylidene)-1-β-D-ribofuranosyl]purine A solution of the blocked 5'-deoxyinosine (1.4 g, 4.8 mmol), tetraethylammonium chloride (1.9 g, 11.5 mmol), diethylaniline (1.2 mL, 7.2 mmol) and phosphorous oxychloride (3.35 mL, 36 mmol) in $CH_3CN$ (24 mL) was refluxed for 10 minutes then evaporated. The residue was dissolved in $CH_2Cl_2$, washed with water, $KHCO_3$ solution, water and dried. The solution was filtered and evaporated to give 860 mg (65% yield) of title compound as a yellow oil.

EXAMPLE 23

General Procedure for Preparation of $N^6$ substituted 5'-deoxyadenosines

The above identified compounds were prepared using the procedures described in Example 3 and Examples 4–14.

The compound listed in Table III were prepared by this procedure.

TABLE III

| GP-1-# | EXAMPLE | F | m.p. (°C.) |
|---|---|---|---|
| 595 | 23 | 1,4-piperazinyl | 220–225° |

EXAMPLE 24

Preparation of 8-Bromo-2',3'-O-(1-methylidene)-5'-O-(4-methylbenzenesulfonyl)adenosine The above-identified compound may be prepared as described: Ikshara, M.; Kaneko, M.; Sagi, M.; *Tetrahedron*, 1970, 26:5757.

EXAMPLE 25

Preparation of $N^6$-Formyl-8-bromo-2',3'-O-(1-methylethylidene)-5'-O-(4-methylbenzenesulfonyl) adenosine To acetic-formic anhydride (prepared by stirring 25 mL of acetic anhydride and 12.5 mL of formic acid for 15 minutes at 45° C.) at 0° C., was added the tosylate (Example 24) (4.0 g, 7.30 mmol). The solution was allowed to warm to 22° C. and stirred for 48 hours. The reaction mixture was evaporated, chased 2× with toluene and the residue dissolved in $CHCl_3$. Filtration and evaporation of the filtrate and crystallization of the residue from ethanol gave 4.0 g (96%) of the title compound.

EXAMPLE 26

Preparation of 5'-Deoxy-5',8-diazido-2',3'-O-(1-methylethylidene)adenosine

To a 75° C. slurry of $NaN_3$ (2.23 g, 34.3 mmol) in dimethylsulfoxide (35 mL) was added the formyl tosylate (Example 25) (4.00 g, 6.9 mmoles). The reaction temperature was held at 75° C. for one hour then cooled to 25° C. The mixture was poured into stirring $H_2O$ (90 mL) and slurried for ten minutes. The solid was collected by filtration, rinsed with $H_2O$ (3×), cold ethanol, and then dried. The crude product was dissolved in $CHCl_3$, filtered through silica gel and the filtrate evaporated to give the $N^6$-formyl derivative 1.20 g; m.p. 107°–110° C.

The $N^6$-formyl derivative was deformylated by slurrying in MeOH, adding saturated methanolic ammonia (80 mL) and warming until homogenous. After 15 minutes the solution was evaporated, the residue recrystallized from EtOH and dried to give the title compound; 0.900 g (60% yield); m.p. 166°–168° C.

EXAMPLE 27

Preparation of 5'-Deoxy-5',8-diazidoadenosine

The isopropylidene diazide of Example 26 (1.00 g, 3.15 mmol) was deblocked as described under Example 4 and recrystallized from $H_2O$; 760 mg (85% yield); m.p. 128°–130°.

EXAMPLE 28

Preparation of 5'-Deoxy-5'-8-diaminoadenosine Formate

The diazide of Example 27 (0.660 g, 2.0 mmol) was hydrogenated as described under Example 15 and recrystallized from EtOH to give, after drying, 400 mg of the free base (61% yield). This material was further purified by conversion to the formate salt ($HCO_2H/EtOH/Et_2O$); m.p. 98° C.(d).

EXAMPLE 29

Preparation of 5'-Deoxy-5'-formylaminoadenosine

To cold (5° C.) acetic-formic anhydride (10 mL acetic anhydride and 5 mL formic acid) was added 5'-amino-5'-deoxy-2',3'-O-(1-methylethylidene)adenosine (670 mg, 2.0 mmol). The solution was stirred for 24 hours then evaporated, and coevaporated with toluene (2×) then EtOH. The residual foam was dissolved in methanolic ammonia containing $CH_2Cl_2$ and stirred overnight. TLC indicated the initial product was converted to a more polar product. The solution was evaporated, the residue dissolved in $CHCl_3$ with 3% MeOH and filtered through silica. Evaporation of the filtrate gave 520 mg of a white foam. This material (500 mg) was deblocked with $HCO_2H$ as described for Example 4 and recrystallized from $EtOH-H_2O$ to give the title compound: yield 0.35 g (55%); m.p. 212°–213° C.

EXAMPLE 30

Preparation of 6-(N-Indolinyl)-9-[2,3-O-(1-methylethylidene)-1-β-D-ribofuranosyl)]purine A mixture of the isopropylidene of 6-chloropurine riboside (11.5 g, 0.035 mol), indoline (5.13 mL, 0.046 mole) and triethylamine (8.82 mL, 0.063 mole) in n-butanol (60 mL) was stirred and heated to reflux for 24 hours. The reaction was cooled and the solid collected by filtration, rinsed with EtOH and dried to give the title compound: 10.70 g (75% yield); m.p. 119°–125° C.

EXAMPLE 31

Preparation of 6-(N-Indolinyl)-9-[2,3-O-(1-methylethylidene)-5-O-(4-methylbenzenesulfonyl)-1-β-D-ribofuranosyl)]purine To a cold (0° C.) solution of the alcohol (Example 30) (6.0 g, 0.015 mol) in dry pyridine (40 mL) was added with stirring, p-toluenesulfonyl chloride (6.96 g, 0.36 mol). The solution was sealed and stored at 0°–10° C. for 72 hours then poured into cold H$_2$O (30 mL). The solid was collected by filtration and rinsed 3× with H$_2$O. After drying at 25° C. under vacuum, the title compound was obtained: 6.85 g (83% yield); m.p. 195° C. (d).

EXAMPLE 32

Preparation of 6-(N-Indolinyl)-9-[5-O-(4-methylbenzenesulfonyl)-1-β-D-ribofuranosyl)]purine A slurry of the protected tosylate (Example 31) (5.80 g, 10.0 mmole) in hydrochloric acid (23 mL) and EtOH (255 mL) was heated until homogenous then refluxed for 15 minutes. The solution was cooled in an ice bath and neutralized. The solid was collected by filtration, washed with H$_2$O, EtOH then MeOH. After drying, 3.38 g (65% yield) of the title compound were obtained; m.p. 112° C.(d).

EXAMPLE 33

Preparation of 6-(N-Indolinyl)-9-(5-methylamino-5-deoxy-1-β-D-ribofuranosyl)purine Hydrochloride To 40% aqueous methylamine (40 mL) was added the tosylate (Example 32) (2.0 g, 3.8 mmol) and sufficient MeOH to give a clear solution. The solution was stirred for one week then concentrated. The residue was coevaporated 3× with MeOH then recrystallized from MeOH to give the free base, 0.310 g (21% yield). A portion of this material was converted to the hydrochloride salt, m.p. 170°–172°.

EXAMPLE 34

Preparation of 4-Chloro-7H-pyrrolo[2,3-d]pyrimidine

The above-identified compound was prepared as described: Davoll, J.; *J. Chem. Soc.*, 1960, 131.

EXAMPLE 35

Preparation of 5-Bromo-4-chloro-7H-pyrrolo[2,3-d]pyrimidine

The above identified compound was prepared as described: Hinshaw, B.; Gerster, J.; Robins, R.; Townsend, L.; *J. Heterocyclic Chem.*, 1969, 215.

EXAMPLE 36

Preparation of 4-Chloro-5-iodo-7H-pyrrolo[2,3-d]pyrimidine

The above-identified compound was prepared as described: Pudlo, J.; Nassiri, M.; Kern, E.; Wartiny, L.; Drach, J.; Townsend, L.; *J. Med. Chem.*, 1990, 33, 1984.

EXAMPLE 37

Preparation of 4-Chloro-5-methyl-7H-pyrrolo[2,3-d]pyrimidine

The above-identified compounds was prepared as described: Pudlo, J.; Nassir, M.; Kern, E.; Wotring, L.; Drach, J.; Townsend, L.; *J. Med. Chem.*, 1990, 33, 1984.

EXAMPLE 38

Preparation of 4-Chloro-2-methylthio-7H-pyrrolo[2,3-d]pyrimidine

The above-identified compound was prepared as described: Noel, C., Robins, R.; *J. Heterocyclic Chem.*, 1964, 1, 34.

EXAMPLE 39

Preparation of 2-Amino-4-Chloro-7H-pyrrolo[2,3-d]pyrimidine

The above-identified compound was prepared as described: Pudlo, J.; Nassiri, M.; Kern, E.; Wotring, L.; Drach, J.; Townsend, L.; *J. Med. Chem.*, 1990, 33, 1984.

EXAMPLE 40

Preparation of 2-Amino-4-chloro-7H-pyrrolo[2,3-d]pyrimidine

The above-identified compound was prepared as described. Seela, F.; Stiker, H.; Driller, H.; Binding, N.; *Liebigs Ann. Chem.*, 1987, 15.

EXAMPLE 41

Preparation of 4-Chloro-5-methylthio-7H-pyrrolo[2,3-d]pyrimidine

A solution of 5-bromo-4-chloro-7H-pyrrolo[2,3-d]pyrimidine (Example 35) (2.53 g, 10 mmol) in THF (30 mL) was cooled to –78° C. and a solution of n-butyl lithium (12 mL of 2.3M solution, 25 mmol) was added keeping the reaction temperature below –72° C. The reaction mixture was stirred at –78° C. for 45 min, a solution of methyl disulfide (0.95 mL, 10 mmol) in tetrahydrofuran (10 mL) was added over a period of 30 minutes maintaining the temperature below –72° C. The reaction mixture was stirred at –78° C. for 2.5 hours then allowed to warm to room temperature. A saturated solution of ammonium chloride (40 mL) was added to the reaction with stirring. The organic layer was separated, the aqueous layer extracted with ethyl acetate (2×40 mL) and the combined organic extracts were dried, filtered and evaporated to obtain a pale yellow solid which was crystallized from EtOH: yield 1.65 g; (70%) m.p. 166°–167° C.

EXAMPLE 42

Preparation of 4-Chloro-5-cyano-7H-pyrrolo[2,3-d]pyrimidine

N-Butyllithium in hexane (2.31M, 6.1 mL, 14.0 mmol) was added dropwise to a solution of 4-chloro-5-bromopyrrolopyrimidine (Example 35) (1.481 g, 6.37 mmol) in 65 mL THF at –78° C. and the resulting light yellow suspension stirred at this temperature for 1 hour. A cold (–78° C.) solution of p-tolylsulfonylcyanide (2.08 g, 11.5 mmol) in 35 mL THF was added dropwise and stirred at this temperature for 1 hour. Aqueous NH$_4$Cl was added and the resulting solution was diluted with 100 mL CH$_2$Cl$_2$. Washed the organic layer with water, brine, dried and evaporated to provide a tan solid (1.3 g) which appeared to be a 1:1 mixture of the title nitrile and 4-chloropyrrolo- pyrimidine by $^1$H NMR. This material was recrystallized from 25 mL ethanol to provide 435 mg (38%) of the title nitrile as a tan solid: m.p. 300° C.

This compound may also be prepared as described: Tollman et al., *J. Amer. Chem. Soc.*, 1969, 91:2102.

EXAMPLE 43

Preparation of 4-Chloro-5-ethoxycarbonyl-7H-pyrrole[2,3-d]pyrimidine

A solution of 5-bromo-4-chloropyrrolo[2,3-d]pyrimidine (Example 35) (232 mg; 1 mmol) in THF (5 mL) was cooled to −78° C. and a solution of n-butyl lithium (1.3 mL of 2.31M) was added keeping the temperature below −72° C. After stirring the reaction mixture at −78° C. for 45 minutes, a solution of ethyl chloroformate (0.15 mL) in THF (2 mL) was added slowly, maintaining the reaction temperature below −72° C. The reaction mixture was stirred at −78° C. for 2 hours then allowed to warm to room temperature. A saturated solution of NH$_4$Cl (20 mL) was added to the reaction mixture. The organic layer was separated and the aqueous layer was extracted with ethyl acetate (2×25 mL). The combined organic extracts were dried and evaporated to a white solid: yield 210 mg (92%): m.p. 140°–141° C.

EXAMPLE 44

Preparation of 5-O-[(1,1-Dimethylethyl)dimethylsilyl]-2,3-O-(1-methylethylidene)-D-ribofuranose The above-identified compound was prepared as described: H. Rosemeyer, H.; Seela, *Helv. Chim. Acta.*, 1988, 71:1573.

EXAMPLE 45

Preparation of 5-Deoxy-D-ribofuranose

The above-identified compound was prepared as described: Snyder J.; Serianni, A.; *Carbohydrate Research*, 1987, 163:169.

EXAMPLE 46

Preparation of 5-O-Methyl-D-ribofuranose

The above-identified compound was prepared as described: Snyder, J.; Serianni, A.; *Carbohydrate Research*, 1987, 163:169.

EXAMPLE 47

Preparation of 1-O-Methyl-2,3-O-(1-methylethylidene)-5-O-(4-methylbenzenesulfonyl)-D-ribofuranoside The above-identified compound was prepared as described: Snyder, J.; Serianni, A.; *Carbohydrate Research*, 1987, 163:169.

EXAMPLE 48

Preparation of 5-Deoxy-2,3-O-(1-methylethylidene)-D-ribofuranose

5-Deoxy-D-ribofuranose (8 g, 60 mmole) was dissolved in DMF (25 mL) and to the solution was added dimethoxypropane (10 mL) and p-toluenesulfonic acid (150 mg). The reaction was stirred overnight then neutralized with OH$^-$ resin. The mixture was filtered, concentrated and the residue chromatographed on silica gel. Collected like fractions and evaporated to yield 4.1 g (39% yield) of viscous liquid.

EXAMPLE 49

Preparation of 5-O-Methyl-2,3-O-(1-methylethylidene)-D-ribofuranose

To a solution of 5-O-methyl-D-ribofuranose (6.0 g, 36 mmole) in dry DMF (25 mL), 2,2-dimethoxypropane (25 mL) and p-toluenesulfonic acid (250 mg) were added and the solution was stirred at room temperature for 20 hours, evaporated and chromatographed over silica. Collected and evaporated like fractions to give the title compound as an oily product, yield: 5.0 g (68%).

EXAMPLE 50

5-Azido-5-deoxy-1-O-methyl-2,3-O-(1-methylethylidene)-D-ribofuranoside

A mixture of 1-O-methyl-2,3-O-(1-methylethylidene)-5-O-(4-methylbenzenesulfonyl)-D-ribofuranoside (8.0 g, 22 mmole), DMF (40 mL) and NaN$_3$ (4.0 g, 62 mmol) was heated at 80° C. for 12 hours. The solvent was evaporated and the residue chromatographed. The faster moving fractions were pooled and evaporated to obtain 4.8 g (94% yield) of a syrupy product.

EXAMPLE 51

Preparation of 5-Azido-5-deoxy-D-ribofuranose

A solution of 5-azido-5-deoxy-1-O-methyl-2,3-O-(1-methylethylidene)-D-ribofuranoside (4.6 g, 20 mmol) in 0.1% H$_2$SO$_4$ (300 mL) was refluxed for 3 hours. The acid was neutralized with OH$^-$ resin. Filtered and washed the resin with ethanol. The filtrate was evaporated to give a syrupy residue; $^1$H and $^{13}$C NMR confirmed the product identity as a mixture of α and β anomers.

EXAMPLE 52

Preparation of 5-Azido-5-deoxy-2,3-O-(1-methylethylidene)-β-D-ribofuranose

The crude 5-azido-5-deoxyribose (Example 51) was dissolved in DMF (10 mL) and treated with 2,2-dimethoxypropane (10 mL) and p-toluenesulfonic acid (100 mg). The solution was stirred at room temperature for 20 hours then evaporated. The residue was chromatographed. The appropriate fractions were pooled and evaporated to obtain the title compound, yield 2.4 g (56% yield).

EXAMPLE 53

Preparation of 1-O-Methyl-2,3-O-(1-methylethylidene)-D-pentodialdo-1,4-furanoside The above-identified compound was prepared as described: Moorman, A., Borchardt, R.; *Nucleic Acid Chemistry-Part III*, Ed. Towsend, L., Tipson, R.; John Wiley and Sons, N.Y.; 1986, pages 38–41.

EXAMPLE 54

Preparation of 5-Benzoyl-D-allofuranose

The sugar aldehyde from Example 53 (100 mmol) was dissolved in THF and treated with methyl magnesium bromide (100 mmol). After 2 hours of stirring at room temperature, a saturated solution of ammonium chloride in water (180 mL) was added. The organic layer was separated and the aqueous layer was extracted with ether (2×100 mL). The combined organic layers were dried and evaporated to obtain an oily product whose NMR was consistent with methyl-6-deoxy-2,3-isopropylidene-D-allofuranoside. The crude product was dissolved in pyridine (50 mL) and treated with benzoic anhydride (120 mmole). After stirring for 18 hours, methanol (2 mL) was added and the reaction mixture was evaporated. The residue was dissolved in ethyl acetate (300 mL) and washed with water, saturated bicarbonate solution, and brine. The organic layer was dried and evaporated to obtain a glassy product which was purified by chromatography. Identity of the product was confirmed by IR and NMR spectroscopy. The intermediate protected sugar was heated with aqueous sulfuric acid solution (0.01N in water, 300 mL) to 80° C. for 2 hours and neutralized with resin. The aqueous layer was separated and evaporated to obtain the title compound as a sticky mass. The product was confirmed by NMR and used in the next step without further purification.

EXAMPLE 55

Preparation of 5-Benzoyl-6-deoxy-2,3-O-(1-methylethylidene)-D-allofuranose

The benzoylated sugar (Example 54) was dissolved in a mixture of dry DMF (20 mL), 2,2-dimethoxypropane (20 mL) and p-toluenesulfonic acid (200 mg) and stirred at room temperature. After 2 hours the reaction mixture was neutralized by strongly basic ion exchange resin and the resin removed by filtration and washed. The combined washings and filtrate were evaporated and the residue was purified by chromatography. The pure product obtained was a glassy solid.

EXAMPLE 56

Preparation of 5,6-Dideoxy-5,6-didehydro-1-O-methyl-2,3-O-(1-methylethyldene)-D-allofuranoside To a suspension of potassium-tert-butoxide (9.36 g) in ether (300 mL), methyl triphenylphosphonium bromide (29.6 g) was added over a 5 minute period. The yellow colored solution was stirred for 1½ hours then a solution of methyl-2,3-isopropylidene-D-pentodialdo-1,4-furanoside (8.0 g), Example 53, in ether (75 mL) was added over 5 minute period. The reaction mixture was stirred overnight at room temperature. The solid material that formed was removed by filtration and washed repeatedly with ether. The combined washings and filtrate were evaporated and the residue purified by chromatography to obtain 6.5 g of product as an oil; TLC Rf=0.5 (Silica gel, 97:3 hexane: EtOAc).

EXAMPLE 57

Preparation of 5,6-Dideoxy-5,6-didehydro-2,3-O-(1-methylethylidene)-D-allofuranose A mixture of 5,6-dideoxy-5,6 didehydro-1-O-methyl-2,3-O-(1-methylethylidene)-D-allofuranose (Example 56) (2.0 g), and aqueous $H_2SO_4$ (0.1%, 50 mL) was heated to 90° for 3 hours. The pH of the solution was adjusted to 7.5 with 1N NaOH solution, and evaporated to dryness. The residue was evaporated with DMF (2×20 mL) and the resulting semi solid product was slurried in methanol (25 mL). The undissolved solid was removed by filtration and washed with methanol (2×20 mL). The combined washings and the filtrate were evaporated to dryness and the resulting residue was dissolved in a mixture of dry DMF (10 mL), 2,2-dimethoxypropane (6 mL) and p-toluenesulfonic acid (50 mg). After stirring for 2 hours at room temperature the acid was neutralized with ion exchange resin and the resin was removed by filtration. Evaporation of the filtrate gave a product which was purified by chromatography over silica gel.

EXAMPLE 58

Preparation of 5,6-Dideoxy-1-O-methyl-2,3-O-(1-methylethylidene)-D-allofuranoside A solution of the vinylic sugar (6.2 g), Example 56, in methanol (55 mL) was hydrogenated using 10% platinum on carbon as catalyst at 80 psi for 100 hours. The catalyst was filtered and washed with methanol. The combined washings and filtrate were evaporated to obtain a colorless oil. Yield: quantitative.

EXAMPLE 59

Preparation of 5,6-Dideoxy-2,3-O-(1-methylethylidene)-D-allofuranose

A mixture of 5,6-dideoxy-1-methyl-2,3-O-(1-methylethylidene)-D-allofuranoside (5.8 g)(Example 58), and water (160 mL) containing 0.16 mL of conc. $H_2SO_4$ was heated to 90° C. for 3 hours. The pH of the reaction mixture was adjusted to 7.5 with 1N NaOH solution and evaporated to dryness. The residue was coevaporated with DMF (2×50 mL) then dissolved in methanol (25 mL) and filtered. The filtrate was evaporated, dissolved in a mixture of dry DMF (10 mL), 2,2-dimethoxypropane (10 mL) and potoluenesulfonic acid (200 mg) and stirred for 2 hours. The acid was neutralized with basic ion exchange resin and the resin filtered. The filtrate was evaporated and the residue chromatographed to obtain the title product; yield: 4.3 g.; TLC, Rf=0.6 (Silica gel, 2:1 hexane: EtOAc).

EXAMPLE 60

Preparation of 5-deoxy-1-O-methyl-2,3-O-(1-methylethylidene)-D-allofuranoside

To a solution of the vinylic sugar Example 56 (4.1 g) in THF (20 mL), borane:THF solution (10.65 mL of 1M solution in THF) was added over 10 minutes. After stirring 2 hours the reaction vessel was immersed in a cooling bath (ice-water) and NaOH (8 mL of 3M solution) was added with stirring. After 15 minutes a solution of $H_2O_2$ (30% aq., 4 mL) was added dropwise, and stirring was continued for 15 minutes. The flask was maintained at 55° C. for 30 minutes and cooled. The contents were extracted with methylene chloride (3×150 mL) and the organic layer was dried. The solvent was evaporated and the residue was chromatographed. The minor product, Rf=0.7, (10%) was identified as 6-deoxy-1-methyl-2,3-O-(1-methylethylidene)-D-allofuranoside. The slower moving major product (90%), Rf=0.3 was identified by proton NMR to be the title compound; yield 3.7 g; Rf=0.3 (silica gel, 2:1 hexane:EtOAc).

EXAMPLE 61

Preparation of 6-O-(t-Butyldimethylsilyl)-2,3-O-(1-methylethylidene)-D-allofuranose This compound may be prepared by t-butyldimethylsilylation of the 6-hydroxy sugar, using t-butyldimethylsilyl chloride and imidazole in DMF.

EXAMPLE 62

Preparation of 5-deoxy-1-methyl-2,3-O-(1-methylethylidene)-6-p-toluenesulfonyl-D-allofuranoside To an ice-cold solution of the hydroxy sugar Example 60, (3.69 g) in pyridine (25 mL), p-toluenesulfonyl chloride (3.7 g) was added. The reaction mixture was stirred and allowed to warm to room temperature. Unreacted p-toluenesulfonylchloride was quenched by adding 1 mL of methanol and the volatile components were evaporated. The residue was evaporated with DMF (2×20 mL), then dissolved in ethyl acetate (350 mL). The solution was washed and the organic layer was dried. Evaporation gave a residue which was chromatographed. Proton NMR indicated the product to be a mixture of α and β anomers.

EXAMPLE 63

Preparation of 6-azido-5,6-dideoxy-1-O-methyl-2,3-O-(1-methylethylidene)-D-allofuranoside A mixture of the tosyl sugar, Example 62, (4.0 g), dry DMF (20 mL) and sodium azide (1.5 g) was heated at 100° C. for 24 hours. The solvent was evaporated and the residue was dissolved in ethyl acetate (200 mL) and washed with water. The organic layer was dried and evaporated to obtain a colorless oil which was sufficiently pure by TLC and NMR for use in the next reaction; yield 2.09 g; Rf=0.35 (silica gel, 93:7 hexane:EtOAc).

EXAMPLE 64

Preparation of 6-azido-5,6-dideoxy-2,3-O-(1-methylethylidene)-D-allofuranose

A mixture of the azido sugar Example 63 (2.8 g), and aqueous sulfuric acid solution (100 mL of 0.1% by volume) was heated to 90° C. for 3½ hours. The pH of the reaction mixture was adjusted to 7.5 with 1N NaOH and evaporated to dryness. The residue was coevaporated with DMF (2×20 mL) and treated with methanol (25 mL). The insoluble solids were removed by filtration and washed with methanol (2×20 mL). The combined filtrates were evaporated to dryness. The oily product was dissolved in a mixture of dry DMF (10 mL), 2,2-dimethoxypropane (6 mL) and p-toluene sulfonic acid (50 mg) and stirred for 2 hours at room temperature. The solvents were evaporated and the residue was chromatographed. Fractions containing the main product were combined and evaporated to obtain the title compound as a colorless oil. Yield was 1.89 g.

EXAMPLES 65–81

General procedure for the preparation of 5'-substituted-4-chloropyrrolo[2,3-d]pyrimidine-7-(1-β-D-ribosides)

A solution of the 5-substituted (H, $OCH_3$, $N_3$ or TBDMS-O-) 5-deoxyisopropylideneribose (1 eq) in $CCl_4$ (1.4 eq) and THF was cooled to −78° C. Hexamethylphosphorous triamide (1.2 eq) was added dropwise and the reaction mixture stirred for 2 hours at −78° C. This solution of 1-α-chloro sugar was used directly in the next step.

To a slurry or solution of the substituted 4-chloropyrrolo[2,3-d]pyrimidine (1.4 eq corresponding to the sugar) in DMF, was added in four portions, NaH (1.4 eq) over 10 minutes. The solution was stirred 30 minutes then the above solution of chlorosugar (−25° C.) was added and the reaction was stirred for 24 hours. The mixture was concentrated, diluted with EtOAc, filtered and the filtrate concentrated under vacuum. The residue was chromatographed. The appropriate fractions were collected and evaporated to yield the protected nucleoside.

The protected nucleoside was deblocked by dissolving in 90% trifluoroacetic acid and stirring for 2 hours. The solvent was evaporated and chased with methanol (3×). The product was crystallized from EtOH.

The compounds in Table IV (Examples 65–81) were prepared by this procedure:

TABLE IV

| GP-1-# | EXAMPLE | B' | D | G | m.p. (°C.) |
|---|---|---|---|---|---|
| 475 | 65 | $CH_2OH$ | I | H | 183–181° |
| — | 66 | $CH_2N_3$ | I | $NH_2$ | 203–205° |
| 406 | 67 | $CH_2OH$ | Br | H | >230° |
| 448 | 68 | $CH_3$ | I | H | 180–181° |
| 449 | 69 | $CH_3$ | $CH_3$ | H | 155–157° |
| 462 | 70 | $CH_2OCH_3$ | $CH_3$ | H | 142–144° |
| 460 | 71 | $CH_2OCH_3$ | I | H | 179–180° |
| 464 | 72 | $CH_2OCH_3$ | H | H | 122–124° |
| 692 | 73 | $CH_2CH_3$ | Br | H | 163–165° |
| 690 | 74 | $CH_2CH_3$ | I | H | 181–183° |
| 529 | 75 | $CH_2N_3$ | I | H | 203–205° |
| 554 | 76 | $CH_3$ | Br | H | 174–175° |
| 555 | 77 | $CH_3$ | H | $CH_3S$ | 140–142° |
| 569 | 78 | $CH_3$ | $SCH_3$ | H | 147–148° |
| 605 | 79 | $CH_2N_3$ | Br | H | 156–158° |
| — | 80 | $CH_2CH_2N_3$ | I | H | foam |
| 713 | 81 | $CH=CH_2$ | I | H | 183–185° |

EXAMPLES 82–83

Preparation of 4-Amino-7-(5-amino-5-deoxy-1-β-D-ribofuranosyl)-5-halopyrrolo[2,3-d]pyrimidines A mixture of 4-chloro-5-iodo-7-(5-azido-5-deoxy-1-β-D-ribofuranosyl)pyrrolo[2,3-d]pyrimidine (Example 75 or 79) (500 mg), triphenylphosphine (550 mg) and pyridine (6 mL) was stirred at room temperature for 24 hours. Pyridine was evaporated and the residue triturated with ether. The residual semi-solid was treated with ammonium hydroxide (5 mL). Ethanol was added to cause complete dissolution of the compound. After stirring for 5 hours at room temperature the mixture was evaporated and the residue was triturated with water (10 mL). The insoluble material was filtered and the pH of the filtrate was adjusted to 5.5 with dilute HCl. The solution was refiltered and lyophilized to obtain a hygroscopic solid, whose NMR was compatible with the structure.

The above hygroscopic solid was dissolved in methanol, saturated with dry ammonia at −15° C., then heated in a steel bomb at 80° C. for 24 hours. The bomb was cooled and opened. The solution was evaporated and the residue was dissolved in water, charcoaled and filtered. The filtrate was lyophilized to obtain the title compound as a hygroscopic solid. The compounds listed in Table V were obtained by this procedure.

TABLE V

| GP-1-# | EXAMPLE | D | F | m.p. (°C.) |
|---|---|---|---|---|
| 550 | 82 | I | H | 166–206° |
| 649 | 83 | Br | H | 217–219° |

EXAMPLE 84

Preparation of 4-Amino-5-iodo-7-(5-acetylamino-5-deoxy-1-β-D-ribofuranosyl)pyrrolo[2,3-d]pyrimidine To an ice cold solution of the 5'-amino compound from Example 54 (50 mg), in pyridine (5 mL), acetic anhydride (0.5 mL) was added. The reaction mixture was allowed to warm to room temperature over 1 hour. The flask was reimmersed into the cooling bath and 15 mL of methanol was added to neutralize unreacted acetic anhydride. The solvent was evaporated under reduced pressure and the residue purified by chromatography to give the above-identified product, m.p. 160°–163° C.

EXAMPLES 85 TO 113B

General Procedure for the Preparation of $N^4$-Substituted-4-aminopyrrolo[2,3-d]pyrimidine Nucleosides A suspension of the substituted 4-Cl-pyrrolo[2,3-d] pyrimidine nucleoside (1 eq) in EtOH containing the amine (3 eq) and triethylamine (5 eq) was added to a small stainless steel bomb (in the case of diamines a 25% excess of chloride was used). The bomb was heated overnight (70°–120° C.), cooled, opened and the reaction mixture evaporated.

The product was crystallized from ethanol or ethyl acetate. The compounds in Table VI (Examples 85 to 113B) were prepared by this procedure:

collected by filtration, washed with water and dried in air: Yield 200 mg (81%); m.p. 161°–163° C.

EXAMPLES 115 TO 120

General Procedure for S-Alkylation of 5-Iodo-7-(5-deoxy-1-6-D-ribofuranosyl)pyrrolo[2,3-d]pyrimidin-4(3H)-thione To a solution of 5-iodo-7-(5-deoxy-1-β-D-ribofuranosyl) pyrrolo[2,3-d]pyrimidine-4-thione (Example 114) (50 mg) in concentrated $NH_4OH$ (10 mL), the appropriate alkylating agent (e.g. methyl iodide, alkyl or substituted benzyl bromide) was added and the mixture stirred at room temperature for 20 hours. Volatile material was evaporated and the residue triturated with ether. To the residue, water (5 mL) was added and the solid was collected by filtration.

The products obtained by this procedure (Examples 115 to 120) are listed in Table VII:

TABLE VI

| GP-1-# | Example | B' | D | F | G | m.p. (°C.) |
|---|---|---|---|---|---|---|
| 334 | 85 | $CH_2OH$ | H | $NH_2$ | H | 249–250° |
| 394 | 86 | $CH_2OH$ | H | N-indolinyl | H | Foam |
| 393 | 87 | $CH_2OH$ | H | N-prolinyl | H | Foam |
| 296 | 88 | $CH_2OH$ | H | cyclopentyl-NH | H | Foam |
| 376 | 89 | $CH_2OH$ | Br | $NH_2$ | H | Foam |
| 321 | 90 | $CH_2OH$ | H | NHØ | H | Foam |
| 476 | 91 | $CH_2OH$ | I | N-Indolinyl | H | 185–188° |
| 456 | 92 | $CH_3$ | I | $NH_2$ | H | 245–246° |
| 470 | 93 | $CH_3$ | I | N-indolinyl | H | 188–190° |
| 457 | 94 | $CH_3$ | I | $CH_3NH$ | H | 226–228° |
| 485 | 95 | $CH_3$ | I | $N_3$ | H | 213–214° |
| 498 | 96 | $CH_3$ | $CH_3$ | $NH_2$ | H | 212–214° |
| 461 | 97 | $CH_3$ | $CH_3$ | N-indolinyl | H | 171–173° |
| 463 | 98 | $CH2OCH_3$ | I | $NH_2$ | H | 216–218° |
| 465 | 99 | $CH_2OCH_3$ | I | $CH_3NH$ | H | 188–189° |
| 474 | 100 | $CH_2OCH_3$ | H | N-indolinyl | H | 205–208° |
| 480 | 101 | $CH_2OCH_3$ | H | $CH_3NH$ | H | 163–164° |
| 513 | 102 | $CH_3$ | H | N-piperazinyl | H | 216–219° |
| 499 | 103 | $CH_3$ | I | N,N'-piperazinyl | H | 220–223° |
| 500 | 104 | $CH_3$ | I | —NH($CH_2$)$_6$NH—[1] | H | 227–229° |
| 512 | 105 | $CH_3$ | I | —NH($CH_2$)$_2$NH—[1] | H | >230° |
| 559 | 106 | $CH_3$ | I | $NH_2$ | $CH_3S$ | 200–202° |
| 561 | 107 | $CH_3$ | H | 1,4-piperazinyl[2] | H | foam |
| 606 | 108 | $CH_2N_3$ | Br | $NH_2$ | H | 182–184° |
| 639 | 109 | $CH_3$ | I | NHØ | H | >230° |
| 581 | 110 | $CH_3$ | $CO_2Et$ | $NH_2$ | H | 162–168° |
| 681 | 111 | $CH_2OH$ | I | NHØ | H | 224–225° |
| 680 | 112 | $CH_2OH$ | I | NH(4-ClØ) | H | 234–235° |
| 689 | 113 | $CH_2OH$ | I | NH(4-$CH_3$O-Ø) | H | 212–214° |
| 711 | 113A | $CH_2CH_2N_3$ | I | $NH_2$ | H | 151–153° |
| 714 | 113B | $CH=CH_2$ | I | $NH_2$ | H | 224–226° |

[1]Dimers having two pyrrolo[2,3-d]pyrimidine riboside moieties linked by the listed diamine.
[2]Dimer with purine riboside.

EXAMPLE 114

Preparation of 5-Iodo-7-(5-deoxy-1-β-D-ribofuransyl)pyrrolo[2,3-d]pyrimidin-4(3H)-thione A solution of 4-chloro-5-iodo-7-[5-deoxy-1-β-D-ribofuranosyl]pyrrolo[2,3-d]pyrimidine (Example 68) (250 mg, 0.60 mmol) and thiourea (250 mg) in absolute, EtOH was refluxed for 16 hours. The solvent was evaporated and the residue was triturated with water (10 mL). The solid was

TABLE VI

| GP-1-# | Example | B' | D | F | m.p. (°C.) |
|---|---|---|---|---|---|
| 482 | 115 | $CH_3$ | I | $SCH_3$ | 212–233° |
| 493 | 116 | $CH_3$ | I | $SCH_2CH=CH_2$ | 192–193° |
| 494 | 117 | $CH_3$ | I | $SCH_2ØNO_2(4)$ | 224–226° |
| 502 | 118 | $CH_3$ | I | $SC_4H_9$ | 186–187° |

TABLE VI-continued

| GP-1-# | Example | B' | D | F | m.p. (°C.) |
|---|---|---|---|---|---|
| 503 | 119 | CH₃ | I | SCH₂Ø | 212–213° |
| 511 | 120 | CH₂OH | I | SCH₃ | 214–150° |

EXAMPLE 121

Preparation of 4-Phenyl-7-(1-β-D-ribofuranosyl)-pyrrolo[2,3d]pyrimidine

To a solution of 4-chloro-7-[2,3-O-(1-methylethylidene)-1-β-D-ribofuranosyl]pyrrolo[2,3-d]pyrimidine (200 mg) and phenylboronic acid (250 mg) in diglyme (10 mL) was added palladium-tetrakis-triphenylphosphine (30 mg), followed by aqueous $Na_2CO_3$ solution (0.2 mL of 2M solution). The reaction mixture was heated to 90° C. for 6 hours. The solvent was evaporated and the residue was purified by HPLC. The purified intermediate was treated with 2 mL of trifluoroacetic acid (80%) and stirred for 15 minutes then evaporated and the residue crystallized from ethanol; yield 20 mg, m.p. 163°–164° C.

EXAMPLES 122 TO 124

General Procedure for the Preparation of 4-Amino- and 4-Arylamino-5-aryl-7-(1-β-D-ribofuranosyl) pyrrolo-[2,3-d]pyrimidines To a stirred mixture of the 4-amino- or 4-arylamino-5-iodopyrrolo[2,3-d]pyrimidine riboside (or corresponding hydroxyl protected compound) (0.1 mmol), and $Pd(PPh_3)_4$ (10 mg, 0.01 mmol) in diglyme was added a solution of the arylboronic acid (0.4 mmol) in EtOH and 0.4 mL of aqueous 2M $Na_2CO_3$. The lo mixture was heated to 100° C. and the reaction monitored by TLC. After the reaction was complete, the cooled mixture was filtered and concentrated under vacuum. The residue was chromatographed over silica or by HPLC.

The compounds in Table VIII may be prepared by this procedure:

TABLE VIII

| GP-1-# | Example | D | F | m.p. (°C.) |
|---|---|---|---|---|
| — | 122 | Ø | ØNH | — |
| — | 123 | Ø | NH₂ | — |
| 718 | 124 | 2-furanyl | ØNH | foam |

EXAMPLES 125–126

General Procedure for the Preparation of 4-Amino- and 4-Arylamino-5-aryl-7-(5-deoxy-1-β-d-ribofuranosyl)pyrrolo[2,3-d]pyrimidines The above-identified compounds were prepared as described in Example 122–124 from the 4-amino- or 4-arylamino-5-iodo-7-(5-deoxy-1-β-D-ribofuranosyl) pyrrolo[2,3-d]pyrimidine and an arylboronic acid.

The compounds in Table IX were prepared by this procedure:

TABLE IX

| GP-1-# | Example | B' | D | F | G | m.p. (°C.) |
|---|---|---|---|---|---|---|
| 684 | 125 | CH₃ | Ø | NH₂ | H | 106–109 |
| 683 | 126 | CH₃ | Ø | NH-Ø | H | 207–208 |

EXAMPLE 127

Preparation of 4-Chloro-5-iodo-7-(6-deoxy-1-β-D-allofuranosyl)pyrrolo[2,3-d]pyrimidine The above-identified compound was prepared according to the general procedure used for Examples 65–81; m.p. 211°–213° C.

EXAMPLE 128

Preparation of 4-Amino-5-iodo-7-(6-deoxy-1-β-D-allofuranosyl)pyrrolo[2,3-d]pyrimidine The 4-chloro compound, Example 127, was heated in a steel bomb with methanolic ammonia at 120° C. for 12 hours followed by the usual work up (see Example 85). A white crystalline product was obtained; m.p. 206°–208° C.

EXAMPLES 129–130

General Procedure for the Preparation of 4-Amino-5-halo-7-(5,6-dideoxy-1-β-D-allofuranosyl)pyrrolo[2,3-d]pyrimidine The above-described compounds were prepared by the general procedures for Examples 65 to 81.

The compounds obtained by this procedure are listed in Table X.

TABLE X

| GP-1-# | Example | B' | D | F | G | m.p. (°C.) |
|---|---|---|---|---|---|---|
| 693 | 129 | CH₂CH₃ | Br | NH₂ | H | 229–230 |
| 691 | 130 | CH₂CH₃ | I | NH₂ | H | 233–234 |

EXAMPLE 131

Preparation of 4-Amino-3-bromopyrazolo[3,4-d] pyrimidine

The above-identified compound was prepared as described: Leonova, T.; Yashunskii, V.; *Khim. Get. Soed.*, 1982, 982.

EXAMPLE 132

Preparation of 4-Amino-3-(cyanomethyl)pyrazolo[3,4-d]pyrimidine

The above-identified compound was prepared as described: Carboni, R.,; Coffman, D.,; Howard, E.; *J.Am. Chem. Soc.*, 1958 80:2838.

EXAMPLE 133

Preparation of 4-Amino-3-cyanopyrazolo[3,4-d] pyrimidine

The above-identified compound was prepared as described: Taylor, E.; Abul-Hsan, A.; *J. Org. Chem.*, 1966, 31:342.

EXAMPLE 134

Preparation of 4-Amino-3-phenylpyrazolo[3,4-d]pyrimidine

The above-identified compound was prepared from trimethyl orthobenzoate as described: Kobayashi, S.; *Chem. Pharm. Bull. (Jap.)* 1973, 21:941.

EXAMPLES 135–139

General Procedure for the Preparation of Aryl Thiomorpholides

A mixture of the aromatic carboxaldehyde (0.1 mole), sulfur (4.8 g, 0.15 mole) and morpholine (18 mL, 0.15 mole) was heated at 180° C. for 3–5 hours then cooled and diluted with $H_2O$. The solid was collected by filtration or, if oily, extracted with $CH_2Cl_2$, dried and concentrated. The crude product was recrystallized or chromatographed over silica.

The compounds in Table XI were prepared by this procedure:

TABLE XI

| Example | Aryl | m.p. (°C.) |
|---|---|---|
| 135 | 4-CH$_3$OØ | 95–98° |
| 136 | 4-ClØ | 137–140° |
| 137 | 2-BrØ | — |
| 138 | 2-thienyl | 75–77° |
|  | 3-thienyl | 84–87° |
| 139 | 3-CH$_3$OØ | 134–139° |

EXAMPLES 140–144

General Procedure for the Preparation of 5-Amino-3-aryl-4-cyanopyrazoles

The above-identified compounds were prepared from the corresponding aryl thiomorpholides (Examples 135–139) following the general procedure described: Tominaga, Y.,; et al.; *J. Heterocyclic Chem.*, 1990, 27:647.

The compounds listed in Table XII were prepared by this procedure:

TABLE XII

| Example | Aryl | m.p. (°C.) |
|---|---|---|
| 140 | 4-CH$_3$OØ | 155–160° |
| 141 | 4-ClØ | 218–222° |
| 142 | 2-BrØ | — |
| 143 | 2-thienyl | 260–265° |
| 144 | 3-thienyl | 229–231° |

EXAMPLES 145–148

General Procedure for the Preparation of 5-Amino-3-aryl-4-carboxamidopyrazoles The above compounds were obtained from the corresponding cyano compounds (Example 140–144) following the general procedure described: Kobayashi, S.; *Chem. Pharm. Bull. (Jap.)*, 1973, 21:941.

The compounds listed in Table XIII were prepared by this procedure:

TABLE XIII

| Example | Aryl | m.p. (°C.) |
|---|---|---|
| 145 | Ø | 203–205° |
| 146 | 4-CH$_3$OØ | — |
| 147 | 4-ClØ | 210–215° |
| 148 | 2-BrØ | — |

EXAMPLE 149–154

General Procedure for the Preparation of 4-Amino-3-arylpyrazolo[3,4-d]pyrimidines A mixture of the 5-amino-3-aryl-4-cyanopyrazole and formamide (5 mL/g) was refluxed (190°–200° C.) for 4 hours. The cooled mixture was diluted with $H_2O$ and the solid collected by filtration. The crude products were used directly for subsequent steps or purified by recrystallization. The compounds listed in Table XIV were prepared by this procedure.

TABLE XIV

| Example | Aryl | m.p. (°C.) |
|---|---|---|
| 149 | Ø | >220 |
| 150 | 4-CH$_3$OØ | >220 |
| 151 | 4-ClØ | >220 |
| 152 | 2-BrØ | >220 |
| 153 | 2-Thienyl | >220 |
| 154 | 3-Thienyl | >283 (dec.) |

EXAMPLES 155–158

General Procedure for the Preparation of 3-Arylpyrazolo[3,4-d]pyrimidin-4-ones from 5-Amino-3-aryl-4-carboxamidopyrazoles A mixture of the 5-amino-3-aryl-4-carboxamidopyrazole and formamide (5 mL/g) was refluxed at 190°–200° C. for 2 hours, cooled and diluted with $H_2O$. The solid was collected by filtration and dried. Further purification was effected by dissolving the compound in dilute sodium hydroxide, followed by charcoal treatment and precipitation with acetic acid.

The compounds listed in Table XV were prepared by this procedure:

TABLE XV

| Example | Aryl | m.p. (°C.) |
|---|---|---|
| 155 | Ø | >200° |
| 156 | 4-CH$_3$OØ | >220° |
| 157 | 4-ClØ | >220° |
| 158 | 2-Thienyl | >220° |

EXAMPLES 159–160

General Procedure for Preparation of 3-Arylpyrazolo-[3,4d]pyrimidin-4-ones from 4-Amino-3-aryl-pyrazolo[3,4-d]pyrimidines To a slurry of the 3-aryl-4-aminopyrazolo[3,4-d]pyrimidine (25 mmoles) in 175 mL of 9% HCl at 0° to 5° C., was added, over 45 minutes, an aqueous solution of sodium nitrite (15.0 g in 30 mL). The mixture was allowed to warm to room temperature and solid sodium nitrite (5.0 g) was added. After 15 minutes the mixture was cautiously heated to boiling (foaming!), then cooled. The product was collected by filtration, rinsed with $H_2O$ and dried at 50° C. under vacuum.

The compounds listed in Table XVI were prepared by this procedure:

TABLE XVI

| Example | Aryl | m.p. (°C.) |
|---|---|---|
| 159 | ∅ | >220° |
| 160 | 2-thienyl | >220° |

EXAMPLES 161–163

General Procedure for the Preparation of $N^4$-Aryl and $N^4$-Alkyl Substituted 4-amino-3-aryl-pyrazolo [3,4-d]pyrimidines A mixture of the 3-arylpyrazolo[3,4-d]pyrimidin-4-one (15 mmoles), $POCl_3$(18 mL, 195 mmoles) and diethylaniline (5 mL, 31 mmoles) was refluxed for 4 hours then concentrated. The residue was decomposed by addition of ice and extracted (4×) with 3:1 ether-ethyl acetate. The combined organic extracts were washed with water and dried. The solution was concentrated and the crude 4-chloro-3-arylpyrazolo[3,4-d]pyrimidine (50–70% yield) was added to a solution of amine (2.2 equivalents) in EtOH (25 mL/mmole chloro compound). The mixture was refluxed for 30 minutes then cooled and the product collected by filtration and rinsed with ETCH. Recrystallization gave the title compounds.

The compounds listed in Table XVII were prepared by this procedure:

TABLE XVII

| Example | 3-Aryl | 4-Arylamino | m.p. (°C.) |
|---|---|---|---|
| 161 | ∅ | ∅ | 229–232° |
| 162 | ∅ | 4-Cl∅NH | 232–233° |
| 163 | ∅ | 4-CH$_3$O∅NH | 218–220° |

EXAMPLE 164

Preparation of 3-Bromopyrazolo[3,4-d]pyrimidin-4-one

The above-identified compound was prepared as described: Chu, I.; Lynch, B.; *J. Med. Chem.*, 1975, 18:161.

EXAMPLE 165

Preparation of 3-Bromo-1-(2,3,5-O-tribenzoyl-1-β-D-ribofuranosyl)pyrazolo[3,4-d]pyrimidin-4-one The above-identified compound was prepared as described: Cottam, H.; Petrie, C.; McKernan, P.; Goebel, R.; Dailey, N.; Davidson, R.; Robins, R.; Revankar, G.; *J. Med. Chem.*, 1984, 27:1120.

EXAMPLE 166

Preparation of 3-Substituted-4-chloro-1-(2,3,5,-O-tribenzoyl-1-β-D-ribofuranoyl)pyrazolo[3,4-d] pyrimidin-4-ones The above-identified compounds may be prepared from the corresponding pyrazolo[3,4-d]-pyrimidones by a procedure analogous to the one described in Example 2.

EXAMPLES 167 TO 169

General Procedure for Preparation of 3-Substituted 4-amino- and 4-(arylamino)-1-(1-β-D-ribofuranosyl) pyrazolo[3,4-d]pyrimidines To a slurry of the 3-substituted-4-chloropyrazolo[3,4-d] pyrimidine nucleoside tribenzoate (1.0 eq) (Example 166) in a mixture of EtOH and THF, was added ethanolic ammonia or the amine (1.5 eq) and $Et_3N$ (3.5 eq). The reaction rapidly became homogenous and after 0.5–12 hours, was evaporated. The residue was dissolved in $CH_2Cl_2$, washed with aqueous $K_2CO_3$ then $H_2O$ and the solution dried. After evaporation, the residue was recrystallized or chromatographed. The resulting tribenzoate of the title compound was deblocked by stirring in methanolic NaOMe. The mixture was neutralized with amberlite IR-120(+) resin, filtered and evaporated. The residue was recrystallized to give the title compounds.

Examples 167 to 169 listed in Table XVIII were prepared by this procedure:

TABLE XVIII

| GP-1-# | Example | 3- | 4- | m.p. (°C.) |
|---|---|---|---|---|
| 596 | 167 | I | NH$_2$ | 180–185° |
| 469 | 168 | Br | N-indolinyl | 195–196° |
| 536 | 169 | CH$_3$ | NH$_2$ | 241–242° |

EXAMPLE 170

Preparation of 4-(N-Indolinyl)-1-(1-β-D-ribofuranosyl)pyrazolo[3,4-d]pyrimidine

A solution of the bromide (Example 168) (351 mg, 0.78 mmol) in methanol containing 300 mg 10% Pd-C and Raney Ni was hydrogenated at 40 psi. The mixture was filtered, the filtrate concentrated and the product collected by filtration to give the title compound: 120 mg (42%); m.p. 215°–219°.

EXAMPLE 171

Preparation of 3-Bromo-1-[2,3-O-(1-methylethylidene)-1-β-D-ribofuranosyl]pyrazolo[3, 4-d]pyrimidin-4-one Crude 3-bromoallopurinol riboside (prepared from 33.0 g of tribenzoate and NaOMe/MeOH (Example 83) was added to a 5° C. solution of 1M ethanolic HCl (6.5 mL) and dimethoxypropane (20 mL) in 1.1 L of acetone. The mixture was stirred 45 minutes. $Na_2CO_3$ (5.0 g) and concentrated $NH_4OH$ (5 mL) were added and the mixture pH reached 6–7. The reaction was filtered and evaporated. The residual solid was dissolved in 300 mL of boiling EtOH and the solution concentrated. The solution was chilled overnight and the solid collected by filtration. After drying (50° C.), 16.7 g (86%) of the title compound were obtained; m.p. 221+≅224° C.

EXAMPLE 172

Preparation of 3-Bromo-1-[2,3-O-(1-methylethylidene)-5-O-(4-methylbenzenesulfonyl)-1-β-D-ribofuransyl]pyrazolo[3,4-d]pyrimidin-4-one To a solution of the isopropylidene alcohol (Example 171) (3.0 g, 7.74 mmol) in pyridine (18 mL) at 0° C. was added p-toluenesulfonyl chloride (1.77 g, 9.30 mmol). The reaction was held at 0° C. for 3 hours then poured into 160 mL of cold $H_2O$. The $H_2O$ was decanted and the residue dissolved in $CH_2Cl_2$. The $CH_2Cl_2$ solution was washed with 0.5N $H_2SO_4$, 5% aqueous $K_2CO_3$ and dried. After evaporation, 4.03 g (96% yield) of the title compound were obtained as a foam.

EXAMPLE 173

Preparation of 1-[5-Azido-5-deoxy-2,3-O-(1-methylethylidene)-1-β-D-ribofuranosyl]-3-bromopyrazolo[3,4-d]pyrimidin-4-one To a solution of $NaN_3$ (7.69 g, 0.12 moles) in DMSO (70 mL) was added the tosylate (Example 172) (16.0 g, 0.03 mol). The solution was rapidly heated to 80° C. and stirred for 45 minutes. After cooling, the reaction mixture was added to $H_2O$ (600 mL). The mixture was extracted and the combined extracts were washed with water, dilute brine, dried and concentrated to give 11.0 g of a white foam. TLC indicated a mixture of three products in the approximate ratio of 1:2:1. The middle spot was subsequently determined to be the desired azide.

The mixture was purified by chromatography. The fractions containing the desired product were combined and evaporated to give the title compound; 5.90 g (48% yield), m.p. 168° C. (d).

EXAMPLE 174

Preparation of 3-Amino-1-[2,3-O-(1-methylethylidene)-1-β-D-ribofuranosyl]pyazolo[3,4-d]pyrimidin-4-one A mixture of bromide (Example 171) (2.35 g, 6.1 mmol) CuCl (88 mg) and Cu (101 mg) in MeOH (45 mL) was placed in a bomb and saturated with ammonia. The bomb was sealed and heated to 110° C. for 10 hours. After cooling, the bomb was opened, the contents filtered and the filtrate evaporated. The residue was chromatographed. The appropriate fractions were combined and evaporated to yield the title compound as a solid; 2.1 g (98% yield); m.p. 142°–144° C.

EXAMPLE 175

Preparation of 3-Iodo-1-[2,3-O-(1-methylethylidene)-1-β-D-ribofuranosyl]pyrazolo[3,4-d]pyrimidin-4-one A mixture of the amine (Example 174) (2.58 g, 8.0 mmole), isoamyl nitrite (30 mL), methylene iodide (20 mL) and $CH_3CN$ was refluxed for 10 minutes. The cooled mixture was evaporated and chromatographed. Appropriate similar fractions were combined and evaporated to give the title compound: 1.08 g (66% yield); m.p. >220° C.

EXAMPLE 176

Preparation of 3-Iodo-1-[2,3-O-(1-methylethylidene)-5-O-(4- methylbenzenesulfonyl)-1-β-D-ribofuranosyl]pyrazolo-[3,4-d]pyrimidin-4-one The above identified compound was prepared by a procedure analogous to the one described for Example 172.

EXAMPLE 177

Preparation of 3-Iodo-1-[5-azido-5-deoxy-2,3-O-(1-methylethylidene)-1-β-D-ribofuranosyl]pyrazolo-[3,4-d]pyrimidin-4-one The above identified compound was prepared by a procedure analogous to the one described for Example 173 in 45% yield; m.p. 203° C.(d).

EXAMPLE 178

Preparation of 3-Halo-4-chloro-1-[5-azido-5-deoxy-2,3-O-(1-methylethylidene)-1-β-D-ribofuransyl)]pyrazolo[3,4-d]pyrimidine The above identified compounds were prepared by a procedure analogous to the one described for Example 2 from the pyrimidin-4-one (Example 173 or 177). The title compounds were obtained as unstable yellow oils and used immediately in the next step.

EXAMPLES 179 TO 181

General Procedure for the Preparation of 4-Amine and 4- hydrocarbyl-amino-1-(5-azido-5-deoxy-1-β-D-ribofuranosyl)pyrazolo[3,4d]pyrimidines To a solution of the chloro azide (Example 178) (1 eq) in 1:1 THF-EtOH (10% w/v), was added the amine (1.2–2.0 eq) and excess $Et_3N$ (for the 4-amine compounds the solution was saturated with $NH_3$ gas). The resulting solution was stirred for 2–24 hours.

The reactions using amines were worked up in the following manner. The reaction mixture was evaporated, the residue dissolved in $CH_2Cl_2$ and the solution washed with aqueous $NaHCO_3$, $H_2O$ and dried. Concentration of the $CH_2Cl_2$ solution and chromatography of the residue gave the purified isopropylidene N4-substituted compounds. The isopropylidene 4-amino compounds were isolated by evaporating the reaction mixture and recrystallizing the residue from EtOH.

The isopropylidene compounds were deblocked using the procedure described under Example 3.

The compounds in Table XIX (Examples 179 to 181) were prepared by this procedure:

TABLE XIX

| GP-1-# | Example | D | E | m.p. (°C.) |
|---|---|---|---|---|
| 507 | 179 | Br | $NH_2$ | 169–170° |
| 501 | 180 | Br | N-indolinyl | 133–138° |
| — | 181 | I | $NH_2$ | 193–195° |

EXAMPLES 182 TO 185

General Procedure for the Preparation of 4-Amino- and 4-Substituted-amino-1-(5-amino-5-deoxy-1-β-D-ribofuranosyl)-3-halopyrazolo[3,4-d]pyrimidines and Their Hydrochloride Salts A solution of the azide (Examples 179 to 181) (1.0 equivalent) and triphenylphosphine (1.5 equivalents) in pyridine (5 mL/g of azide) was stirred for 2 hours. To the reaction mixture was added $NH_4OH$ (1.25 mL/g of azide) and the solution stirred overnight. The solution was evaporated, slurried in $Et_2O$, filtered and the insoluble residue dried. The resulting solid was recrystallized or converted to its HCl salt and crystallized to give the title compounds.

The compounds in Table XX (Examples 182–185) were prepared by this procedure:

TABLE XX

| GP-1-# | Example | D | E | m.p. (°C.) (HCl salt) |
|---|---|---|---|---|
| 515 | 182 | Br | NH$_2$ | >230° |
| 516 | 183 | Br | N-indolinyl | 170° (broad) |
| 547 | 184 | I | NH$_2$ | 188 |
| 658 | 185 | Br | 1,4-piperazinyl[1] | 195° (broad) |

[1] a dimer

EXAMPLE 186

Preparation of 1,2,3-O-Triacetyl-5-deoxy-D-ribofuranoside

The above identified compound was prepared as described: Snyder, J.; Serianni, A.; *Carbohydrate Research*, 1987, 163:169.

EXAMPLE 197

Preparation of 1,2,3-O-Triacetyl-5-azido-5-deoxy-D-ribofuranoside

To a cooled solution of 5-azido-5-deoxyribose (6.2 g, 0.035 mole) (Example 51) in 10 mL of pyridine was added acetic anhydride (18 mL) and the mixture stirred for 24 hours. The mixture was concentrated, the residue dissolved in CH$_2$Cl$_2$ and the solution washed with 5% NaHCO$_3$. The organic layer was then washed with 0.5N H$_2$SO$_4$, dried and evaporated. The residue was dissolved in CH$_2$Cl$_2$, filtered through a plug of silica gel and the filtrate concentrated to afford the title compound, 9.0 g (98% yield) as a semisolid mixture of α and β isomers.

EXAMPLES 188–203

General Procedure for the Preparation of 5'-Substituted-3,4-disubstituted-pyrazolo[3,4-d]pyrimidine Nucleosides To a slurry of the 3,4-disubstituted pyrazolo[3,4-d]pyrimidine (5.0 mmol) in nitromethane, nitroethane or benzonitrile, was added the acyl-protected ribose (5.0–7.0 mmoles). To the stirred mixture was added BF$_3$-Et$_2$O (7.0 mmoles) and the mixture was refluxed for 90 minutes, then cooled and evaporated. If a 5'-deoxy derivative was used, Et$_3$N was added prior to the evaporation of the solvent.

The residue was taken up in CH$_2$Cl$_2$, filtered and chromatographed. Later fractions contained the N-2 isomer. Fractions containing the desired N-1 isomer were combined and evaporated to yield the title compounds as foams.

The compounds in Table XXI (Examples 188–203) were prepared by this procedure:

TABLE XXI

| Example | B' | D | E | m.p. (°C.) |
|---|---|---|---|---|
| 188 | ØCO$_2$CH$_2$ | CN | NH$_2$ | foam |
| 189 | ØCO$_2$CH$_2$ | CH$_2$CN | NH$_2$ | foam |
| 190 | ØCO$_2$CH$_2$ | Ø | NHØ | foam |
| 191 | CH$_2$N$_3$ | Br | NH$_2$ | foam |
| 192 | CH$_2$N$_3$ | CN | NH$_2$ | foam |
| 193 | CH$_2$N$_3$ | CH$_2$CN | NH$_2$ | foam |
| 194 | CH$_2$N$_3$ | Ø | NH$_2$ | foam |
| 195 | CH$_2$N$_3$ | 4-ClØ | NH$_2$ | foam |
| 196 | CH$_2$N$_3$ | 4-CH$_3$OØ | NH$_2$ | foam |
| 197 | CH$_2$N$_3$ | 2-thienyl | NH$_2$ | foam |
| 198 | CH$_3$ | Ø | NH$_2$ | foam |
| 199 | CH$_3$ | 4-CH$_3$OØ | NH$_2$ | foam |
| 200 | CH$_3$ | 4-ClØ | NH$_2$ | foam |
| 201 | CH$_3$ | 2-thienyl | NH$_2$ | foam |
| 202 | CH$_3$ | 3-thienyl | NH$_2$ | foam |
| 203 | CH$_3$ | Ø | NHØ | foam |

EXAMPLE 204

General Procedure for the Preparation of 3-Substituted 1-(5-azido-5-deoxy-2,3-O-diacetyl-1-β-D-ribo-furanosyl)-4-chloropyrazolo[3,4-d]pyrimidines,5'-Deoxy Analogs and Protected 5'-Hydroxy Analogs The above identified compounds were prepared from the pyrazolo[3,4-d]pyrimidone esters by a procedure analogous to the one described in Example 2 and were used immediately in the next step.

EXAMPLES 205–221

General Procedure for the Preparation of 3,4-Disubstituted-1-(5-azido-5-deoxy-1-β-D-ribofuranosyl))pyrazolo-[3,4-d]pyrimidines, 5'-Deoxy Analogs and 5'-Hydroxy Analogs The above identified compounds were prepared from the diestem by a procedure analogous to the one described in Example 167–169. Methanolic NH$_3$ (method A) or NaOMe (method B) was used to deblock the acyl-protected nucleosides (Examples 188–204). In the case of the cyano-substituted compounds, these methods led to different products by further reaction of the cyano group. The title compounds were isolated by conventional techniques.

The compounds listed in Table XXII (Examples 205–221) were prepared by this procedure.

TABLE XXII

| Example | GP-1-# | B' | D | F | m.p. (°C.) |
|---|---|---|---|---|---|
| 205 | 612 | CH$_2$OH | CH$_2$CN | NH$_2$ A | 220° (dec) |
| 206 | 613 | CH$_2$OH | CH$_2$C(=NH)OCH$_3$ | NH$_2$ B | 75°(dec) |
| 207 | 695 | CH$_2$OH | Ø | NHØ B | 220–224° |
| 208 | 507 | CH$_2$N$_3$ | Br | NH$_2$ B | 172° (d) |
| 209 | 623 | CH$_2$N$_3$ | C(=NH)NH$_2$ | NH$_2$ A | 203–206° |
| 210 | 624 | CH$_2$N$_3$ | CH$_2$CN | NH$_2$ A | 153–156° |
| 211 | 641 | CH$_2$N$_3$ | Ø | NH$_2$ B | 203–205° |
| 212 | 662 | CH$_2$N$_3$ | 4-ClØ | NH$_2$ B | 175–177° |
| 213 | 666 | CH$_2$N$_3$ | 4-CH$_3$OØ | NH$_2$ B | 153–155° |
| 214 | 654 | CH$_2$N$_3$ | 2-Thienyl | NH$_2$ B | 180–181° |
| 215 | 667 | CH$_2$N$_3$ | Ø | NHØ B | 120–125° |
| 216 | 663 | CH$_3$ | Ø | NH$_2$ B | 223–224° |
| 217 | 678 | CH$_3$ | 4-ClØ | NH$_2$ B | 130–133° |
| 218 | 679 | CH$_3$ | 4-CH$_3$OØ | NH$_2$ B | 175–176° |
| 219 | 664 | CH$_3$ | 2-Thienyl | NH$_2$ B | 174–175° |
| 220 | 685 | CH$_3$ | 3-Thienyl | NH$_2$ B | 153–154° |
| 221 | 665 | CH$_3$ | Ø | NHØ B | 207–208° |

EXAMPLES 222–229

General Procedure for the Preparation of 4-Amino- and 4-Arylamino-3-substituted-1-(5-amino-5-deoxy-1-β-D-ribofuranosyl)pyrazolo[3,4-d]pyrimidines and Their Salts The above-identified compounds were prepared from the 5'-azides (Examples 205–221) by catalytic hydrogenation as described in Examples 15–20 (method A) or triphenylphosphine followed by ammonium hydroxide as described in Examples 82–83 (method B). The salts were prepared by standard methods.

The compounds listed in Table XXIII were be prepared by these methods:

TABLE XXIII

| GP-1-# | Example | 3- | 4- | Method | Salt | m.p. (°C.) |
|---|---|---|---|---|---|---|
| 515 | 222 | Br | $NH_2$ | B | HCl | >230° |
| 614 | 223 | H | $NH_2$ | A | HBr | 160° (d) |
| 625 | 224 | $CH_2CN$ | $NH_2$ | B | — | 175° (d) |
| 642 | 225 | Ø | $NH_2$ | A | HCl | 218–219° |
| 682 | 226 | 2-thienyl | $NH_2$ | B | HCl | >220° |
| 694 | 227 | 4-$CH_2$OØ | $NH_2$ | A | — | 222–225° |
| 701 | 228 | 4-ClØ | $NH_2$ | B | HCl | 189–194° |
| 704 | 229 | Ø | NHØ | A | $CF_3CO_2H$ | 185–190° |

EXAMPLES 230–231

General Procedure for the Preparation of 4-Amino- and 4-Arylamino-1-(5-amino-2,3-O-diacetyl-5-deoxy-1-β-D-ribofuranosyl)-3-substituted pyrazolo[3,4-d]pyrimidines A slurry of 10% Pd-C in a solution (MeOH or EtOH with THF, dioxane or EtOAc) of the 5'-azido-2',3'-diacetate nucleoside (Examples 191–198) was hydrogenated in a Parr shaker at 40 psi. After disappearance of the starting material (TLC), the mixture was filtered and concentrated. The residual product was purified by recrystallization or HPLC.

The compounds listed in Table XXIV were prepared by this method:

TABLE XXIV

| GP-1-# | Example | D | F | C1, C2 | m.p (°C.) |
|---|---|---|---|---|---|
| — | 230 | Br | $NH_2$ | OAc | — |
| — | 231 | Ø | NHØ | OAc | — |

EXAMPLES 232–233

General Procedure for the Preparation of 3-Substituted-4(1,1-dicarboethoxyalkyl)-1-(2,3,5-O-tribenzoyl-1-β-D-ribofuranosyl)pyrazolo[3,4d]pyrimidines To a solution of the diethyl(alkyl)malonate (0.10 mol) in DMF (100 mL) was added 80% NaH in mineral oil (0.125 mol). After stirring for 10 minutes, a solution of the 3-substituted-4-chloro-1-(2,3,5-tribenzoyl-1-β-D-ribofuranosyl)pyrazolo[3,4-d]pyrimidine (0.09 mol) (Example 178) in DMF (75 mL) was added dropwise. The solution was cooled and anhydrous trimethylamine was bubbled into the solution for 4 minutes. The solution was stirred for 3 hours at room temperature then quenched with dilute acetic acid. The mixture was extracted with ether-ethyl acetate (9:1) and the organic extract dried and concentrated. The residue was chromatographed and the appropriate fractions combined and evaporated to yield the title compounds. The identity of the compounds were confirmed by NMR.

The compounds listed in Table XXV were prepared by this procedure:

TABLE XXV

| Example | D | F | m.p. (°C.) |
|---|---|---|---|
| 232 | Br | $CH(CO_2C_2H_5)_2$ | foam |
| 233 | Br | $CØ(CO_2C_2H_5)_2$ | foam |

EXAMPLES 234–235

General Procedure for Preparation of 4-Alkyl, 4-Arylalkyl- and 3,4-disubstituted-1-(1-β-D-ribofuranosyl)pyrazolo[3,4-d]pyrimidines The diester (Examples 232–233) was dissolved in aqueous ethanolic sodium hydroxide and heated. The solution was neutralized with acetic acid, evaporated, extracted with hot ethanol and the extract then evaporated and recrystallized or chromatographed. The appropriate fractions were combined and evaporated to yield the title compounds.

The compounds described in Table XXVI were prepared by the procedure:

TABLE XXVI

| GP-1-# | Example | D | E | m.p. (°C.) |
|---|---|---|---|---|
| 719 | 234 | Br | $CH_3$ | 204–205° |
| — | 235 | Br | $CH_2$Ø | — |

EXAMPLES 286–237

General Procedure for Preparation of 3-Substituted-4-(1,1-dicarboethoxyalkyl)-1-(5-azido-5-deoxy-2,3-O-diacetyl-1-β-D-ribofuranosyl)pyrazolo[3,4-d]pyrimidines The above identified compounds were prepared by a procedure analogous to the one described in Examples 232–233 using the 3-substituted-(5-azido-5-deoxy-2,3-O-diacetyl-1-β-D-ribofuranosyl)-4-chloropyrazolo[3,4-d]pyrimidine.

The compounds listed in Table XXVII were prepared by this procedure:

TABLE XXVII

| Example | D | F | m.p. (°C.) |
|---|---|---|---|
| 236 | Br | $CØ(CO_2C_2H_5)_2$ | — |
| 237 | Br | $CH(CO_2C_2H_5)_2$ | — |

EXAMPLES 238–239

General Procedure for Preparation of 4-Alkyl-, 4-Phenylalkyl- and 4-Substituted-3-Substituted-1-(5-azido-5-deoxy-1-β-D-ribofuranosyl) pyrazolo[3,4-d]-pyrimidines The above identified compounds were prepared by a procedure analogous; to the one described in Examples 234–235 from the 5'-azide esters described in Examples 236–237.

The following compounds listed in Table XXVIII were prepared by this procedure:

TABLE XXVIII

| GP-1-# | Example | D | F | m.p. (°C.) |
|---|---|---|---|---|
| — | 238 | Br | CH₃ | — |
| — | 239 | Br | CH₂Ø | — |

EXAMPLES 240–241

General Procedure for the Preparation of 4-Alkyl-4-Phenylalkyl- and 3,4-Disubstituted-1-(5-amino-5-deoxy-1-β-D-ribofuranosyl)pyrazolo[3,4-d]pyrimidines The above-identified compounds were prepared by reduction of the 5-azido ribosides listed in Examples 238–239 by catalytic hydrogenation as described in Examples 15–20 or by treatment with triphenylphosphine and ammonium hydroxide as described in Examples 182–185.

The compounds listed in Table XXIX were prepared by this procedure:

TABLE XXIX

| GP-1-# | Example | D | F | m.p. (°C.) |
|---|---|---|---|---|
| — | 240 | Br | CH₃ | — |
| — | 241 | Br | CH₂Ø | — |

EXAMPLES 242–243

General Procedures for the Preparation of 3-Substituted-1-(5-deoxy-2,3-O-diacetyl-1-β-D-ribofuranosyl)-4-(1,1-dicarboethoxyalkyl)pyrazolo[3,4-d]pyrimidines The above-identified compounds were prepared by a procedure analogous to the one described in Examples 232–233 using 3-substituted-4-chloro-1-(5-deoxy-2,3-O-diacetyl-1-β-D-ribofuranosyl)pyrazolo[3, 4-d]pyrimidines (Examples 198–203).

The compounds listed in Table XXX were prepared by this procedure:

TABLE XXX

| GP-1-# | Example | D | F | m.p. (°C) |
|---|---|---|---|---|
| — | 242 | Br | CH(CO₂C₂H₅)₂ | — |
| — | 243 | Br | C(CO₂C₂H₅)₂CHØ | — |

EXAMPLES 244–245

General Procedure for the Preparation of 4-Alkyl-, 4-Phenylalkyl- or 4-Substituted-3-substituted-1-(5-deoxy-1-β-D-ribofuranosyl)pyrazolo[3,4-d]pyrimidines The above-identified compounds were prepared from the esters (Examples 242–243) using the procedure described in Examples 234–235.

The compounds listed in Table XXXI were prepared by this method:

TABLE XXXI

| GP-1-# | Example | D | F | m.p. (°C.) |
|---|---|---|---|---|
| — | 244 | Br | CH₂CH₂Ø | — |
| — | 245 | Br | CH₂Ø | — |

By following the procedures described in the Detailed Description of the Invention and Examples 1 to 245 and using the appropriate starting materials and reagents, the following compounds were made:

4-Amino-7-(5-deoxy-1-β-D-ribofuranosyl)-5-vinylpyrrolo[2,3-d]pyrimidine;

4-Amino-5-ethynyl-7-(5-deoxy-1-β-D-ribofuranosyl)pyrrolo[2,3-d]pyrimidine;

5-(2-Chlorophenyl)-7-(5-deoxy-1-β-D-ribofuranosyl)-4-phenylaminopyrrolo[2,3-d]pyrimidine;

5-(3-Chlorophenyl)-7-(5-deoxy-1-β-D-ribofuranosyl)-4-phenylaminopyrrolo[2,3-d]pyrimidine;

5-(4-Chlorophenyl)-7-(5-deoxy-1-β-D-ribofuranosyl)-4-phenylaminopyrrolo[2,3-d]pyrimidine;

5-(2-Methoxyphenyl)-7-(5-deoxy-1-β-D-ribofuranosyl)-4-phenylaminopyrrolo[2,3-d]pyrimidine;

5-(4-Methoxyphenyl)-7-(5-deoxy-1-β-D-ribofuranosyl)-4-phenylaminopyrrolo[2,3-d]pyrimidine;

5-(2-Furanyl)-7-(5-deoxy-1-β-D-ribofuranosyl)-4-phenylaminopyrrolo[2,3-d]pyrimidine;

7-(5-Deoxy-1-β-D-ribofuranosyl)-4-phenylamino-5-(2-pyridyl)pyrrolo[2,3-d]pyrimidine;

7-(5-Deoxy-1-β-D-ribofuranosyl)-4-phenylamino-5-(4-pyridyl)pyrrolo[2,3-d]pyrimidine;

7-(5-Deoxy-1-β-D-ribofuranosyl)-5-phenyl-4-(4-pyridylamino)pyrrolo[2,3-d]pyrimidine;

7-(5-Deoxy-1-β-D-ribofuranosyl)-5-phenyl-4-(2-pyridylamino)-pyrrolo[2,3-d]pyrimidine;

7-(5-Deoxy-1-β-D-ribofuranosyl)-5-phenyl-4-(1-piperazinyl)-pyrrolo[2,3-d]pyrimidine;

4-(2-Chlorophenyl)-7-(5-deoxy- 1-β-D-ribofuranosyl)-5-phenylpyrrolo[2,3-d]pyrimidine;

4-(3-Chlorophenyl)-7-(5-deoxy-1-β-D-ribofuranosyl)-5-phenylpyrrolo[2,3-d]pyrimidine;

7-(5-Deoxy-1-β-D-ribofuranosyl)-5-phenyl-4-(2-thiazolyl-amino)pyrrolo[2,3-d]pyrimidine;

4-Cyclohexylamino-7-(5-deoxy-1-β-D-ribofuranosyl)-5-phenylpyrrolo[2,3-d]pyrimidine;

7-(5-Deoxy-1-β- D-ribofuranosyl)-5-phenyl-4-phenylthiopyrrolo[2,3-d]pyrimidine;

4-Benzyl-7-(5-deoxy-1-β-D-ribofuranosyl)-5-phenylpyrrolo[2,3-d]pyrimidine;;

7-(5-Deoxy-1-β-D-ribofuranosyl)-4-ethynyl-5-phenylpyrrolo[2,3- d]pyrimidine;

7-(5-Deoxy-1-β-D-ribofuranosyl)-4-methyl-5-phenylpyrrolo[2,3-d]pyrimidine;

4-Benzyl-7-(5-deoxy-1-β-D-ribofuranosyl)-5-iodopyrrolo[2,3-d]pyrimidine;

7-(5-Deoxy-1β-D-ribofuranosyl)-5-iodo-4-methylpyrrolo[2,3-d]pyrimidine;

7-(5-Deoxy-1-β-D-ribofuranosyl)-5-phenyl-4-phenylaminopyrrolo[2,3-d]pyrimidine;

4-Amino-5-phenyl-7-(1-β-D-ribofuranosyl)pyrrolo[2,3-d]-pyrimidine;

4-Amino-7-(5-deoxy-5-mercapto-1-β-D-ribofuranosyl)-5-iodopyrrolo[2,3-d]pyrimidine;

7-(5-Deoxy-5-mercapto-1-β-D-ribofuranosyl)-5-iodo-4-phenylaminopyrrolo[2,3-d]pyrimidine;

7-(5-Deoxy-5-mercapto-1-β-D-ribofuranosyl)-5-phenyl-4-phenylaminopyrrolo[2,3-d]pyrimidine;

7-(5-Amino-5-deoxy-1-β-D-ribofuranosyl)-5-phenyl-4-phenylaminopyrrolo[2,3-d]pyrimidine;

7-(5,6-Dideoxy-1-β-D-allofuranosyl)-5-iodo-4-phenylamino-pyrrolo[2,3-d]pyrimidine;

7-(5,6-Dideoxy-1-β-D-allofuranosyl)-5-phenyl-4-phenylaminopyrrolo[2,3-d]pyrimidine;

4-Amino-7-(5,6-dideoxy-1-β-D-allofuranosyl)-5-phenylpyrrolo[2,3-d]pyrimidine;

4-Amino-7-(5-deoxy-5-fluoro-1-β-D-ribofuranosyl)-5-iodopyrrolo[2,3-d]pyrimidine;

4-Amino-7-(5-deoxy-5-chloro-1-β-D-ribofuranosyl)pyrrolo[2,3-d]pyrimidine;

7-(5-Deoxy-5-fluoro-1-β-D-ribofuranosyl)-5-phenyl-4-phenylaminopyrrolo[2,3-d]pyrimidine;

4-Amino-7-(6-azido-5,6-dideoxy-1-β-D-allofuranosyl)-5-iodopyrrolo[2,3-d]pyrimidine;

7-(6-Azido-5,6-dideoxy-1-β-D-allofuranosyl)-5-phenyl-4-phenylaminopyrrolo[2,3-d]pyrimidine;

4-Amino-7-(6-amino-5,6-dideoxy-1-β-D-allofuranosyl)-5-iodopyrrolo[2,3-d]pyrimidine;

7-(6-Amino-5,6-dideoxy-1-β-D-allofuranosyl)-5-phenyl-4-phenylaminopyrrolo[2,3-d]pyrimidine;

5-(2-Methoxyphenyl)-7-[1-β-D-ribofuranosyl]-4-phenylaminopyrrolo[2,3-d]pyrimidine;

4-Amino-5-bromo-7-(5,6-didehydro-5,6-dideoxy-1-β-D-allofuranosyl)pyrrolo[2,3-d]pyrimidine;

7-(5,6-Didehydro-5,6-dideoxy-1-β-D-allofuranosyl)-5-phenyl-4-phenylaminopyrrolo[2,3-d]pyrimidine;

4-Amino-1-(5-amino-5-deoxy-1-β-D-ribofuranosyl)-3-methoxypyrazolo[3,4-d]pyrimidine;

4-Amino-1-(5-amino-5-deoxy-1-β-D-ribofuranosyl)-3-phenoxypyrazolo[3,4-d]pyrimidine;

4-Amino-1-(5-amino-5-deoxy-1-β-D-ribofuranosyl)-3-phenylthiopyrazolo[3,4-d]pyrimidine;

4-Amino-1-(5-amino-5-deoxy-1-β-D-ribofuranosyl)-3-methylthiopyrazolo[3,4-d]pyrimidine;

4-Amino-1-(5-amino-5-deoxy-1-β-D-ribofuranosyl)-3-chloropyrazolo[3,4-d]pyrimidine;

4-Amino-1-(5-amino-5-deoxy-1-β-D-ribofuranosyl)-3-cyclopropylpyrazolo[3,4-d]pyrimidine;

4-Amino-1-(5-amino-5-deoxy-1-β-D-ribofuranosyl)-3-dimethylaminopyrazolo[3,4-d]pyrimidine;

4-Amino-1-(5-amino-5-deoxy-1-β-D-ribofuranosyl)-3-fluoropyrazolo[3,4-d]pyrimidine;

4-Amino-1-(5-amino-5-deoxy-1-β-D-ribofuranosyl)-3-(3-pyridyl)pyrazolo[3,4-d]pyrimidine;

1-(5-Amino-5-deoxy-1-β-D-ribofuranosyl)-4-(3-chlorophenyl)-3-(4-methoxyphenyl)pyrazolo[3,4-d]pyrimidine;

1-(5-Amino-5-deoxy-1-β-D-ribofuranosyl)-4-(4-chlorophenyl)-3-(4-methoxyphenyl)pyrazolo[3,4-d]pyrimidine;

1-(5-Amino-5-deoxy-1-β-D-ribofuranosyl)-4-(4-ethoxyphenyl)-3-(4-methoxyphenyl)pyrazolo[3,4-d]pyrimidine;

1-(5-Amino-5-deoxy-1-β-D-ribofuranosyl)-4-(3-carboxamidophenylamino)-3-(4-methoxyphenyl)pyrazolo[3,4-d]pyrimidine;

1-(5-Amino-5-Deoxy-1-β-D-ribofuranosyl)-4-(2-furanyl)-3-(4-methoxyphenyl)pyrazolo[3,4-d]pyrimidine;

1-(5-Deoxy-1-β-D-ribofuranosyl)-3-(4-methoxyphenyl)-4-(phenylamino)pyrazolo[3,4-d]pyrimidine;

1-(5-Deoxy-1-β-D-ribofuranosyl)-3-(3-methoxyphenyl)-4-(phenylamino)pyrazolo[3,4-d]pyrimidine;

1-(5-Deoxy-1-β-D-ribofuranosyl)-3-(2-pyridyl)-4-(phenylamino)pyrazolo[3,4-d]pyrimidine;

1-(5-Deoxy-1-β-D-ribofuranosyl)-3-(4-methoxyphenyl)-4-(4-pyridylamino)pyrazolo[3,4-d]pyrimidine;

1-(5-Deoxy-1-β-D-ribofuranosyl)-3-(3-methoxyphenyl)-4-(4-pyridylamino)pyrazolo[3,4-d]pyrimidine;

1-(5-Deoxy-1-β-D-ribofuranosyl)-3-(2-pyridyl)-4-(4-pyridylamino)pyrazolo[3,4-d]pyrimidine;

1-(5-deoxy-1-β-D-ribofuranosyl)-3-(4-methoxyphenyl)-4-(2-methoxyphenylamino)pyrazolo[3,4-d]pyrimidine;

1-(5-Deoxy-1-β-D-ribofuranosyl)-3-(3-methoxyphenyl)-4-(2-methoxyphenylamino)pyrazolo[3,4-d]pyrimidine;

1-(5-Deoxy-1-β-D-ribofuranosyl)-3-(4-pyridyl)-4-(2-methoxyphenylamino)pyrazolo[3,4-d]pyrimidine;

1-(5-Deoxy-1-β-D-ribofuranosyl)-3-(4-methoxyphenyl)-4-(2-imidazolylamino)pyrazolo[3,4-d]pyrimidine;

1-(5-Deoxy-1-β-D-ribofuranosyl)-3-(3-methoxyphenyl)-4-(2-imidazolylamino)pyrazolo[3,4-d]pyrimidine;

1-(5-Deoxy- 1-β-D-ribofuranosyl)-3-(2-pyridyl)-4-(2-imidazolylamino)pyrazolo[3,4-d]pyrimidine;

1-(5-Deoxy-1-β-D-ribofuranosyl)-3-(2-pyrazinyl)-4-phenylaminopyrazolo[3,4-d]pyrimidine;

1-(5-Deoxy-1-β-D-ribofuranosyl)-3-(2-pyrazinyl)-4-(N-indolinyl)pyrazolo[3,4-d]pyrimidine;

1-(5,6-Dideoxy-1-β-D-allofuranosyl)-3-phenyl-4-phenylaminopyrazolo[3,4-d]pyrimidine;

4-Amino-1-(5,6-dideoxy-1-β-D-allofuranosyl)-3-iodopyrazolo[3,4-d]pyrimidine;

1-(5-Deoxy-1-β-D-ribofuranosyl)-3-phenyl-4-phenylthiopyrazolo[3,4-d]pyrimidine;

1-(5-Amino-5-deoxy-1-β-D-ribopuranosyl)-3-bromo-4-methylpyrazolo[3,4-d]pyrimidine;

1-(5-Amino-5-deoxy-1-β-D-ribofuranosyl)-4-methyl-3-iodopyrazolo[3,4-d]pyrimidine;

7-(5-Deoxy-1-β-D-ribofuranosyl)-5-iodo-4-methylpyrrolo[2,3-d]pyrimidine;

4-Methyl-3-phenyl-1-(1-β-D-ribofuranosyl)pyrazolo[3,4-d]pyrimidine;

1 -(5-Deoxy-1-β-D-ribofuranosyl)-3-phenyl-4-(phenylmethyl)pyrazolo[3,4-d]pyrimidine; and 7-(5-Amino-5-deoxy-1-β-D-ribofuranosyl)-5-bromo-4-chloropyrrolo[2,3-d]pyrimidine(GP-1-608).

EXAMPLE A

A Method of Measuring the Inhibition of Adenosine Kinase Activity

Inhibition of enzyme activity was determined using a 0.1 mL assay mixture containing 50 mM Tris-maleate, pH 7.0, 0.1% (w/v) BSA, 1 mM ATP, 1 mM $MgCl_2$, 0.5 µM [U-$^{14}$C]adenosine (500 mCi/mmol) and 0.1 µg of purified pig heart adenosine kinase. Different concentrations of the test compounds were incubated in the assay mixture for 20 min. at 37° C. From each reaction mixture, 20 µl portions were removed and spotted on 2 $cm^2$ pieces of Whatman DE81 filter paper. The papers were then washed to remove

[$^{14}$C]adenosine in 1 mM ammonium formate followed by deionized water and finally 95% ethanol. The papers were dried, and [$^{14}$C]AMP measured by scintillation counting. Activities were determined from the amount of [$^{14}$C]AMP formed.

A1 receptor binding affinity was determined using 0.5 mL mixture containing 50 mM Tris HCl, pH 7.4, 1 nM [$^{3}$H] cyclohexyladenosine (CHA) and 0.5 mg of neuronal membrane incubated with different concentrations of the test compound for 60 min at 37° C. The reaction was stopped and unbound [$^{3}$H]CHA removed by rapid filtration through Whatman GF/B filters. The filter papers, were then solubilized and bound [$^{3}$H]CHA determined by scintillation counting.

Inhibition of adenosine deaminase activity was determined spectrophotometrically using a 1 mL assay mixture containing 50 mM potassium phosphate, pH 7.0, 1 mM ADP, 2.5 mM alpha-ketoglutarate, 15 units glutamic dehydrogenase, 0.125 mM NADH, 80 µM adenosine and 0.002 units of calf intestinal mucosa adenosine deaminase. Different concentrations of the test compounds were incubated in the assay mixture for 10 min at 37° C. The reaction was monitored continuously for oxidation of NADH from the change in absorbance at 340 nm.

Illustrative of the invention, the compounds designated GP-1-515, GP-1-608, GP-1-683, GP-1-695, GP-1-718, GP-1-704, GP-1-665, and GP-1-667, were found to have an $IC_{50}$ of less than 10 nM in the adenosine kinase inhibition assay. The compound GP-1-515 was found to be much less potent in the A1 receptor assay and in the adenosine deaminase inhibition assay, having an $IC_{50}$ greater than 100 µM in the A1 receptor assay and an $IC_{50}$ greater than 1000 µM in the adenosine deaminase inhibition assay.

EXAMPLE B

Adenosine Kinase Inhibition in Intact Cells

Inhibition of adenosine kinase in intact cells was determined from the amount of incorporation of radioisotope from adenosine into the adenylates (AMP, ADP and ATP) in the presence of adenosine deaminase inhibition. Capillary endothelial cells from bovine heart were incubated for 60 min. with 20 µM 2'-deoxycoformycin, a potent adenosine deaminase inhibitor. Different concentrations of the test compounds were then added to the cells and incubated for 15 min. after which 5 µM [$^{3}$H]adenosine was added and the cells incubated for a further 15 min. The media was then discarded and the cells were treated with 50 µl 0.4M perchloric acid, centrifuged and the supernalants neutralized with 100 µl alanine: freon (1:4). Radioisotope-labeled adenylates were separated by TLC on PEI cellulose plates developed in methanol:water (1:1) and incorporation of $^{3}$H determined by scintillation counting.

Illustrative of the invention, the compounds designated GP-1-515, GP-1-683 and GP-1-665 were shown to have an $IC_{50}$ of 9 nM, 73 nM and 4.5 nM, respectively, in the adenosine kinase inhibition assay in intact cells.

EXAMPLE C

Effect on Adenosine Kinase Inhibition on Acute I.V. Hemodynamics in the Rat

The ability of the adenosine kinase inhibitor GP-1-238 to show effects on blood pressure, heart rate or body temperature was compared in anesthetized and conscious rats. Sprague Dawley rats were anesthetized with pentobarbital and catheterized in the jugular vein and carotid artery. GP-1-238 (0.1–5 mg/kg/min) was infused intravenously in stepwise increments (0.2 mL/min×5 minutes). The experiments in conscious rats were conducted in the same manner after rats had been catheterized and allowed to recover for 2 days following surgery. In conscious rats, in contrast to anesthetized animals, no hemodynamic effects were seen at doses which completely inhibited adenosine kinase in vivo See FIG. 1.

EXAMPLE D

Inhibition of Neutrophil Adherence to Fibroblasts or Endothelial Cells

Figure 2A:
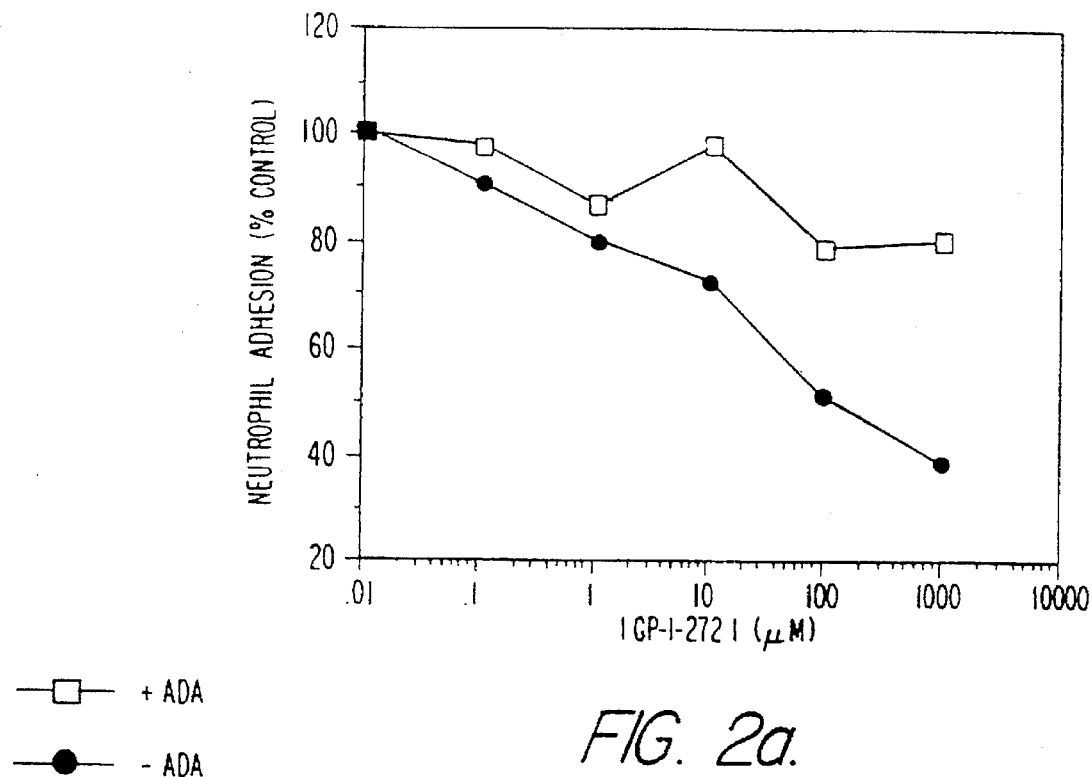
FIG. 2a depicts the dose-dependent inhibition of neutrophil adhesion to endothelial cells by the adenosine kinase inhibitor GP-1-272 and the reversal of this inhibition by co-treatment with adenosine deaminase ("ADA").
Figure 2B:
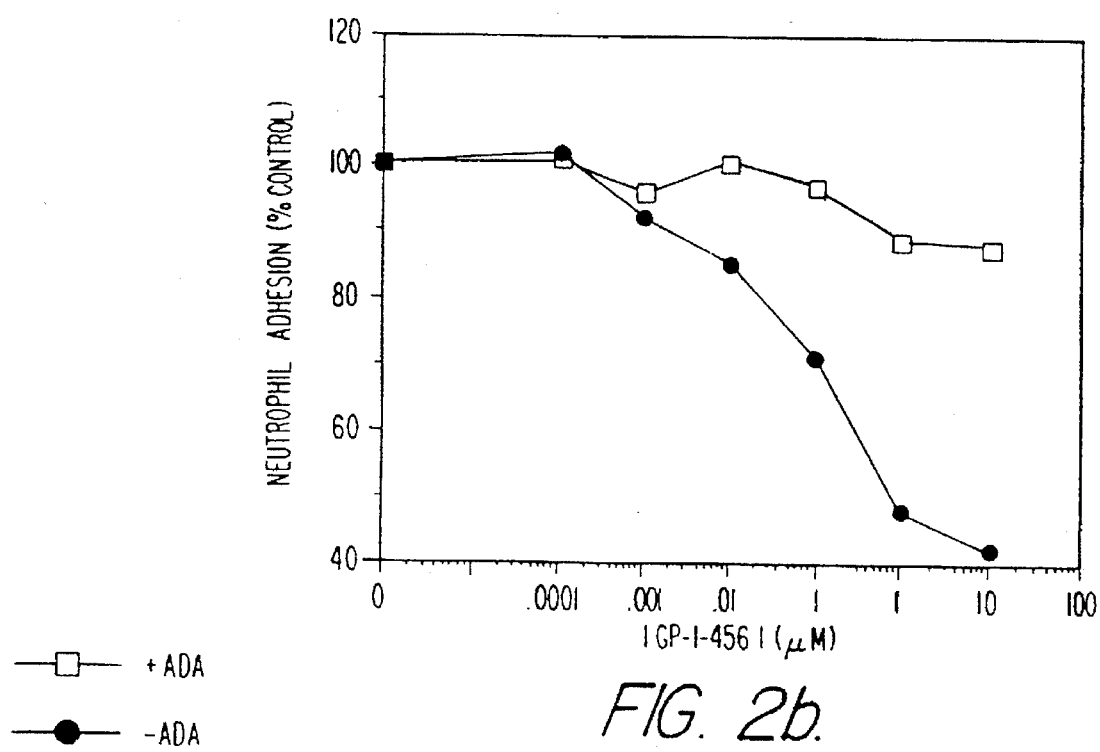
FIG. 2b depicts the dose-dependent inhibition of neutrophil adhesion to endothelial cells by the adenosine kinase inhibitor GP-1-456 and the reversal of this inhibition by co-treatment with adenosine deaminase ("ADA").

The ability of an adenosine kinase inhibitor to affect neutrophil adherence to fibroblasts and endothelial cells was evaluated in a cell culture model. Cultures of human dermal fibroblasts or human umbilical vein endothelial cells were washed and then incubated for 2 hours at 37° C. in a 5% $CO_2$ atmosphere in fresh medium containing different concentrations of the adenosine kinase inhibitors GP-1-272 and GP-1-456. These incubations were carried out in the presence of fMLP-stimulated human neutrophils isolated from whole blood (1.25×106/mL) with or without adenosine deaminase (0.125 U/mL). At the end of the incubation, the medium was removed and the monolayers of fibroblasts or endothelial cells and adherent neutrophils were fixed by addition of formaldehyde (3.7%) and, after washing to remove non-adherent neutrophils, adherent neutrophils were stained with Weigart's hematoxylin and counted under a light microscope. The results depicted in FIG. 2 show that the adenosine kinase inhibitors GP-1-272 and GP-1-456 inhibit neutrophil adhesion to endothelial cells and that this inhibition is reversed by adenosine deaminase treatment.

EXAMPLE E

Improved Survival in Endotoxemia in Adensoine Kinase Inhibitor-Treated Mice

Figure 9:
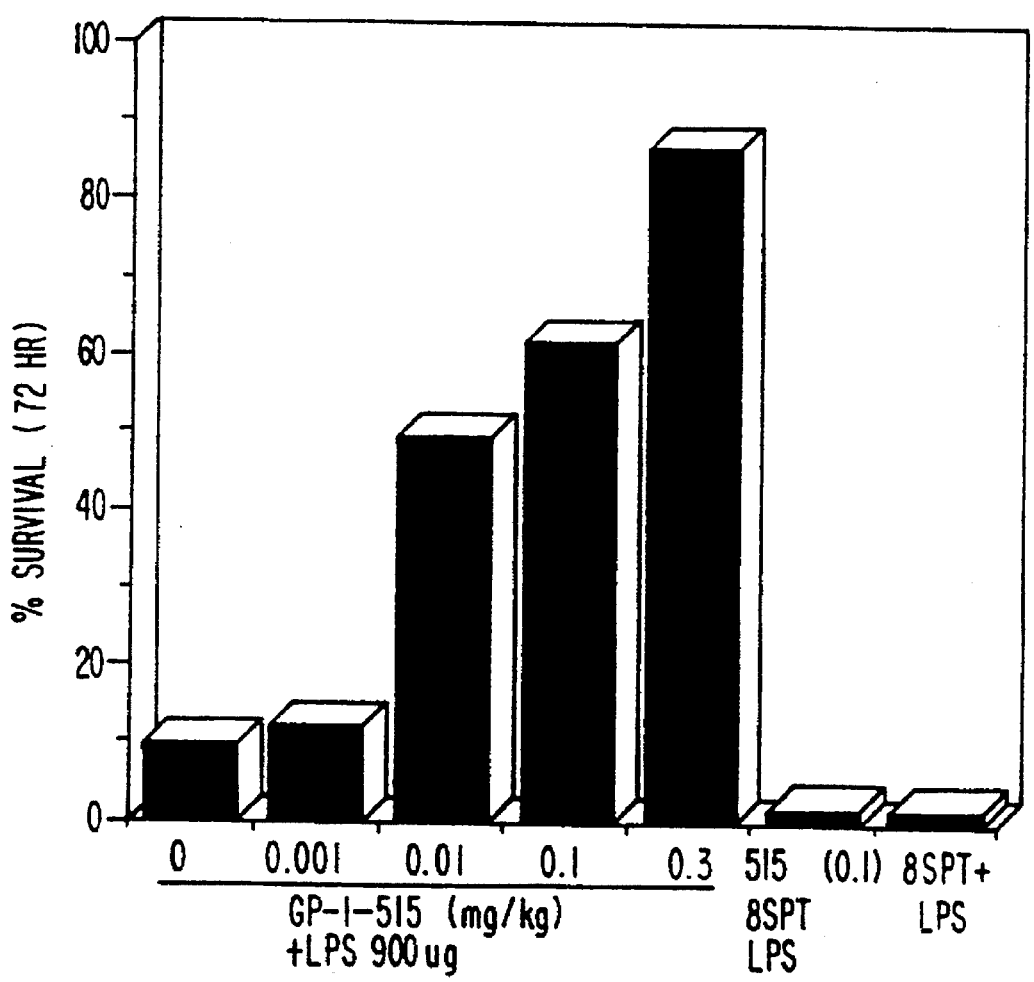
FIG. 9 depicts the effect of the adenosine kinase inhibitor, GP-1-515, in protecting against endotoxic shock and also depicts the effect of the adenosine receptor antagonist, 8-p-sulphophenyltheophylline, in blocking the GP-1-515-induced protection.

An adenosine kinase inhibitor (GP-1-515) was used to increase endogenous adenosine production in vivo. FIG. 9 shows the results of an experiment in which Balb/C mice received an intravenous injection of 900 ug of E. coli LPS (Sigma Chemical Co., St Louis, Mo.) followed immediately by an intravenous injection of an adenosine kinase inhibitor (GP-1-515) or carrier (10 animals per group). The adenosine kinase inhibitor-treated mice showed a dose-dependent increase in survival over that observed in the placebo group (p=0.015). Animals receiving 200 mg/kg i.p. of the adenosine receptor antagonist 8-p-sulphophenyltheophylline (8SPT) 30 minutes prior to the injection of LPS and drug completely inhibited the protective effect of GP-1-515.

EXAMPLE F

Adenosine Kinase Inhibitor as Prophylactic Treatment for Endotoxemia

As shown in Example E, intravenous treatment with an adenosine kinase inhibitor improves survival of mice if administered immediately after intravenous injection with LPS. In the following experiments, it was shown that an adenosine kinase inhibitor (GP-1-515) protects animals against endotoxemia if administered prophylactically. In these experiments, 25–30 gram male Balb/C mice received oral GP-1-515 (5 mg/kg in water) or vehicle by gavage. Six hours later, the animals received an intravenous injection of 700 ug of E. coli LPS (Sigma Chemical Co.). In an experiment involving 10 animals per group, 50% of mice in the adenosine kinase inhibitor-treated group survived for 2 days, while none of animals in the vehicle treated group survived for that time period (data not shown).

EXAMPLE G

Figure 10:
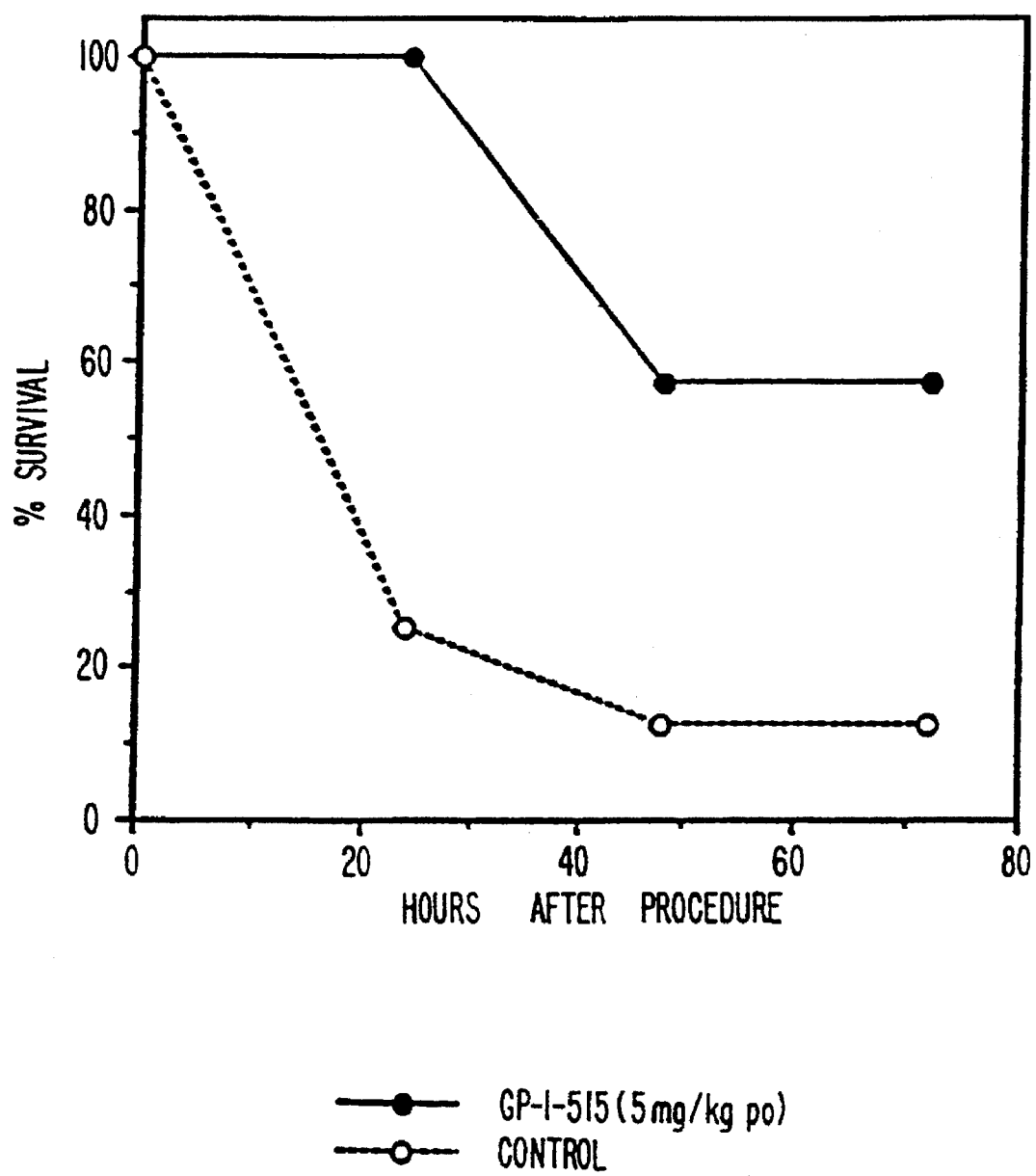
FIG. 10 depicts the effect of the adenosine kinase inhibitor, GP-1-515, on survival of rats after cecal ligation and puncture.

Efficacy of an Adensoine Kinase Inhibitor in Model of Chronic Sepsis, Cecal Ligation and Puncture Cecal ligation and puncture (CLP) is a model of bacterial peritonitis and septic shock which mimics systemic infections in humans. In these experiments, male CD rats were fasted overnight and treated orally with either GP-1-515 (5 mg/kg) or vehicle by gavage. Two hours later, animals were anesthetized with ether and the anterior abdominal wall was shaved. A midline incision was made and the cecum was exteriorized and ligated with 3-0 silk suture near the ilialcecal junction without causing bowel obstruction. The cecum was punctured twice on the anti-mesenteric side using a yellow tip disposable pipette tip (Fisher, Tustin, Calif.) and squeezed to ensure patency. The cecum was placed back in the abdominal cavity and the peritoneal wall was closed with 5-0 nylon sutures. The skin was closed with 9 mm stainless steel wound clips. The animals were resuscitated with a subcutaneous injection of 2 mL of sterile saline. No antibiotics were administered. The results of the experiments are presented in FIG. 10, which shows that the adenosine kinase inhibitor, GP-1-515, improved survival in this model of septic shock.

EXAMPLE H

Inhibition of TNF-Alpha Production by an Adenosine Kinase Inhibitor

Figure 11:
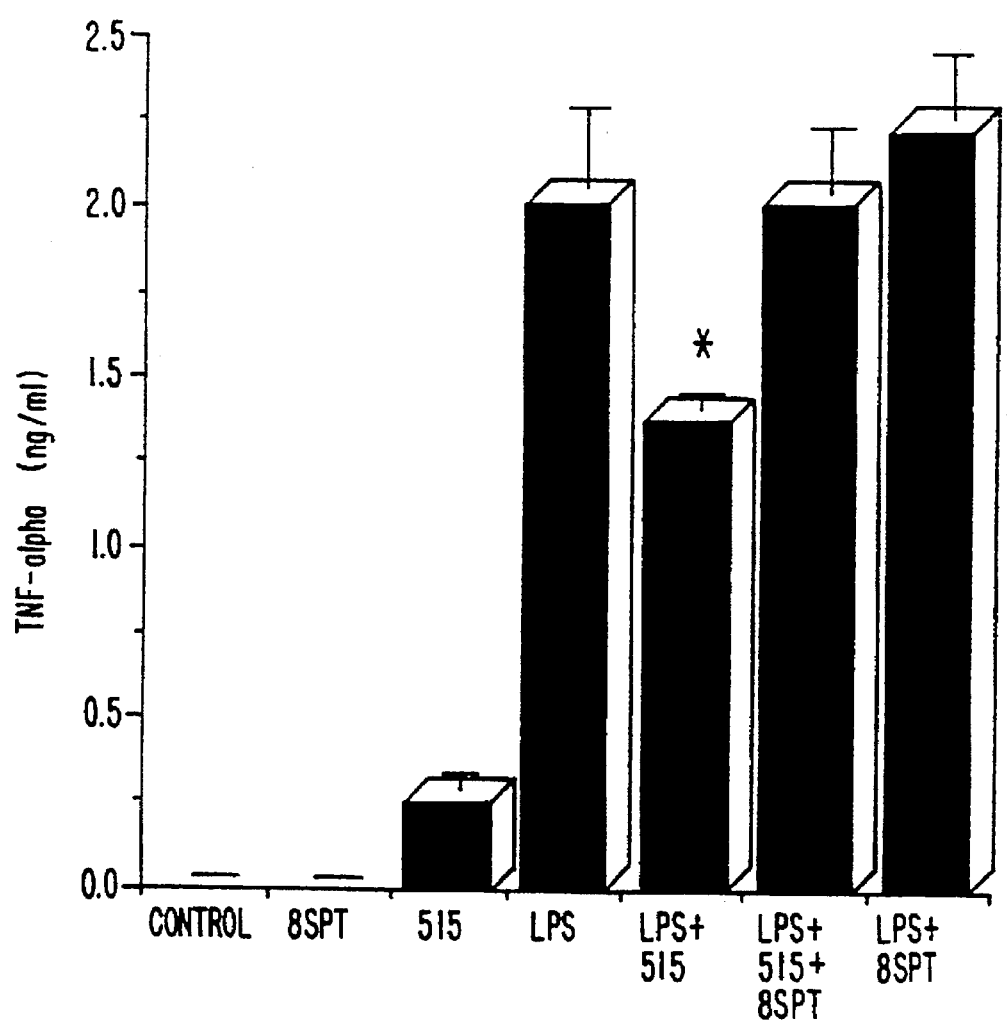
FIG. 11 depicts the effect of the adenosine kinase inhibitor, GP-1-515, on blood tumor necrosis factor alpha levels in endotoxic shock in mice.

In these experiments, plasma TNF-α levels were measured in GP-1-515and placebo-treated mice (8 animals per group). Balb/C mice received an intravenous injection of E. coli LPS (900 ug/animal) (Sigma Chemical Co.) followed immediately by a second injection with 0.1 mg/kg of GP-1-515 or vehicle. Some animals were pretreated with an intraperitoneal injection of the adenosine receptor antagonist 8SPT. One hour later, blood was obtained from ether anesthetized animals by intracardiac puncture using a heparinized syringe. Blood samples were chilled on ice, centrifuged at 5000 rpm in a microcentrifuge for 5 minutes, and the plasma removed. TNF-α levels in the plasma were assayed by ELISA according to the instructions provided by the manufacturer (Endogen, Cambridge, Mass.). As shown in FIG. 11, the adenosine kinase inhibitor, GP-1-515, significantly decreased plasma TNF-α levels (p<0.01). The decrease was prevented in animals pre-treated with 200 mg/kg i.p. of the adenosine receptor antagonist 8SPT 30 minutes prior to injection with LPS and GP-1-515.

EXAMPLE I

Effects on the Adenosine Kinase Inhibitor GP-1-456, in a Model of Inflammation The adenosine kinase inhibitor, GP-1-456, was examined for anti-inflammatory activity in adjuvant arthritis in rats. Lewis rats received a single subcutaneous tail injection of 0.75 mg *Mycobacterium butyricum* mixed in paraffin oil on day 0. The rats were treated with 3 mg/kg GP-1-456 p.o., or a vehicle control from day 1 through day 19. Hind paw volume was measured by Mercury displacement. On day 19, total mean hind paw edema, in mL, was 1.41±0.21 for treated rats versus 2.55±0.20 for untreated rats (p<0.05). This model demonstrated significant reduction of hind paw edema in adjuvant arthritis in animals treated with the adenosine kinase inhibitor, GP-1-456.

EXAMPLE J

Endotoxic Shock in Pigs

Male or female Yucatan miniature pigs (20–27 kg) were pre-medicated with xylazine (550 mg i.m.), ketamine (150 mg i.m.), and atropine (1 mg i.m.). The animals were intubated, administered 10 mg/kg of pentobarbital intravenously, and covered with a blanket to maintain normal body temperature. A pentobarbital infusion was maintained at 10 mg/kg/hr. The pigs were ventilated with 30% $O_2$ using a Harvard large animal respirator at 7–10 breaths/rain in order to achieve a blood pH of approximately 7.45–7.50. A bolus of 4 mg of Pancuronium bromide was given to inhibit muscle contraction in response to the cautery and the animals were hydrated with a continuous infusion of saline at 60–80 cc/hr. A left thoracotomy was performed in the third intercostal space and the pulmonary artery, carotid artery, external jugular vein were cannulated with PE-190 tubing. A line was also placed in the left atrium and a catheter tipped micromanometer was inserted into the left ventricle via an apical stab wound. A transit-time flow probe was placed on the pulmonary artery. Pressure readings were obtained using a Statham pressure transducer connected to a Gould strip chart recorder. Heparinized arterial blood samples for blood gases were obtained through the carotid arterial catheter. Drugs and endotoxin were infused through the external jugular catheter.

Figure 12A:
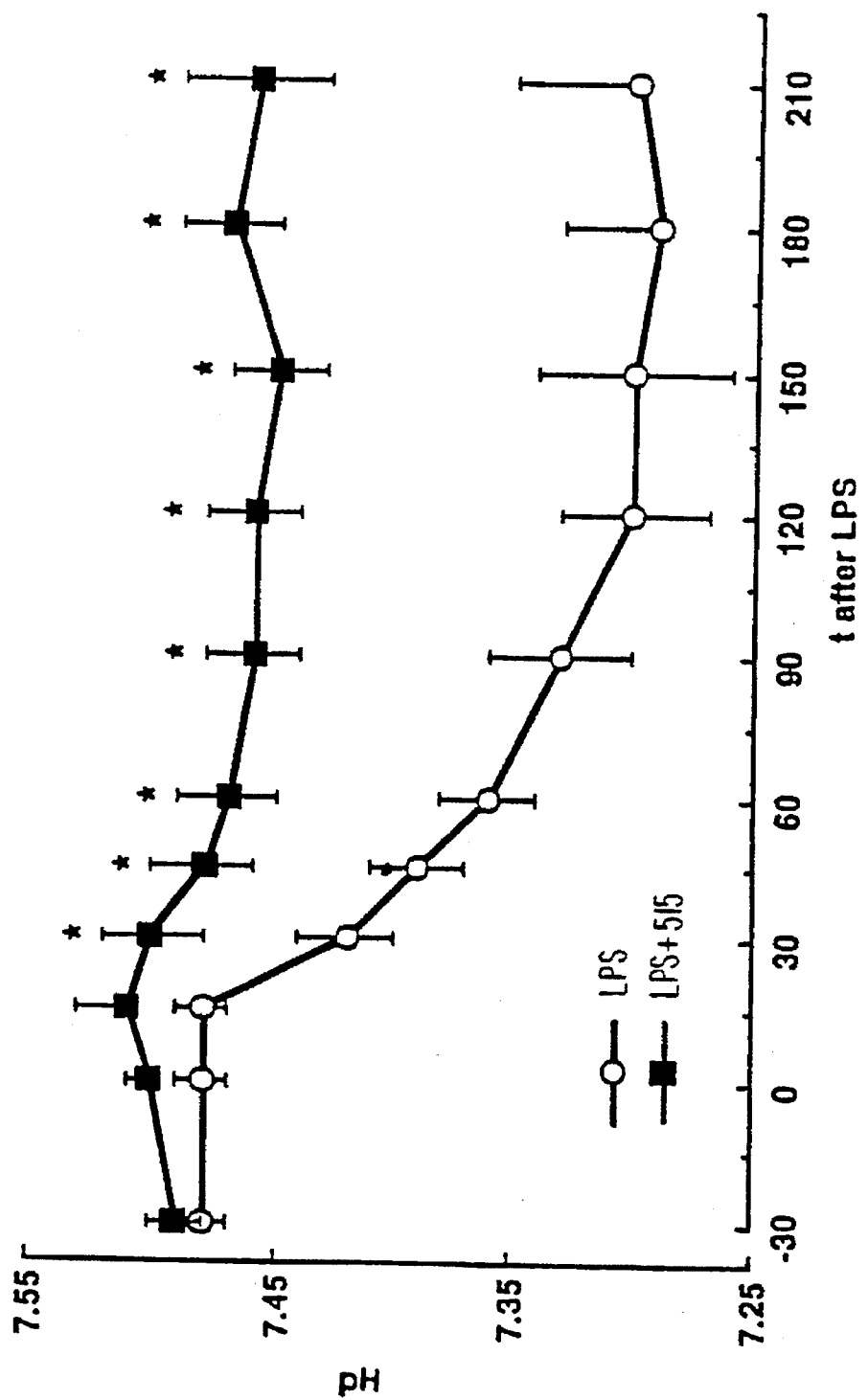
FIG. 12a shows that GP-1-515 improves gas exchange by lowering blood pH in LPS induced endotoxic shock in miniature pigs.
Figure 12B:
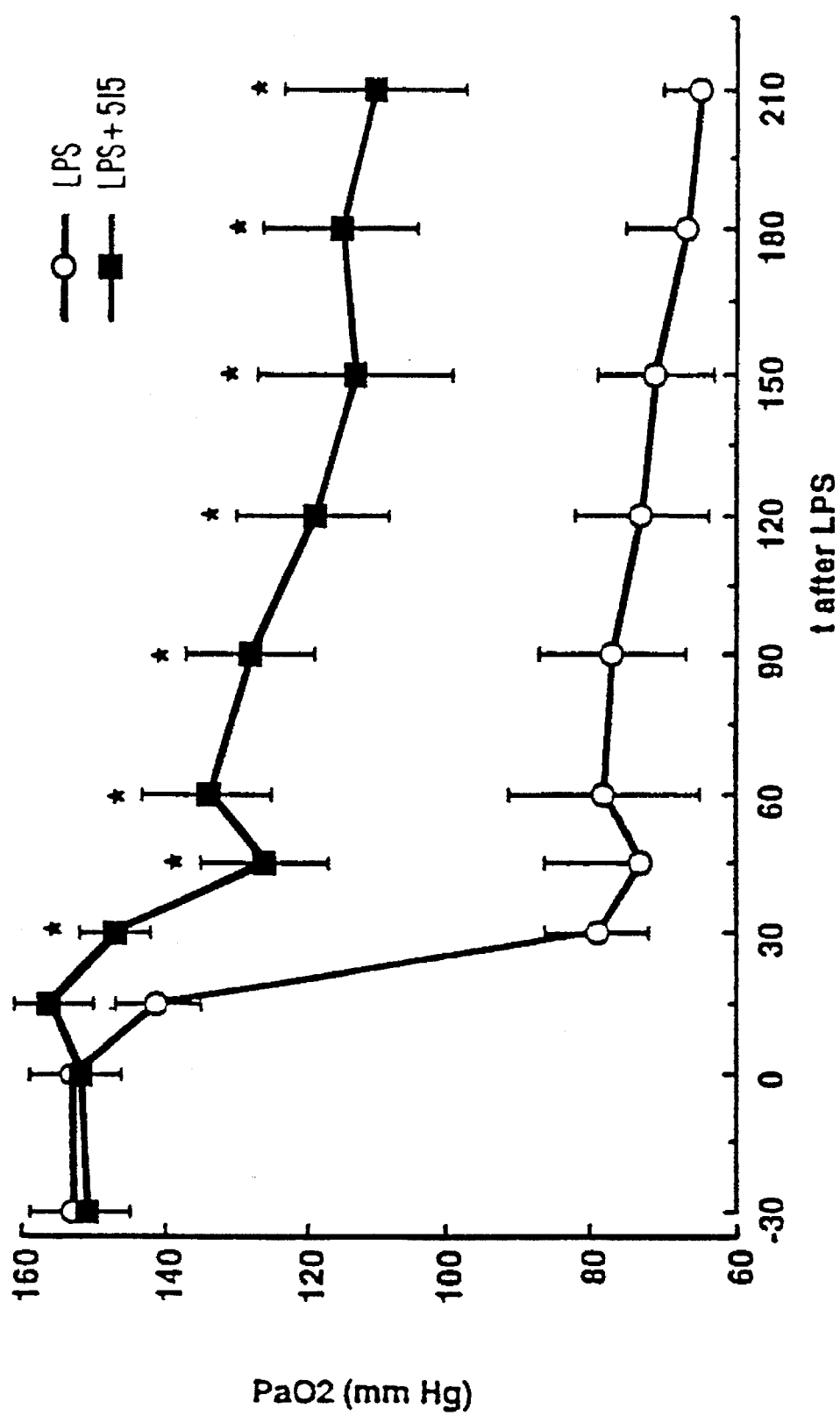
FIG. 12b shows that GP-1-515 improves blood gases by lowering PaO$_2$ in miniature pigs having LPS induced endotoxic shock.
Figure 12C:
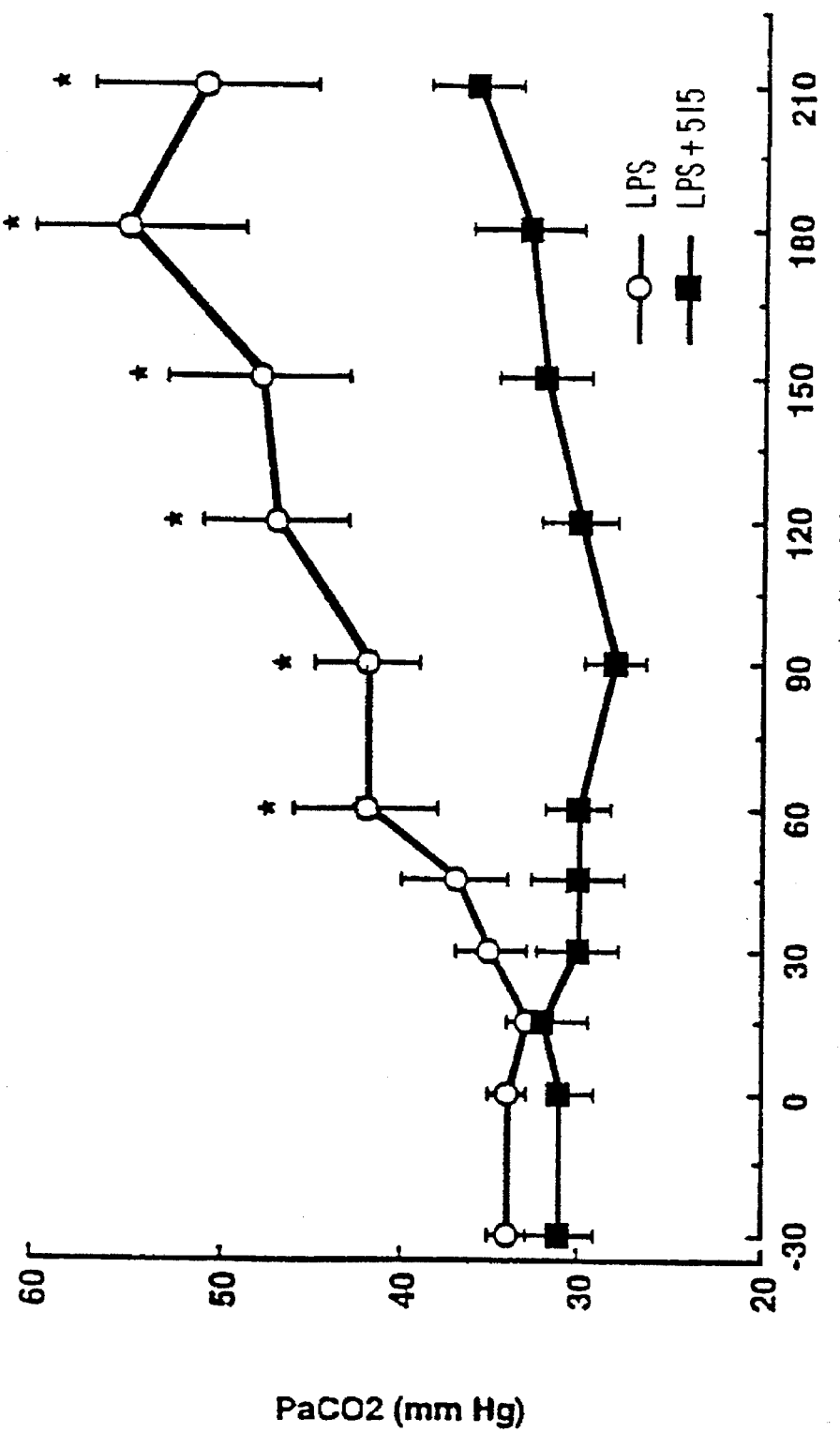
FIG. 12c shows that GP-1-515 improves blood glucose by increasing PaCo$_2$ in miniature pigs showing LPS induced endotoxic shock.
Figure 12D:
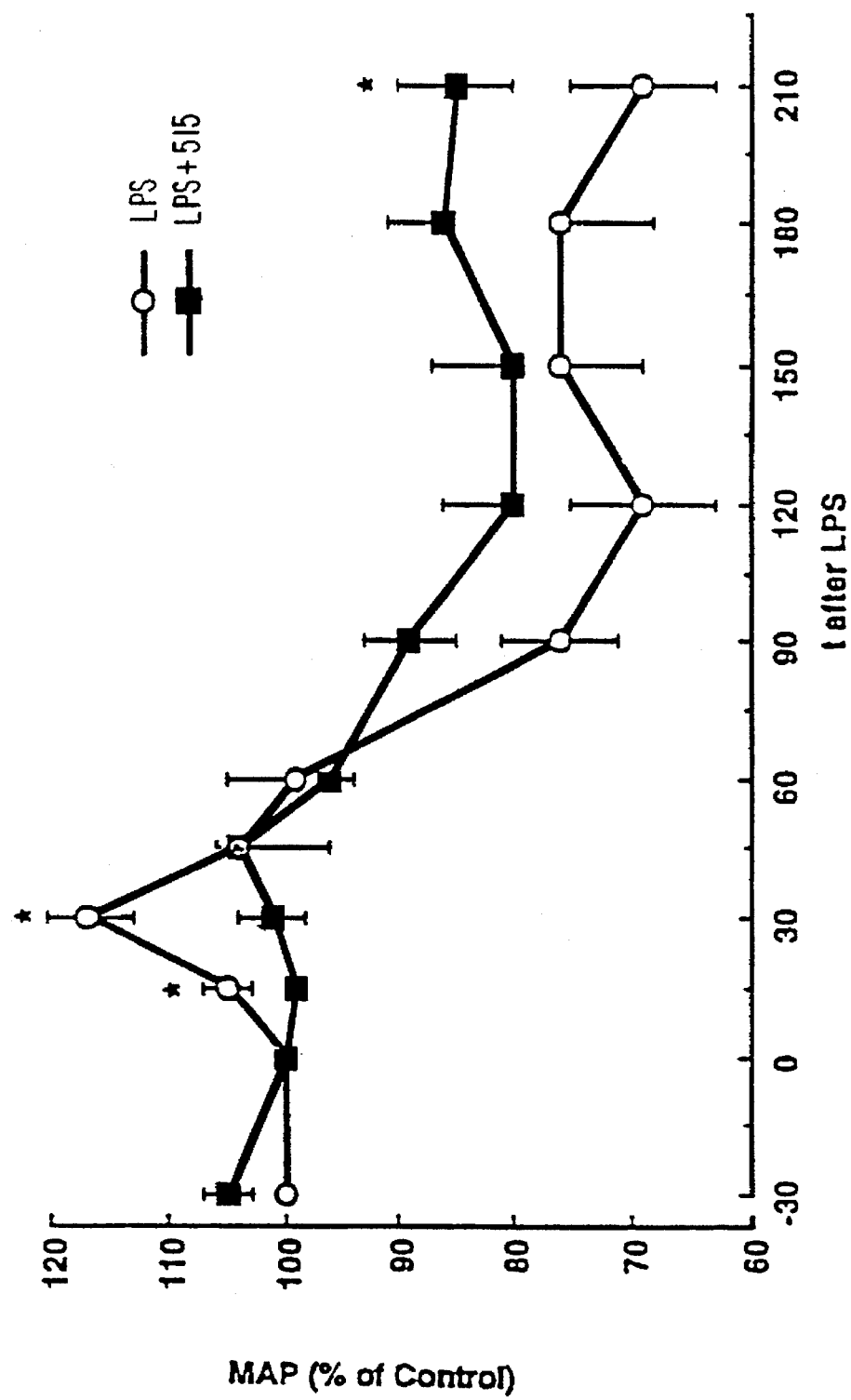
FIG. 12d shows that miniature pigs suffering from endotoxic shock had similar blood pressures whether or not they were treated with GP-1-515.
Figure 12E:
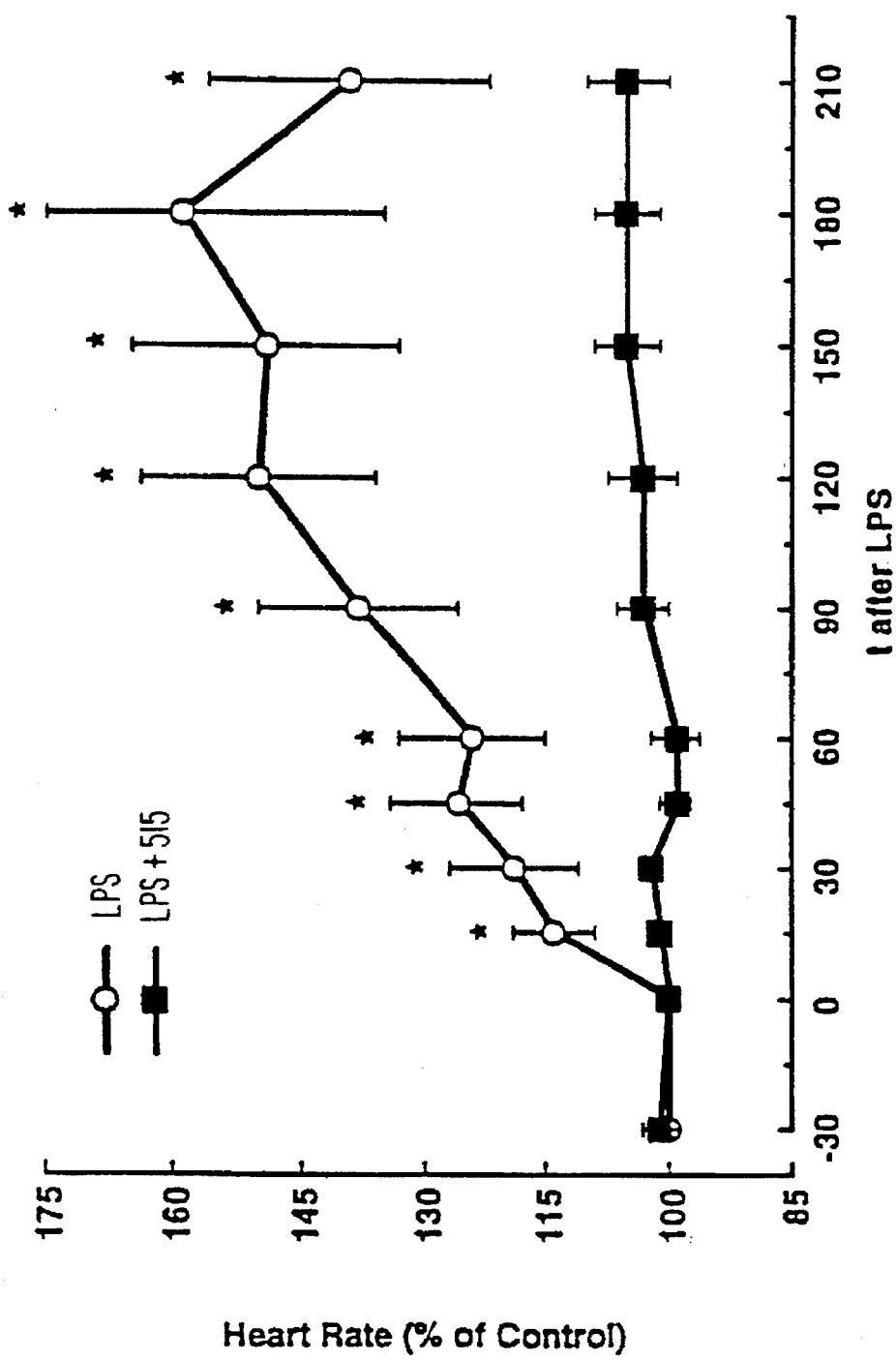
FIG. 12e shows that GP-1-515 treated miniature pigs with LPS induced endotoxic shock had lower heart rates than control animals.
Figure 13:
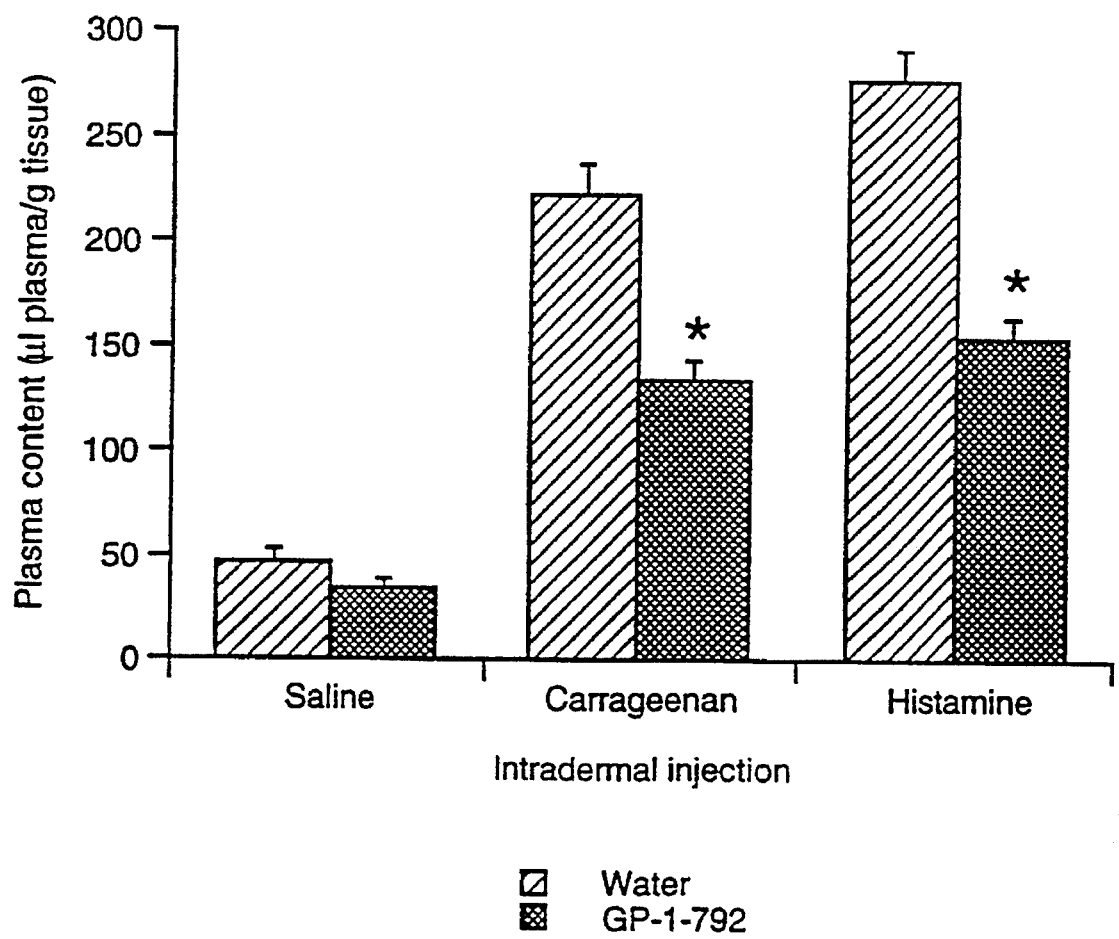
FIG. 13 depicts the effect of the adenosine kinase inhibitor GP-1-792 in the suppression of carrageenan and histamine induced plasma leakage following intradermal injections in rats.

After the animals had stabilized, a continuous infusion of GP-1-515 (0.3 μg/kg/m in) was started, followed 30 min later by a slow infusion of E. Coli 0111:B4 lipopolysaccharide (LPS) (Sigma Chemical Co., St. Louis, Mo.) over 30 min. The animals continued to receive GP-1-515 or vehicle for 4 additional hours and were ventilated with a fixed tidal volume and $FiO_2$. The most prominent findings pertained to gas exchange and pulmonary function, with marked protection observed in the GP-1-515-treated animals. Control animals developed severe hypoxemia, hypercapnia, and acidosis. However, the GP-1-515-treated animals had minimal changes in blood gases (see FIG. 12a,b,c for pH, $pO_2$, and $pCO_2$ data). Blood pressures were similar in the treated and control groups, although the control group,, required a significantly higher heart rate to maintain this pressure (see FIG. 12d,e for blood pressure and heart rate data). Other hemodynamic parameters, including pulmonary flow and pulmonary vascular resistance, were either not different or modestly improved compared to untreated animals. 4/7pigs in the control group died (several of whom had frank pulmonary edema) compared to 1/7in the GP-1-515-treated group. Upon completion of the study, the surviving animals were euthanized with an intravenous bolus of pentobarbital.

EXAMPLE K

Suppression of Vascular Leakage by Adenosine Kinase Inhibitor

Leakage of plasma into inflamed skin was measured using Evans' Blue (Sigma Chemical Co., St. Louis, Mo.), which binds irreversibly to albumin. Evans' Blue and bovine serum albumin (Sigma) were mixed (20 and 40 mg/mL PBS, respectively) and incubated for 15 min at room temperature in order to form a conjugate. The mixture was then filtered through a 0.45 μm pore syringe filter and immediately used. Male SA rats (150–200 g, Simonsen, Gilroy, Calif.) that had been shaved the previous day received GP-1-792 (4-amino-1-(5-amino-5-deoxy-2,3-di-O-acetyl-1-β-D-ribofuranosyl)-3-bromopyrazolo[3,4-d]pyrimidine, an orally bioavailable pro-drug of GP-1-515) or vehicle by gavage 1 hr prior to induction of skin lesions. The rats were then briefly anesthetized with halothane and dorsal skin injection sites (up to 4/rat) were stamped with a 12 mm test tube inked with a felt pad. Every site received 100 μl of an inflammatory agent or PBS injected intradermally into the middle of the circular mark. Inflammatory agents included carrageenan (1%) and histamine ($10^{-3}$M) (Sigma). Rats were then returned to their cages. Two hrs later, animals were again anesthetized and 0.5 mL blood was obtained through orbital plexus bleed. Following sacrifice of the rats, the injection sites were excised along the marked lines, and subcutaneous muscle and fat layers were removed from the skin biopsies. Each skin biopsy was weighed and cut in four, and its Evans' Blue content was extracted overnight by incubation in 1 mL N,N-dimethylformamide (Aldrich, Milwaukee, Wis.). The absorbance at 650 nm of plasma samples and skin extracts was read in a plate reader, and the plasma content of each skin piece was calculated and expressed as μl plasma/g tissue.

Carrageenan and histamine induced plasma leakage in rat skin, since the plasma content was significantly higher in skin sites injected with these agents compared to PBS-injected sites. Treatment with GP-1-792 (5 mg/kg p.o. 1 hr prior to experiment) significantly inhibited carrageenan- and histamine-induced plasma leakage by 47±5 and 51±5%, respectively (FIG. 14). Since histamine acts directly on endothelial cells, the protective effect of GP-1-792 can be mediated by an effect on endothelial cells in addition to a decrease in neutrophil accumulation in the tissue in this model as occurs with carrageenan.

EXAMPLE L

Effect on an Adenosine Kinase Inhibitor in a Burn Model

Female CF-1, non-Swiss, non-albino mice (age 8–12 weeks) (Charles River Laboratory, Wilmington, Mass.) were anesthetized with a 1–2 minute exposure to methoxyflurane (Abbott Labs, Chicago, Ill.). The shaved dorsum was burned by a 6-second exposure to steam using a 3.5×5.5 cm template to produce a 32% total body surface area full thickness burn. Animals were resuscitated with 1 mL of normal saline i.p., followed by 0.1 mg/kg i.p./injection of GP-1-515 or an equal amount of vehicle. Animals also received an i.p. injection of morphine sulfate (15 mg/kg). The animals were administered a second injection of GP-1-515 (0.1 mg/kg) or vehicle i.p. 6 hours after the burn. Animals were fasted for 4 hours before the burn and for 24 hours thereafter. After 48 hours, the animals were sacrificed by cervical dislocation and the abdomen was opened using aseptic techniques. Mesenteric lymph nodes were harvested and weighed in sterile bags, homogenized in Trypticate Soy Broth (BBL, Becton Dickinson Microbiology System, Cockeysville, Md.). Ser. dilutions of the homogenate were plated on head-brain-infusion agar plates (BBL, Becton Dickinson) at 37° C. and the presence or absence of bacterial colonies was determined 48 hours later. In experiments involving approximately 120 animals, 52% of control mice had positive mesenteric lymph node cultures compared to 32% of GP-1-515-treated mice (p<0.05). Hence bacterial translocation after a severe burn was significantly decreased by GP-1-515.

We claim:

1. A method of treating a condition involving an inflammatory response selected from arthritis and SIRS in a patient in need of treatment therefor which comprises administering to said patient an inflammatory response decreasing effective amount of a compound which selectively inhibits adenosine kinase.

2. A method according to claim 1 wherein SIRS results in sepsis.

3. A method of treating a condition involving a localized or systemic inflammatory response due to infection in a patient in need of treatment therefor which comprises administering to said patient an inflammatory response decreasing effective amount of a compound which selectively inhibits adenosine kinase.

4. A method according to claim 3 wherein said condition is selected from the group consisting of endotoxic shock, ARDS, endotoxemia, sepsis, septicemia, septic shock, peritonitis, vascular leakage and arthritis.

5. A method of treating a condition characterized by an inflammatory response in a patient in need of treatment and which condition is selected from SIRS and arthritis and is ameliorated by decreased TNF-α production which comprises administering to said patient, a TNF-α level decreasing amount of a compound which selectively inhibits adenosine kinase.

6. A method of treating a condition characterized by an inflammatory response to tissue injury in a patient in need of treatment therefor and wherein said injury is a burn or an injury which causes vascular leakage which comprises administering to said patient an amount of a compound which selectively inhibits adenosine kinase effective to reduce the inflammatory response.

7. A method according to any one of claims 1, 3, 5 or 6 wherein said compound has the following formula:

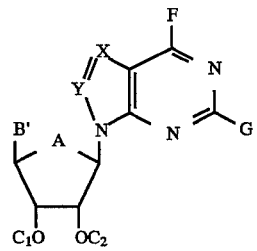

wherein:

(a) A is oxygen;

(b) B' is —$(CH_2)_n$—B wherein n is 1, 2, 3 or 4 and B is hydrogen, alkyl, alkoxy, amino, alkylamino, acylamino, hydrocarbyloxycarbonylamino, mercapto, alkylthio, azido, cyano, halogen, or B' is alkenyl or alkynyl;

(c) $C_1$ and $C_2$ are each independently hydrogen, acyl, hydrocarbyloxycarbonyl or taken together from a 5-membered ring wherein $C_1$ is a single bond to $C_2$ and $C_2$ is carbonyl or α-alkoxyalkylidene;

(d) X is —C(—D)= and Y is —N= or —C(—E)=;

(e) D is hydrogen, halogen, alkyl, aryl, aralkyl, alkenyl, alkynyl, haloalkyl, cyano, cyanoalkyl, acyl, carboxamido, a carboxylic acid or carboxylic ester group, alkoxy, aryloxy, aralkyloxy, alkylthio, arylthio, aratkylthio, amino, alkylamino, arylamino, aralkylamino, acylamino, or nitro;

(f) E is hydrogen, halogen, alkyl, or alkylthio;

(g) F is alkyl, aryl, aralkyl, halogen, amino, alkylamino, arylamino, aralkylamino, cyano, cyanoalkyl, alkoxy, aryloxy, aralkyloxy, alkylthio, arylthio, aratkylthio, indolinyl or indolyl, pyrrolidinyl or piperazinyl; and (h) G is hydrogen, halogen, lower alkyl, lower alkoxy, lower alkylamino or lower alkylthio; and pharmaceutically acceptable salts thereof; with the proviso that: when A is oxygen and (i) X is —C(—D)= and —C(—E)=, then if B' is methyl, D is halogen, cyano or carboxamido, F is amino, then G is not hydrogen; or if D is hydrogen, then F is not amino; or (ii) X is —C(—D)= and y is —N=, if B is hydrogen or halogen, D and G are hydrogen, then F is not amino.

8. A method according to any one of claims 1, 3, 5, or 6 wherein said compound has the following formula:

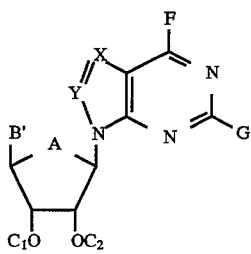

wherein:

(a) A is oxygen (b) B' is —(CH$_2$)$_n$B wherein n is 1, 2, 3 or 4 and B is hydroxy, acyloxy, hydrocarbyloxycarbonyloxy, or —OCONR$_2$ wherein R is independently hydrocarbyl;

(c) C$_1$ and C$_2$ are each independently hydrogen, acyl, hydrocarbyloxycarbonyl or taken together form a 5-membered ring wherein C$_1$ is a single bond to C$_2$ and C$_2$ is carbonyl or α-alkoxyalkylidene;

(d) X is —C(—D)= and Y is —N=;

(e) D is halogen, aryl or aralkyl;

(f) F is alkyl, aryl, aralkyl, halogen, amino, alkylamino, arylamino, aralkylamino, cyano, cyanoalkyl, alkoxy, aryloxy, aralkoxy, alkylthio, arylthio, aralkythio, indolinyl or indolyl, pyrrolidinyl or piperazinyl; and (g) G is hydrogen, halogen, lower alkyl, lower alkoxy, or lower alkylthio; and pharmaceutically acceptable salts thereof; with the proviso that when D is halogen, then F is not amino.

9. A method according to any one of claims 1, 3, 5, or 6 wherein said compound has the following formula:

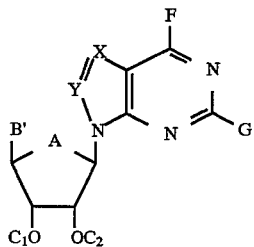

wherein:

(a) A is oxygen;

(b) B' is —(CH$_2$)$_n$B wherein n is 1, 2, 3 or 4 and B is hydroxy, acyloxy, hydrocarbyloxycarbonyloxy, or —OCONR$_2$ wherein R is hydrocarbyl;

(c) C$_1$ and C$_2$ are each independently hydrogen, acyl, hydrocarbyloxycarbonyl or taken together form a 5-membered ring wherein C$_1$ is a single bond to C$_2$ and C$_2$ is carbonyl or α-alkoxyalkylidene;

(d) X is —C(—D)= and Y is —C(—E)=;

(e) D is aryl or aralkyl;

(f) E is hydrogen, halogen, alkyl, or alkylthio;

(g) F is alkyl, aryl, aralkyl, halogen, amino, alkylamino, arylamino, aralkylamino, cyano, cyanoalkyl, alkoxy, aryloxy, aralkyloxy, alkylthio, arylthio, aralkylthio, indolinyl or indolyl, pyrrolidinyl or piperazinyl; and (h) G is hydrogen, halogen, lower alkyl, lower alkoxy, or lower alkylthio; and pharmaceutically acceptable salts thereof; with the proviso that when D is oxadiazolyl, triazolyl or triazinyl and E and G are both hydrogen, then F is not amino.

10. A method according to any one of claims 1, 3, 5, or 6 wherein said compound is 4-amino-5-iodo-7-(5-deoxy-1-β-D-ribofuranosyl)pyrrolo[2,3-d]pyrimidine.

11. A method according to any one of claims 1, 3, 5 or 6 wherein said compound is 4-amino-1-(5-amino-β-deoxy-1-β-D-ribofuranosyl)-3-bromo-pyrazolo[3,4-d]pyrimidine.

12. A method according to any one of claims 1, 3, 5 or 6, wherein said compound is administered orally.

13. A method according to any one of claims 1, 3, 5 or 6 wherein said compound is administered intravenously.

* * * * *